US008188084B2

(12) United States Patent
Jones et al.

(10) Patent No.: US 8,188,084 B2
(45) Date of Patent: May 29, 2012

(54) PYRIDINONE AND PYRIDAZINONE DERIVATIVES AS INHIBITORS OF POLY (ADP-RIBOSE) POLYMERASE (PARP)

(75) Inventors: Philip Jones, Pomezia (IT); Olaf Kinzel, Pomezia (IT); Giovanna Pescatore, Pomezia (IT); Laura Llauger Bufi, Pomezia (IT); Carsten Schultz-Fademrecht, Pomezia (IT); Federica Ferrigno, Pomezia (IT)

(73) Assignee: Istituto di Ricerche di Biologia Molecolare P. Angeletti SpA., Pomezia, Rome (IT)

( * ) Notice: Subject to any disclaimer, the term of this patent is extended or adjusted under 35 U.S.C. 154(b) by 660 days.

(21) Appl. No.: 12/227,513

(22) PCT Filed: May 25, 2007

(86) PCT No.: PCT/GB2007/050295
§ 371 (c)(1),
(2), (4) Date: Nov. 19, 2008

(87) PCT Pub. No.: WO2007/138351
PCT Pub. Date: Dec. 6, 2007

(65) Prior Publication Data
US 2009/0176765 A1    Jul. 9, 2009

(30) Foreign Application Priority Data
May 31, 2006 (GB) .................... 0610680.1

(51) Int. Cl.
C07D 401/12 (2006.01)
A61P 35/00 (2006.01)
A61P 9/10 (2006.01)
A61P 29/00 (2006.01)
(52) U.S. Cl. ......... 514/252.02; 514/252.03; 514/252.05; 544/238
(58) Field of Classification Search ............ 544/238, 544/239; 514/247, 252.01, 252.02, 252.03, 514/252.05
See application file for complete search history.

(56) References Cited

U.S. PATENT DOCUMENTS

| | | | | |
|---|---|---|---|---|
| 6,750,350 | B2 * | 6/2004 | Chen et al. | 546/268.1 |
| 7,189,718 | B2 * | 3/2007 | Dunn et al. | 514/236.5 |
| 7,288,542 | B2 * | 10/2007 | Dunn et al. | 514/247 |
| 7,291,729 | B2 * | 11/2007 | Kertesz et al. | 544/239 |
| 7,452,882 | B2 * | 11/2008 | Haynes et al. | 514/242 |
| 7,625,897 | B2 * | 12/2009 | Saito et al. | 514/242 |
| 2005/0234236 | A1 | 10/2005 | Kertesz et al. | |
| 2008/0161280 | A1 | 7/2008 | Gandhi et al. | |
| 2008/0269234 | A1 | 10/2008 | Gandhi et al. | |
| 2011/0105509 | A1 * | 5/2011 | Kaila et al. | 514/248 |

FOREIGN PATENT DOCUMENTS

| | | |
|---|---|---|
| EP | 0714895 | 6/1996 |
| EP | 0810218 | 12/1997 |
| WO | WO02/36576 | 5/2002 |
| WO | WO02/090334 | 11/2002 |
| WO | WO03/093261 | 11/2003 |
| WO | WO2004/080976 | 9/2004 |
| WO | WO2004/085406 | 10/2004 |
| WO | WO2005/090317 | 9/2005 |
| WO | WO2005/097750 | 10/2005 |
| WO | WO2006/021801 | 3/2006 |
| WO | WO 2007/009913 | 1/2007 |
| WO | WO2008/114023 | 9/2008 |
| WO | WO2008/122810 | 10/2008 |
| WO | W02009/004356 | 1/2009 |

OTHER PUBLICATIONS

Gaymes, et al., Haematologica, 2009; 94(5), 638-646.*
CancerConnect.com, Phase III Trial Fails to Find Benefit of PARP Inhibitor for Triple-Negative Breast Cancer, http://news.cancerconnect.com/phase-iii-trial-fails-to-find-benefit-of-parp-inhibitor-for-triple-negative-breast-cancer/, downloaded Aug. 23, 2011.*
Turner, et al., The EMBO J. (2008) 27, 1368-1377.*
Chantegrel, et al., J. Het. Chem. (1990), 27(4), 927-34.*
Wermuth, et al., J. Med. Chem. (1989), 32(3), 528-37.*
Leeson, et al., Journal of Medicinal Chemistry, American Chemical Society, vol. 32(2), pp. 320-336 (1989).
Jagtap, et al., Nature Reviews Drug Discovery, vol. 4, p. 421 (2005).
Bryant, et al., Nature, vol. 434, pp. 913-917 (2005).
Peukert, et al., Exp. Opin. Ther. Patents, vol. 14(11), p. 1531 (2004).
Loh, et al., Bioorganic & Medicinal Chemistry Letters, vol. 15(9), pp. 2235-2238 (2005).
Cockcroft, et al., Bioorganic & Medicinal Chemistry Letters, vol. 16(4), pp. 1040 (2006).

* cited by examiner

Primary Examiner — James O Wilson
Assistant Examiner — Cecilia M Jaisle
(74) Attorney, Agent, or Firm — Yong Zhao; David A. Muthard

(57) ABSTRACT

The present invention relates to compounds of formula I:

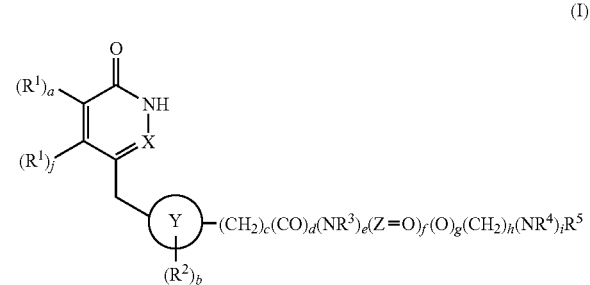

and pharmaceutically acceptable salts or tautomers thereof which are inhibitors of poly(ADP-ribose)polymerase (PARP) and thus useful for the treatment of cancer, inflammatory diseases, reperfusion injuries, ischaemic conditions, stroke, renal failure, cardiovascular diseases, vascular diseases other than cardiovascular diseases, diabetes mellitus, neurodegenerative diseases, retroviral infections, retinal damage, skin senescence and UV-induced skin damage, and as chemo- or radiosensitizers for cancer treatment.

2 Claims, No Drawings

PYRIDINONE AND PYRIDAZINONE DERIVATIVES AS INHIBITORS OF POLY (ADP-RIBOSE) POLYMERASE (PARP)

PRIORITY CLAIM

This application is a §371 National Stage Application of PCT/GB2007/050295, filed on May 25, 2007, which claims priority from GB Provisional Application Serial Number 0610680.1, filed on May 31, 2006.

The present invention relates to pyridinone and pyridazinone derivatives which are inhibitors of the enzyme poly (ADP-ribose)polymerase (PARP), previously known as poly (ADP-ribose)synthase and poly(ADP-ribosyl)transferase. The compounds of the present invention are useful as monotherapies in tumors with specific defects in DNA-repair pathways and as enhancers of certain DNA-damaging agents such as anticancer agents and radiotherapy. Further, the compounds of the present invention are useful for reducing cell necrosis (in stroke and myocardial infarction), down regulating inflammation and tissue injury, treating retroviral infections and protecting against the toxicity of chemotherapy.

Poly(ADP-ribose) polymerase (PARP) constitute a super family of eighteen proteins containing PARP catalytic domains (*Bioessays* (2004) 26:1148). These proteins include PARP-1, PARP-2, PARP-3, tankyrase-1, tankyrase-2, vault-PARP and TiPARP. PARP-1, the founding member, consists of three main domains: an amino (N)-terminal DNA-binding domain (DBD) containing two zinc fingers, the automodification domain, and a carboxy (C)-terminal catalytic domain.

PARP are nuclear and cytoplasmic enzymes that cleave $NAD^+$ to nicotinamide and ADP-ribose to form long and branched ADP-ribose polymers on target proteins, including topoisomerases, histones and PARP itself (*Biochem. Biophys. Res. Commun.* (1998) 245:1-10).

Poly(ADP-ribosyl)ation has been implicated in several biological processes, including DNA repair, gene transcription, cell cycle progression, cell death, chromatin functions and genomic stability.

The catalytic activity of PARP-1 and PARP-2 has been shown to be promptly stimulated by DNA strand breakages (see *Pharmacological Research* (2005) 52:25-33). In response to DNA damage, PARP-1 binds to single and double DNA nicks. Under normal physiological conditions there is minimal PARP activity, however, upon DNA damage an immediate activation of PARP activity of up to 500-fold occurs. Both PARP-1 and PARP-2 detect DNA strand interruptions acting as nick sensors, providing rapid signals to halt transcription and recruiting the enzymes required for DNA repair at the site of damage. Since radiotherapy and many chemotherapeutic approaches to cancer therapy act by inducing DNA damage, PARP inhibitors are useful as chemo- and radiosensitizers for cancer treatment. PARP inhibitors have been reported to be effective in radio sensitizing hypoxic tumor cells (U.S. Pat. No. 5,032,617, U.S. Pat. No. 5,215,738 and U.S. Pat. No. 5,041,653).

Most of the biological effects of PARP relate to this poly (ADP-ribosyl)ation process which influences the properties and function of the target proteins; to the PAR oligomers that, when cleaved from poly(ADP-ribosyl)ated proteins, confer distinct cellular effects; the physical association of PARP with nuclear proteins to form functional complexes; and the lowering of the cellular level of its substrate $NAD^+$ (*Nature Review* (2005) 4:421-440).

Besides being involved in DNA repair, PARP may also act as a mediator of cell death. Its excessive activation in pathological conditions such as ischemia and reperfusion injury can result in substantial depletion of the intercellular $NAD^+$, which can lead to the impairment of several $NAD^+$ dependent metabolic pathways and result in cell death (see *Pharmacological Research* (2005) 52:44-59). As a result of PARP activation, $NAD^+$ levels significantly decline. Extensive PARP activation leads to severe depletion of $NAD^+$ in cells suffering from massive DNA damage. The short half-life of poly(ADP-ribose) results in a rapid turnover rate, as once poly(ADP-ribose) is formed, it is quickly degraded by the constitutively active poly(ADP-ribose) glycohydrolase (PARG). PARP and PARG form a cycle that converts a large amount of $NAD^+$ to ADP-ribose, causing a drop of $NAD^+$ and ATP to less than 20% of the normal level. Such a scenario is especially detrimental during ischemia when deprivation of oxygen has already drastically compromised cellular energy output. Subsequent free radical production during reperfusion is assumed to be a major cause of tissue damage. Part of the ATP drop, which is typical in many organs during ischemia and reperfusion, could be linked to $NAD^+$ depletion due to poly(ADP-ribose) turnover. Thus, PARP inhibition is expected to preserve the cellular energy level thereby potentiating the survival of ischemic tissues after insult. Compounds which are inhibitors of PARP are therefore useful for treating conditions which result from PARP mediated cell death, including neurological conditions such as stroke, trauma and Parkinson's disease.

PARP inhibitors have been demonstrated as being useful for the specific killing of BRCA-1 and BRCA-2 deficient tumors (*Nature* (2005) 434:913-916 and 917-921; and *Cancer Biology & Therapy* (2005) 4:934-936).

PARP inhibitors have been demonstrated to be selective in killing cells with defects in ATM, DNA_PK or KU80 (*Nucleic Acid Research* (2006) 34:1685-1691).

PARP inhibitors have been shown to enhance the efficacy of anticancer drugs (*Pharmacological Research* (2005) 52:25-33), including platinum compounds such as cisplatin and carboplatin (*Cancer Chemother Pharmacol* (1993) 33:157-162 and *Mol Cancer Ther* (2003) 2:371-382). PARP inhibitors have been shown to increase the antitumor activity of topoisomerase 1 inhibitors such as Irinotecan and Topotecan (*Mol Cancer Ther* (2003) 2:371-382; and *Clin Cancer Res* (2000) 6:2860-2867) and this has been demonstrated in in vivo models (*J Natl Cancer Inst* (2004) 96:56-67).

PARP inhibitors have been shown to restore susceptibility to the cytotoxic and antiproliferative effects of temozolomide (TMZ) (see *Curr Med Chem* (2002) 9:1285-1301 and *Med Chem Rev Online* (2004) 1:144-150). This has been demonstrated in a number of in vitro models (*Br J Cancer* (1995) 72:849-856; *Br J Cancer* (1996) 74:1030-1036; *Mol Pharmacol* (1997) 52:249-258; *Leukemia* (1999) 13:901-909; *Glia* (2002) 40:44-54; and *Clin Cancer Res* (2000) 6:2860-2867 and (2004) 10:881-889) and in vivo models (*Blood* (2002) 99:2241-2244; *Clin Cancer Res* (2003) 9:5370-5379 and *J Natl Cancer Inst* (2004) 96:56-67). PAPR inhibitors have also been shown to prevent the appearance of necrosis induced by selective AG-adenine methylating agents such as $MeOSO_2(CH_2)$-lexitropsin (Me-Lex) (*Pharmacological Research* (2005) 52:25-33).

PARP inhibitors have been shown to act as radiation sensitizers. PARP inhibitors have been reported to be effective in radiosensitizing (hypoxic) tumor cells and effective in preventing tumor cells from recovering from potentially lethal (*Br. J. Cancer* (1984) 49(Suppl. VI):34-42; and *Int. J. Radiat. Bioi.* (1999) 75:91-100) and sub-lethal (*Clin. Oncol.* (2004) 16(1):29-39) damage of DNA after radiation therapy, presumably by their ability to prevent DNA strand break rejoining and by affecting several DNA damage signaling pathways.

PARP inhibitors have also been shown to be useful for treating acute and chronic myocardial diseases (see *Pharmacological Research* (2005) 52:34-43). For instance, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%). These results make it reasonable to assume that PARP inhibitors could salvage previously ischemic heart or reperfusion injury of skeletal muscle tissue (PNAS (1997) 94:679-683). Similar findings have also been reported in pigs (*Eur. J. Pharmacol.* (1998) 359:143-150 and *Ann. Thorac. Surg.* (2002) 73:575-581) and in dogs (*Shock.* (2004) 21:426-32).

PARP inhibitors have been demonstrated as being useful for treating certain vascular diseases, septic shock, ischemic injury and neurotoxicity (*Biochim. Biophys. Acta* (1989) 1014:1-7; *J. Clin. Invest.* (1997) 100:723-735). Oxygen radical DNA damage that leads to strand breaks in DNA, which are subsequently recognized by PARP, is a major contributing factor to such disease states as shown by PARP inhibitor studies (*J. Neurosci. Res.* (1994) 39:38-46 and *PNAS* (1996) 93:4688-4692). PARP has also been demonstrated to play a role in the pathogenesis of hemorrhagic shock (*PNAS* (2000) 97:10203-10208).

PARP inhibitors have been demonstrated as being useful for treatment of inflammation diseases (see *Pharmacological Research* (2005) 52:72-82 and 83-92).

It has also been demonstrated that efficient retroviral infection of mammalian cells is blocked by the inhibition of PARP activity. Such inhibition of recombinant retroviral vector infections has been shown to occur in various different cell types (*J. Virology*, (1996) 70(6):3992-4000). Inhibitors of PARP have thus been developed for use in anti-viral therapies and in cancer treatment (WO 91/18591).

In vitro and in vivo experiments have demonstrated that PARP inhibitors can be used for the treatment or prevention of autoimmune diseases such as Type I diabetes and diabetic complications (*Pharmacological Research* (2005) 52:60-71).

PARP inhibition has been speculated as delaying the onset of aging characteristics in human fibroblasts (*Biochem. Biophys. Res. Comm.* (1994) 201(2):665-672 and *Pharmacological Research* (2005) 52:93-99). This may be related to the role that PARP plays in controlling telomere function (*Nature Gen.*, (1999) 23(1):76-80).

The vast majority of PARP inhibitors to date interact with the nicotinamide binding domain of the enzyme and behave as competitive inhibitors with respect to NAD+ (*Expert Opin. Ther. Patents* (2004) 14:1531-1551). Structural analogues of nicotinamide, such as benzamide and derivatives were among the first compounds to be investigated as PARP inhibitors. However, these molecules have a weak inhibitory activity and possess other effects unrelated to PARP inhibition. Thus, there is a need to provide potent inhibitors of the PARP enzyme.

US 2005/0234236 describes a process for the synthesis of pyridazinones, WO2004/085406 describes benzyl-pyridazinones as reverse transcriptase inhibitors and EP0810218 describes benzyl-pyridazinones as COX I and COX II inhibitors.

It has now surprisingly been discovered that pyridinone and pyridazinone derivatives of the present invention exhibit high levels of inhibition of the activity of PARP.

The compounds of this invention are useful in the inhibition of poly(ADP-ribose)polymerase (PARP). They are particularly useful as inhibitors of PARP-1 and/or PARP-2. The present invention provides the use of a compound of formula I:

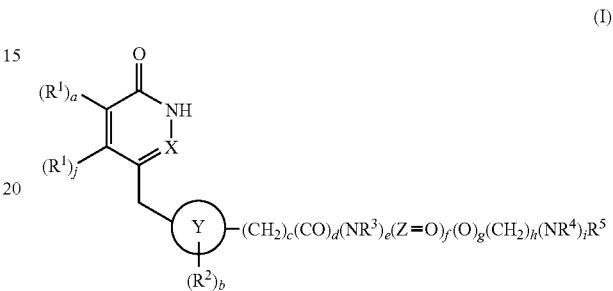

wherein:
a is 0 or 1;
b is 0, 1, 2 or 3;
c is 0, 1, 2, 3, 4, 5 or 6;
d is 0 or 1;
e is 0 or 1;
f is 0 or 1;
g is 0 or 1;
h is 0, 1, 2, 3, 4, 5 or 6;
i is 0 or 1;
j is 0 or 1;
X is N or CH;
Y is $C_{6-10}$aryl, a 5 membered unsaturated heterocycle containing 1, 2, 3 or 4 heteroatoms independently selected from O, N and S, but not more than one of which is O or S, or a 6 membered unsaturated heterocycle containing 1, 2, 3 or 4 nitrogen atoms;
Z is C or SO;
each $R^1$ is independently $C_{1-6}$alkyl, halo$C_{1-6}$alkyl, halogen or cyano;
each $R^2$ is independently hydroxy, halogen, cyano, nitro, $C_{1-6}$alkyl, halo$C_{1-6}$alkyl, $C_{1-6}$alkoxy, halo$C_{1-6}$alkoxy or $NR^aR^b$;
$R^3$ is hydrogen or $C_{1-6}$alkyl;
$R^4$ is hydrogen or $C_{1-6}$alkyl;
$R^5$ is hydrogen, hydroxy, cyano, oxo, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro or a ring which is: $C_{6-10}$aryl; $C_{6-10}$arylcarbonyl; $C_{3-10}$cycloalkyl; a 4 membered saturated heterocyclic ring containing one N atom; a 5 or 6 membered saturated or partially saturated heterocyclic ring containing one, two or three N atoms and zero or one O atom; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-15 membered unsaturated, partially saturated or saturated heterocyclic ring containing 1, 2, 3 or 4 heteroatoms independently selected from N, O and S; any of which rings being optionally substituted by one or more groups independently selected from $A-(CR^9R^{10})_qR^6$;

each A is independently a direct bond, O, C=O, (C=O)NR$^7$, NR$^7$(C=O), (C=O)O, O(C=O), (C=S)NR$^7$, NR$^7$ or S(O)$_r$;

each q is independently 0, 1, 2, 3, or 4;

r is 0, 1 or 2;

each R$^6$ is independently hydroxy, oxo, cyano, halogen, nitro, C$_{1-6}$alkyl, C$_{2-10}$alkenyl, haloC$_{1-6}$alkyl, NR$^a$R$^b$ or a ring which is: C$_{3-10}$cycloalkyl; C$_{6-10}$aryl; C$_{6-10}$aryloxy; a 4 membered saturated heterocyclic ring containing one N atom; a 5, 6 or 7 membered saturated or partially saturated heterocyclic ring containing one, two or three atoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one or more groups independently selected from R$^8$;

R$^7$ is hydrogen or R$^6$;

each R$^8$ is independently hydroxy, oxo, cyano, halogen, nitro, C$_{1-6}$alkyl, C$_{1-6}$alkoxy, C$_{2-10}$alkenyl, haloC$_{1-6}$alkyl, haloC$_{1-6}$alkoxy, —O(C=O)C$_{1-6}$alkyl, —(C=O)OC$_{1-6}$alkyl, NR$^a$R$^b$ or a ring which is: C$_{3-10}$cycloalkyl, C$_{6-10}$aryl, C$_{6-10}$arylC$_{1-6}$alkyl, C$_{6-10}$arylcarbonyl, C$_{6-10}$aryloxycarbonyl, C$_{6-10}$arylC$_{1-6}$alkoxycarbonyl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one or more groups independently selected from halogen, C$_{1-6}$alkyl or haloC$_{1-6}$alkyl;

each of R$^9$ and R$^{10}$ is independently hydrogen, halogen, C$_{1-6}$alkyl or haloC$_{1-6}$alkyl;

each of R$^a$ and R$^b$ is independently hydrogen, C$_{1-6}$alkyl, C$_{3-10}$cycloalkyl, C$_{3-10}$cycloalkylC$_{1-6}$alkyl, C$_{6-10}$aryl or C$_{6-10}$arylC$_{1-6}$alkyl;

or a pharmaceutically acceptable salt or tautomer thereof, for the manufacture of a medicament for the treatment or prevention of conditions which can be ameliorated by the inhibition of poly(ADP-ribose)polymerase (PARP).

The present invention also provides a method for the treatment or prevention of conditions which can be ameliorated by the inhibition of poly(ADP-ribose)polymerase (PARP), which method comprises administration to a patient in need thereof of an effective amount of a compound of formula I or a composition comprising a compound of formula I.

In an embodiment, the conditions which can be ameliorated by the inhibition of poly(ADP-ribose)polymerase (PARP) include inflammatory diseases; reperfusion injuries; ischemic conditions; stroke; chronic and acute renal failure; vascular diseases other than cardiovascular diseases; cardiovascular diseases; diabetes mellitus; cancer, particularly cancer which is deficient in Homologous Recombination (HR) dependent DNA DSB repair activity, for example BRCA-1 or BRCA-2 deficient tumors; neurodegenerative diseases; retroviral infections; retinal damage; skin senescence; UV-induced skin damage; and premature aging.

In an embodiment, the conditions which can be ameliorated by the inhibition of poly(ADP-ribose)polymerase (PARP) are selected from; reperfusion injuries; ischemic conditions; stroke; chronic and acute renal failure; vascular diseases other than cardiovascular diseases; cardiovascular diseases; diabetes mellitus; cancer, particularly cancer which is deficient in Homologous Recombination (HR) dependent DNA DSB repair activity, for example BRCA-1 or BRCA-2 deficient tumors; neurodegenerative diseases; retroviral infections; retinal damage; skin senescence; UV-induced skin damage; and premature aging.

In an embodiment of each of the above embodiments:

each R$^2$ is independently hydroxy, halogen, cyano, nitro, C$_{1-6}$alkyl, haloC$_{1-6}$alkyl, C$_{1-6}$alkoxy or haloC$_{1-6}$alkoxy;

R$^5$ is hydrogen, hydroxy, cyano, oxo, halogen, C$_{1-6}$alkyl, C$_{2-10}$alkenyl, haloC$_{1-6}$alkyl, hydroxyC$_{1-6}$alkyl, C$_{1-6}$alkylcarbonyl, C$_{1-6}$alkoxy, haloC$_{1-6}$alkoxy, C$_{1-6}$alkoxycarbonyl, carboxy, nitro or a ring which is: C$_{6-10}$aryl; C$_{6-10}$arylcarbonyl; C$_{3-10}$cycloalkyl; a 4 membered saturated heterocyclic ring containing one N atom; a 5, 6 or 7 membered saturated or partially saturated heterocyclic ring containing one, two or three N atoms and zero or one O atom; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one or more groups independently selected from A-(CH$_2$)$_q$R$^6$;

each R$^6$ is independently hydroxy, oxo, cyano, halogen, nitro, C$_{1-6}$alkyl, C$_{2-10}$alkenyl, haloC$_{1-6}$alkyl or a ring which is: C$_{6-10}$aryl; a 4 membered saturated heterocyclic ring containing one N atom; a 5, 6 or 7 membered saturated or partially saturated heterocyclic ring containing one, two or three N atoms and zero or one O atom; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one or more groups independently selected from R$^8$;

each R$^8$ is independently hydroxy, oxo, cyano, halogen, nitro, C$_{1-6}$alkyl, C$_{1-6}$alkoxy, C$_{2-10}$alkenyl, haloC$_{1-6}$alkyl, haloC$_{1-6}$alkoxy, —O(C=O)C$_{1-6}$alkyl, —(C=O)OC$_{1-6}$alkyl, amino, C$_{1-6}$alkylamino, di(C$_{1-6}$alkyl)amino, C$_{6-10}$aryl, a 5 membered heteroaromatic ring containing 1, 2, 3or 4 heteroatoms independently selected from N, O and S, not more than one heteroatom of which is O or S or a 6 membered heteroaromatic ring containing 1, 2 or 3 nitrogen atoms.

The present invention also provides novel compounds of formula I:

(I)

$(R^1)_a$ — [ring with O, NH, X] — $(R^1)_j$ — Y $(R^2)_b$ —(CH$_2$)$_c$(CO)$_d$(NR$^3$)$_e$(Z=O)$_f$(O)$_g$(CH$_2$)$_h$(NR$^4$)$_i$R$^5$ wherein:

a, b, c, d, e, f, g, h, i, j, X, Y, Z, R$^1$, R$^2$, R$^3$, R$^4$ and R$^5$ are as defined above;

provided that:

(a) when $(CH_2)_c(CO)_d(NR^3)_e(Z=O)_f(O)_g(CH_2)_h(NR^4)_i$ represents an O linker, $R^2$ is fluoro, X is N and Y is phenyl then $R^5$ is not an optionally substituted ring selected from $C_{6-10}$aryl, a 5 membered heteroaromatic ring, a 6 membered heteroaromatic ring or a 7-15 membered unsaturated or partially saturated heterocyclic ring;

(b) when X is N and Y is phenyl, napthyl or a 9 or 10 membered unsaturated or partially saturated heterocyclic ring containing 1 or 2 heteroatoms selected from N, O and S, then $R^5$ is not $C_{1-6}$alkyl, halo$C_{1-6}$alkyl, hydroxy$C_{1-6}$alkyl, $C_{1-6}$alkoxy, halo$C_{1-6}$alkoxy, $C_{1-6}$alkylcarbonyl or an optionally substituted $C_{3-10}$cycloalkyl, phenyl, napthyl, pyridinyl, pyridine N-oxide, indole, indole N-oxide, quinoline, quinoline N-oxide, pyrimidinyl, pyrazinyl or pyrrolyl; and (c) when $(CH_2)_c(CO)_d(NR^3)_e(Z=O)_f(O)_g(CH_2)_h(NR^4)_i$ represents a CO linker, X is N and Y is phenyl then $R^5$ is not an optionally substituted phenyl, pyridinyl, thienyl or furyl;

or a pharmaceutically acceptable salt or tautomer thereof.

In an embodiment:

(a) when $(CH_2)_c(CO)_d(NR^3)_e(Z=O)_f(O)_g(CH_2)_h(NR^4)_i$ represents an O linker, $R^2$ is fluoro, X is N and Y is phenyl then $R^5$ is not an optionally substituted ring selected from $C_{6-10}$aryl, a 5 membered heteroaromatic ring, a 6 membered heteroaromatic ring or a 7-10 membered unsaturated or partially saturated heterocyclic ring;

(b) when X is N and Y is phenyl, napthyl or a 9 or 10 membered unsaturated or partially saturated heterocyclic ring containing 1 or 2 heteroatoms selected from N, O and S, then $R^5$ is not $C_{1-6}$alkyl, halo$C_{1-6}$alkyl, hydroxy$C_{1-6}$alkyl or an optionally substituted $C_{3-10}$cycloalkyl, phenyl, napthyl, pyridinyl, pyridine N-oxide, indole, indole N-oxide, quinoline, quinoline N-oxide, pyrimidinyl, pyrazinyl or pyrrolyl; and (c) when $(CH_2)_c(CO)_d(NR^3)_e(Z=O)_f(O)_g(CH_2)_h(NR^4)_i$ represents a CO linker, X is N and Y is phenyl then $R^5$ is not an optionally substituted phenyl, pyridinyl, thienyl or furyl.

In an embodiment the sum of a and j is 1 or 2.

In an embodiment b is 0 or 1. In another embodiment b is 1.

In an embodiment c is 0.
In an embodiment d is 1.
In an embodiment e is 0.
In an embodiment f is 0.
In an embodiment g is 0.
In an embodiment h is 0.
In an embodiment i is 0.
In an embodiment j is 0. In another embodiment j is 1.
In an embodiment X is N. In another embodiment X is CH.
In an embodiment Y is phenyl, pyridinyl, pyrimidinyl, furanyl or thienyl.
In another embodiment Y is $C_{6-10}$aryl.
A particular Y group is phenyl.

In an embodiment $R^1$ is fluoro$C_{1-3}$alkyl, halogen or $C_{1-6}$alkyl. In another embodiment $R^1$ is $C_{1-6}$alkyl.

A particular $R^1$ group is ethyl. Further particular $R^1$ groups are methyl and isopropyl.

In an embodiment $R^2$ is halogen, $C_{1-6}$alkoxy, amino, $C_{1-6}$alkylamino or di($C_{1-6}$alkyl)amino.

In another embodiment $R^2$ is fluoro$C_{1-3}$alkyl or halogen.
In another embodiment $R^2$ is halogen, for example fluorine or chlorine.

A particular $R^2$ group is fluorine. Further particular $R^2$ groups are dimethylamino, isopropoxy and methoxy.

In an embodiment $R^5$ is hydrogen, hydroxy, cyano, halogen, $C_{2-10}$alkenyl, $C_{1-6}$alkylcarbonyl, $C_{1-6}$alkoxy, $C_{1-6}$alkoxycarbonyl, carboxy, nitro or a ring which is: a 4 membered saturated heterocyclic ring containing one N atom; or a 5, 6 or 7 membered saturated or partially saturated heterocyclic ring containing one, two or three N atoms and zero or one O atom; any of which rings being optionally substituted by one or more groups independently selected from A-$(CH_2)_qR^6$.

In another embodiment $R^5$ is a 4 membered saturated heterocyclic ring containing one N atom, a 5 or 6 membered saturated or partially saturated heterocyclic ring containing one, two or three N atoms and zero or one O atom or a 7-15 membered unsaturated, partially saturated or saturated heterocyclic ring containing 1, 2, 3 or 4 heteroatoms independently selected from N, O and S; any of which rings being optionally substituted by one or more groups independently selected from A-$(CR^9R^{10})_qR^6$.

In another embodiment $R^5$ is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S; any of which rings being optionally substituted by one or more groups independently selected from A-$(CR^9R^{10})_qR^6$.

In another embodiment, $R^5$ is a 4 membered saturated heterocyclic ring containing one N atom or a 5, 6 or 7 membered saturated or partially saturated heterocyclic ring containing one, two or three N atoms and zero or one O atom; any of which rings being optionally substituted by one or more groups independently selected from A-$(CH_2)_qR^6$.

In an embodiment $R^5$ is diazepanyl, piperidinyl, piperazinyl, pyrrolidinyl, spirobenzofuranpiperidinyl, tetrahydroimidazopyrazinyl, tetrahydrotriazolopyrazinyl, diazaspirodecanyl, tetrahydropyrazolopyridinyl, diazaspirononanyl, imidazolidinyl, azetidinyl or tetrahydrotriazolopyridinyl; any of which rings being optionally substituted by one or more groups independently selected from A-$(CR^9R^{10})_qR^6$.

In an embodiment, when $R^5$ is a ring it is optionally substituted by one, two or three independently selected A-$(CR^9R^{10})_qR^6$ groups. In an embodiment, when $R^5$ is a ring it is unsubstituted or monosubstituted.

In an embodiment, when $R^6$ is a ring it is optionally substituted by one, two or three groups independently selected from $R^8$. In another embodiment, when $R^6$ is a ring it is unsubstituted, monosubstituted or disubstituted.

In an embodiment, when $R^8$ is a ring it is optionally substituted by one, two or three groups independently selected groups. In another embodiment, when $R^8$ is a ring it is unsubstituted, monosubstituted or disubstituted.

In an embodiment $R^7$ is hydrogen.

In an embodiment A is a direct bond, O, CO or NH.

In another embodiment A is a direct bond, CO or NH. In another embodiment A is a direct bond or carbonyl. A particular A group is CO.

In an embodiment q is 0, 1 or 2. In another embodiment q is 0.

In an embodiment $R^6$ is oxo, $C_{1-6}$alkyl, halo $C_{1-6}$alkyl, amino, $C_{1-6}$alkylamino, (di$C_{1-6}$alkyl)amino or a ring which is pyrimidinyl, pyridinyl, pyrazolyl, phenyl, pyrazinyl, tetrahydroisoquinolinyl, cyclopentyl, tetrahydrofuranyl, pyrrolidinyl, piperidinyl, quinazolinyl, phenoxy, furyl, benzodioxolyl, thienyl, cyclopropyl or azetidinyl; any of which rings being optionally substituted by one or more groups independently selected from $R^8$.

In another embodiment $R^6$ is $C_{1-6}$alkyl.

In an embodiment $R^8$ is cyano, halogen, $C_{1-6}$alkyl, halo$C_{1-6}$ alkyl, $C_{1-6}$alkoxy, amino, $C_{1-6}$alkylamino, di($C_{1-6}$alkyl)amino, ($C_{3-10}$cycloalkyl$C_{1-6}$alkyl)amino, $C_{6-10}$arylamino, ($C_{6-10}$aryl$C_{1-6}$alkyl)amino or a ring which is $C_{6-10}$aryl, $C_{6-10}$aryl$C_{1-6}$alkyl, $C_{6-10}$arylcarbonyl, $C_{6-10}$aryloxycarbonyl or $C_{6-10}$aryl$C_{1-6}$alkoxycarbonyl; any of which rings being optionally substituted by one or more groups independently selected from halogen and $C_{1-6}$alkyl.

Particular $R^8$ groups include methoxy, chloro, methyl, trifluoromethyl, fluoro, cyano, methylamino, propyl, dimethylamino, benzyl, benzoxycarbonyl, phenylamino, amino, benzylamino, (cyclopropylmethyl)amino, isobutylamino, fluorobenzyl, methylbenzyl, naphthylmethyl and ethyl.

In an embodiment each of $R^9$ and $R^{10}$ is independently hydrogen, methyl, fluorine or trifluoromethyl.

In another embodiment each of $R^9$ and $R^{10}$ is hydrogen.

A particular $R^6$ group is methyl. Further specific $R^6$ groups include pyrimidinyl, pyridinyl, methoxypyridinyl, dimethylamino, pyrazolyl, chloropyridinyl, phenyl, dimethylpyrazinyl, methoxyphenyl, tetrahydroisoquinolinyl, cyclopentyl, trifluoromethyl, methylamino, difluoromethyl, isopropyl, tetrahydrofuranyl, pyrrolidinyl, piperidinyl, quinazolinyl, methylphenyl, (trifluoromethyl)phenyl, fluorophenoxy, cyanopyridinyl, difluorophenyl, furyl, methylpyrrolidinyl, benzodioxolyl, thienyl, cyclopropyl, oxo, difluoroazetidinyl, (methylamino)cyclopentyl, propylpyrrolidinyl, methylpiperidinyl, (dimethylamino)cyclopropyl, benzylpyrrolidinyl, (methylamino)cyclopropyl, methylazetidinyl, benzoxycarbonyl)methylpiperidinyl, (phenylamino)cyclopentyl, aminocyclopentyl, (benzylamino)cyclopentyl, [(cyclopropylmethyl)amino]cyclopentyl, (isobutylamino)cyclopentyl, (fluorobenzyl)pyrrolidinyl, (methylbenzyl)pyrrolidinyl, (naphthylmethyl)pyrrolidinyl and ethylpyrrolidinyl.

Thus, particular $R^5$ groups are diazepanyl and acetyldiazepanyl. Further particular $R^5$ groups are pyrimidinyldiazepanyl, pyridinylpiperidinyl, [(pyridinylmethyl)oxy]piperidinyl, (methoxypyridinyl)piperazinyl, pyridinylpyrrolidinyl, [(dimethylamino)methyl]piperidinyl, spirobenzofuranpiperidinyl, (pyrazolylethyl)piperidinyl, (chloropyridinyl)piperazinyl, benzyltetrahydroimidazopyrazinyl, (dimethylpyrazinyl)piperazinyl, phenyltetrahydroimidazopyrazinyl, (methoxybenzyl)piperazinyl, tetrahydroisoquinolinylpiperidinyl, piperazinyl, phenylpiperazinyl, benzylpiperazinyl, (pyridinylmethyl)piperazinyl, (cyclopentylcarbonyl)diazepanyl, (trifluoromethyl)tetrahydrotriazolopyrazinyl, propionylpiperazinyl, [(methyl)(methylamino)propanoyl]piperazinyl, (difluoroacetyl)piperazinyl, (trifluoropropanoyl)piperazinyl, isobutyrylpiperazinyl, (pyridinylcarbonyl)piperazinyl, (tetrahydrofuranylcarbonyl)piperazinyl, [(methyl)(dimethylamino)propanoyl]piperazinyl, (pentafluoropropanoyl)piperazinyl, (pyrrolidinylcarbonyl)piperazinyl, (trifluoroacetyl)piperazinyl, piperidinylpiperidinyl, pyrrolidinylpiperidinyl, quinazolinylpiperazinyl, pyrimidinylpiperazinyl, diazaspirodecanyl, (methylphenyl)tetrahydrotriazolopyrazinyl, [(trifluoromethyl)phenyl]tetrahydrotriazolopyrazinyl, [(fluorophenoxy)methyl]tetrahydrotriazolopyrazinyl, (cyanopyridinyl)piperazinyl, (methyl)diazaspirodecanyl, (difluorophenyl)tetrahydrotriazolopyrazinyl, [(dimethylamino)methyl]tetrahydrotriazolopyrazinyl, furyltetrahydrotriazolopyrazinyl, (pentafluoroethyl)tetrahydrotriazolopyrazinyl, {[(trifluoromethyl)phenyl]amino}tetrahydrotriazolopyrazinyl, (methylprolyl)piperazinyl, phenyltetrahydrotriazolopyrazinyl, benzodioxolyltetrahydrotriazolopyrazinyl, thienyltetrahydrotriazolopyrazinyl, cyclopropyltetrahydropyrazolopyridinyl, (trifluoromethyl)tetrahydropyrazolopyridinyl, pyridinyltetrahydrotriazolopyrazinyl, diazaspirononanyl, methyldioximidazolidinyl, (pyrrolidinylmethyl)azetidinyl, (difluoroazetidinyl)piperidinyl, (trifluoroethyl)tetrahydrotriazolopyridinyl, {[(methylamino)cyclopentyl]carbonyl}piperazinyl, methyldiazaspirononanyl, [(propylpyrrolidinyl)carbonyl]piperazinyl, (piperidinylcarbonyl)piperazinyl, [(methylpiperidinyl)carbonyl]piperazinyl, {[(dimethylamino)cyclopropyl]carbonyl}piperidinyl, [(dimethylamino)propanoyl]piperidinyl, [(benzylpyrrolidinyl)carbonyl]piperazinyl, (pyrrolidinylcarbonyl)piperazinyl, {[(methylamino)cyclopropyl]carbonyl}piperazinyl, [(methylazetidinyl)carbonyl]piperazinyl, [(methylpyrrolidinyl)carbonyl]piperidinyl, [(dimethylamino)trifluoropropanonyl]piperazinyl, [(methylpiperidinyl)carbonyl]piperidinyl, {[(benzoxycarbonyl)methylpiperidinyl]carbonyl}piperidinyl, [(dimethylamino)methylethyl]tetrahydrotriazolopyrazinyl, (trifluoroethyl)tetrahydrotriazolopyridinyl, [(pyrrolidinyl)acetyl]piperidinyl, ethyldiazaspirodecanyl, (cyclopropylmethyl)diazaspirodecanyl, [(anilinocyclopentyl)carbonyl]piperazinyl, [(aminocyclopentyl)carbonyl]piperazinyl, {[(benzylamino)cyclopentyl]carbonyl}piperazinyl, ({[(cyclopropylmethyl)amino]cyclopentyl}carbonyl)piperazinyl, {[(isobutylamino)cyclopentyl]carbonyl}piperazinyl, [(fluorobenzyl)prolyl]piperazinyl, [(methylbenzyl)prolyl]piperazinyl, [(naphthylmethyl)prolyl]piperazinyl and (ethylprolyl)piperazinyl.

Specific $R^5$ groups are 1,4-diazepan-1-yl and 4-acetyl-1,4-diazepan-1-yl. Further specific $R^5$ groups are 4-(pyrimidin-2-yl)-1,4-diazepan-1-y-l, 4-(pyridin-4-yl)piperidin-1-yl, 4-[(pyridin-2-ylmethyl)oxy]piperidin-1-yl, 3-[(pyridin-2-yl-methyl)oxy]piperidin-1-yl, 4-(5-methoxypyridin-2-yl)piperazin-1-yl, 4-(4-methoxypyridin-2-yl)piperazin-1-yl, 3-pyridin-4-ylpyrrolidin-1-yl, 3-[(dimethylamino)methyl]piperidin-1-yl, 1'H-spiro[1-benzofuran-3,4'-piperidin]-1'-yl, 4-(1H-pyrazol-1-ylethyl)piperidin-1-yl, 4-(5-chloropyridin-2-yl)piperazin-1-yl, 4-(6-methoxypyridin-2-yl)piperazin-1-yl, 3-benzyl-5,6,7,8-tetrahydroimidazo[1,2-a]pyrazin-7-yl, 4-(3,6-dimethylpyrazin-2-yl)piperazin-1-yl, 3-phenyl-5,6,7,8-tetrahydroimidazo[1,2-a]pyrazin-7-yl, 4-(3-methoxybenzyl)piperazin-1-yl, 4-(1,2,3,4-tetrahydroisoquinolin-2-yl)piperidin-1-yl, 2-phenylpiperazin-1-yl, piperazin-1-yl, 2-benzylpiperazin-1-yl, 3-(pyridin-3-ylmethyl)piperazin-1-yl, 4-(cyclopentylcarbonyl)-1,4-diazepan-1-yl, 3-(trifluoromethyl)-5,6-dihydro[1,2,4]triazolo[4,3-a]pyrazin-7(8H)-yl, 4-propionylpiperazin-1-yl, 4-[2-methyl-2-(methylamino) propanoyl]piperazin-1-yl, 4-(difluoroacetyl)piperazin-1-yl, 4-(3,3,3-trifluoropropanoyl)piperazin-1-yl, 4-isobutyrylpiperazin-1-yl, 4-(pyridin-2-ylcarbonyl)piperazin-1-yl, 4-(tetrahydrofuran-2-ylcarbonyl)piperazin-1-yl, 4-[2-methyl-2-(dimethylamino)propanoyl]piperazin-1-yl, 4-(2,2,3,3,3-pentafluoropropanoyl)piperazin-1-yl, 4-(pyrrolidin-1-ylcarbonyl)piperazin-1-yl, 4-(trifluoroacetyl)piperazin-1-yl, 4-(piperidin-1-yl)piperidin-1-yl, 4-(pyrrolidin-1-yl)piperidin-1-yl, 4-(quinazolin-4-yl)piperazin-1-yl, 4-(pyrimidin-2-yl)piperazin-1-yl, 8-aza-1-azoniaspiro[4.5]decan-8-yl, 3-(3-methylphenyl)-5,6,7,8-tetrahydro[1,2,4]triazolo[4,3-a]pyrazin-7-yl, 3-[4-(trifluoromethyl)phenyl]-5,6,7,8-tetrahydro[1,2,4]triazolo[4,3-a]pyrazin-7-yl, 3-[(4-fluorophenoxy)methyl]-5,6,7,8-tetrahydro[1,2,4]triazolo[4,3-a]pyrazin-7-yl, 4-(3-cyanopyridin-2-yl)piperazin-1-yl, 1-methyl-8-aza-1-azoniaspiro[4.5]decan-8-yl, 3-(3,5-difluorophenyl)-5,6,7,8-tetrahydro[1,2,4]triazolo[4,3-a]pyrazin-7-yl, 3-[(dimethylamino)methyl]-5,6,7,8-tetrahydro[1,2,4]

triazolo[4,3-a]pyrazin-7-yl, 3-(2-furyl)-5,6,7,8-tetrahydro[1,2,4]triazolo[4,3-a]pyrazin-7-yl, 3-(pentafluoroethyl)-5,6,7,8-tetrahydro[1,2,4]triazolo[4,3-a]pyrazin-7-yl, 3-{[(trifluoromethyl)phenyl]amino}-5,6,7,8-tetrahydro[1,2,4]triazolo[4,3-a]pyrazin-7-yl, 4-(2-methylprolyl)piperazin-1-yl, 3-phenyl-5,6,7,8-tetrahydro[1,2,4]triazolo[4,3-a]pyrazin-7-yl, 3-(1,3-benzodioxol-5-yl)-5,6,7,8-tetrahydro[1,2,4]triazolo[4,3-a]pyrazin-7-yl, 3-(2-thienyl)-5,6,7,8-tetrahydro[1,2,4]triazolo[4,3-a]pyrazin-7-yl, 3-cyclopropyl-4,5,6,7-tetrahydro-1H-pyrazolo[3,4-c]pyridin-6-yl, 3-(trifluoromethyl)-4,5,6,7-tetrahydro-1H-pyrazolo[3,4-c]pyridin-6-yl, 3-(trifluoromethyl)-4,5,6,7-tetrahydro-1H-pyrazolo[4,3-c]pyridin-5-yl, 3-pyridin-3-yl-5,6,7,8-tetrahydro[1,2,4]triazolo[4,3-a]pyrazin-7-yl, 7-aza-1-azoniaspiro[3.5]nonan-7-yl, 4-methyl-2,5-dioxoimidazolidin-1-yl, 3-(pyrrolidin-1-ylmethyl)azetidin-1-yl, 4-(3,3-difluoroazetidin-1-yl)piperidin-1-yl, 1-(2,2,2-trifluoroethyl)-4,5,6,7-tetrahydro-1H-[1,2,3]triazolo[4,5-c]pyridin-5-yl, 4-{[1-(methylamino)cyclopentyl]carbonyl}piperazin-1-yl, 1-methyl-7-aza-1-azoniaspiro[3.5]nonan-7-yl, 8-aza-2-azoniaspiro[4.5]decan-8-yl, 4-[(2-propylpyrrolidin-2-yl)carbonyl]piperazin-1-yl, 2-methyl-8-aza-2-azoniaspiro[4.5]decan-8-yl, 4-(piperidin-3-ylcarbonyl)piperazin-1-yl, 4-[(1-methypiperidin-3-yl)carbonyl]piperazin-1-yl, 4-{[1-(dimethylamino)cyclopropyl]carbonyl}piperidin-1-yl, 4-[3-(dimethylamino)propanoyl]piperidin-1-yl, 4-[(2-benzylpyrrolidin-2-yl)carbonyl]piperazin-1-yl, 4-(pyrrolidin-3-ylcarbonyl)piperazin-1-yl, 4-{[1-(methylamino)cyclopropyl]carbonyl}piperazin-1-yl, 4-[(2-methylazetidin-2-yl)carbonyl]piperazin-1-yl, 4-[(1-methylpyrrolidin-3-yl)carbonyl]piperidin-1-yl, 4-[2-(dimethylamino)-3,3,3-trifluoropropanoyl]piperazin-1-yl, 4-[(2-methylpiperidin-2-yl)carbonyl]piperidin-1-yl, 4-{[1-(benzoxycarbonyl)-2-methylpiperidin-2-yl]carbonyl}piperidin-1-yl, 3-[1-(dimethylamino)-1-methylethyl]-5,6-dihydro[1,2,4]triazolo[4,3-a]pyrazin-7(8H)-yl, 1-(2,2,2-trifluoroethyl)-1,4,6,7-tetrahydro-5H-[1,2,3]triazolo[4,5-c]pyridin-5-yl, 4-[(2S)-pyrrolidin-2-ylacetyl]piperidin-1-yl, 1-ethyl-8-aza-1-azoniaspiro[4.5]decan-8-yl, 1-(cyclopropylmethyl)-8-aza-1-azoniaspiro[4.5]decan-8-yl, 4-[(1-anilinocyclopentyl)carbonyl]piperazin-1-yl, 4-[(1-aminocyclopentyl)carbonyl]piperazin-1-yl, 4-{[1-(benzylamino)cyclopentyl]carbonyl}piperazin-1-yl, 4-({1-[(cyclopropylmethyl)amino]cyclopentyl}carbonyl)piperazin-1-yl, 4-{[1-(isobutylamino)cyclopentyl]carbonyl}piperazin-1-yl, 4-[2-(4-fluorobenzyl)prolyl]piperazin-1-yl, 4-[2-(4-methylbenzyl)prolyl]piperazin-1-yl, 4-[2-(naphthylmethyl)prolyl]piperazin-1-yl and 4-(2-ethylprolyl)piperazin-1-yl.

In an embodiment each of $R^a$ and $R^b$ is independently hydrogen, methyl, phenyl, benzyl or cyclopropylmethyl.

In another embodiment each of $R^a$ and $R^b$ is independently hydrogen or $C_{1-6}$alkyl, for example methyl.

The present invention also provides compounds of formula II:

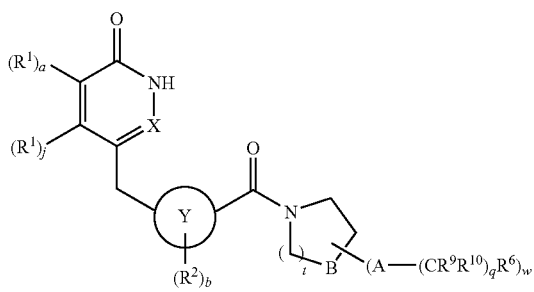

(II)

wherein:
a, b, j, q, A, X, Y, $R^1$, $R^2$, $R^6$, $R^9$ and $R^{10}$ are as defined above;
t is 0, 1, 2 or 3;
when t is 0 then B is $CH_2$;
when t is 1, 2 or 3 then B is $CH_2$, NH or O;
w is 0, 1, 2 or 3;
or a pharmaceutically acceptable salt or tautomer thereof.
For the avoidance of doubt, $A-(CR^9R^{10})_qR^6$ may be attached to the B containing ring at any substitutable position.

The preferred identities with reference to formula II are as defined previously for formula I mutatis mutandis.

In an embodiment each of $R^9$ and $R^{10}$ is hydrogen.
In an embodiment t is 3.
In an embodiment B is NH.
In an embodiment w is 0.

The present invention also provides compounds of formula III

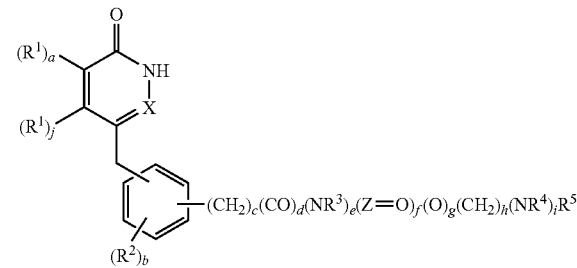

(III)

wherein:
a, b, c, d, e, f, g, h, i, j, X, Y, Z, $R^1$, $R^2$, $R^3$, $R^4$ and $R^5$ are as defined above;
provided that:
(a) when $(CH_2)_c(CO)_d(NR^3)_e(Z=O)_f(O)_g(CH_2)_h(NR^4)_i$ represents an O linker, $R^2$ is fluoro and X is N then $R^5$ is not an optionally substituted ring selected from $C_{6-10}$aryl, a 5 membered heteroaromatic ring, a 6 membered heteroaromatic ring or a 7-15 membered unsaturated or partially saturated heterocyclic ring;
(b) when X is N then $R^5$ is not $C_{1-6}$alkyl, halo$C_{1-6}$alkyl, hydroxy$C_{1-6}$alkyl, $C_{1-6}$alkoxy, halo$C_{1-6}$alkoxy, $C_{1-6}$alkylcarbonyl or an optionally substituted $C_{3-10}$cycloalkyl, phenyl, napthyl, pyridinyl, pyridine N-oxide, indole, indole N-oxide, quinoline, quinoline N-oxide, pyrimidinyl, pyrazinyl or pyrrolyl; and
(c) when $(CH_2)_c(CO)_d(NR^3)_e(Z=O)_f(O)_g(CH_2)_h(NR^4)_i$ represents a CO linker and X is N then $R^5$ is not an optionally substituted phenyl, pyridinyl, thienyl or furyl;
or a pharmaceutically acceptable salt or tautomer thereof.

The present invention also provides compounds formula IV:

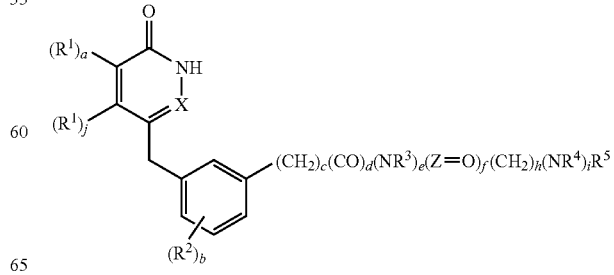

(IV)

wherein:

a, b, c, d, e, f, h, i, j, X, Y, Z, $R^1$, $R^2$, $R^3$ and $R^4$ are as defined above;

$R^5$ is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S; any of which rings being optionally substituted by one or more groups independently selected from A-$(CR^9R^{10})_qR^6$; or a pharmaceutically acceptable salt or tautomer thereof.

The present invention also provides compounds formula V:

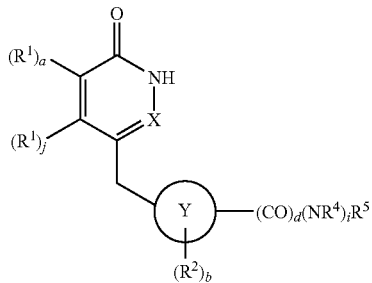

(V)

wherein:

a, b, d, i, j, X, Y, $R^1$, $R^2$, $R^4$ and $R^5$ are as defined above; provided that:

(a) when X is N then $R^5$ is not $C_{1-6}$alkyl, halo$C_{1-6}$alkyl, hydroxy$C_{1-6}$alkyl, $C_{1-6}$alkoxy, halo$C_{1-6}$alkoxy, $C_{1-6}$alkylcarbonyl or an optionally substituted $C_{3-10}$cycloalkyl, phenyl, napthyl, pyridinyl, pyridine N-oxide, indole, indole N-oxide, quinoline, quinoline N-oxide, pyrimidinyl, pyrazinyl or pyrrolyl; and (b) when d is 1, i is 0 and X is N then $R^5$ is not an optionally substituted phenyl, pyridinyl, thienyl or furyl;

or a pharmaceutically acceptable salt or tautomer thereof.

The present invention also provides novel compounds of formula VI:

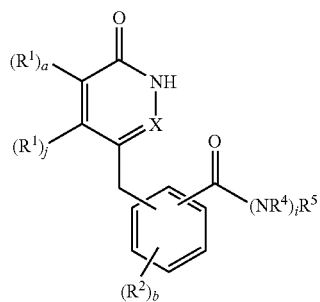

(VI)

wherein:

a, b, c, d, e, f, h, i, j, X, Y, Z, $R^1$, $R^2$, $R^3$ and $R^4$ are as defined above;

$R^5$ is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S; any of which rings being optionally substituted by one or more groups independently selected from A-$(CR^9R^{10})_qR^6$;

or a pharmaceutically acceptable salt or tautomer thereof.

The present invention also provides compounds of formula VII:

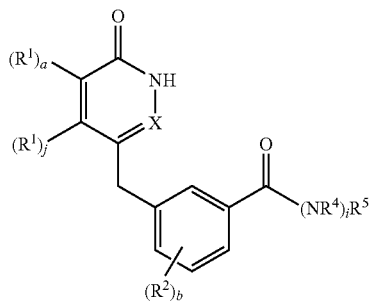

(VII)

wherein:

a, b, j, i, X, $R^1$, $R^2$, and $R^4$ are as defined above;

$R^5$ is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S; any of which rings being optionally substituted by one or more groups independently selected from A-$(CR^9R^{10})_qR^6$;

or a pharmaceutically acceptable salt or tautomer thereof.

The present invention also provides compounds of formula VIII:

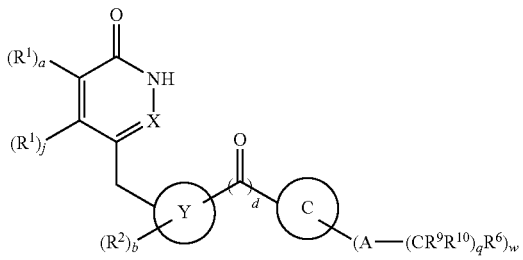

(VIII)

wherein:

a, b, d, Y, $R^1$ and $R^2$ are as defined above;

C is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S;

or a pharmaceutically acceptable salt or tautomer thereof.

The present invention also provides compounds of formula IX:

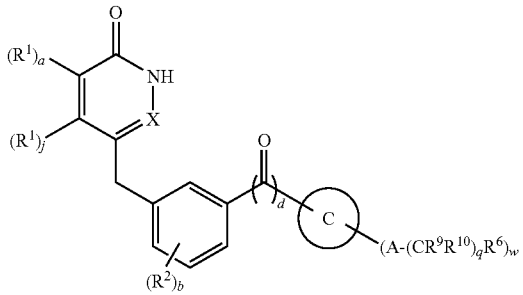

(IX)

wherein:

a, b, d, q, j, A, $R^1$, $R^2$, $R^6$, $R^9$, $R^{10}$ are as defined above;

C is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S;

or a pharmaceutically acceptable salt or tautomer thereof.

Particular C groups are diazepanyl, piperidinyl, piperazinyl, pyrrolidinyl, spirobenzofuranpiperidinyl, tetrahydroimidazopyrazinyl, tetrahydrotriazolopyrazinyl, diazaspirodecanyl, tetrahydropyrazolopyridinyl, diazaspirononanyl, imidazolidinyl, azetidinyl or tetrahydrotriazolopyridinyl.

In an embodiment of compounds of any one of formulae II to XI, X is N.

In an embodiment of compounds of any one of formulae II to XI, b is 0 or 1 and $R^2$ is fluorine.

In an embodiment of compounds of formulae II, X and XI, w is 0 or 1.

The preferred identities with reference to formula III, IV, V, VI, VII and VIII are as defined previously for formula I and II mutatis mutandis.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

The compounds disclosed herein may exist as tautomers and both tautomeric forms are intended to be encompassed by the scope of the invention, even though only one tautomeric structure may be depicted. For example, compounds of formula I may tautomerise into compounds of the following structure:

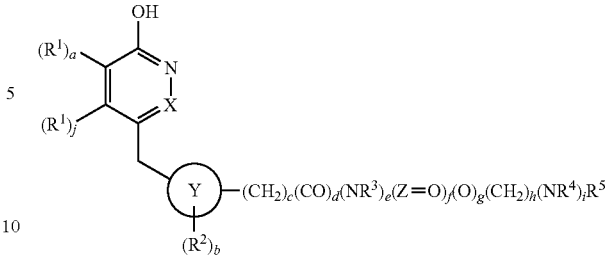

The compounds may exist in different isomeric forms, all of which are encompassed by the present invention.

The compounds may exist in a number of different polymorphic forms.

When any variable (e.g. $R^1$ and $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched, straight-chain and cyclic saturated aliphatic hydrocarbon groups having the specified number of carbon atoms. For example, "$C_{1-6}$alkyl" is defined to include groups having 1, 2, 3, 4, 5 or 6 carbons in a linear, branched or cyclic arrangement. For example, "$C_{1-6}$alkyl" specifically includes methyl, ethyl, n-propyl, i-propyl, n-butyl, t-butyl, i-butyl, pentyl, hexyl, cyclopropyl, cyclobutyl, cyclopentyl and cyclohexyl and so on. Preferred alkyl groups are methyl and ethyl. The term "cycloalkyl" means a monocyclic, bicyclic or polycyclic saturated aliphatic hydrocarbon group having the specified number of carbon atoms. For example, "$C_{3-7}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy, t-butoxy, cyclopropyloxy, cyclobutyloxy and cyclopentyloxy. The preferred alkoxy groups are methoxy and ethoxy. The term '$C_{6-10}$aryloxy' can be construed in an analogous manner. A preferred such group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-6}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

As used herein, the term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term "$C_{6-10}$arylcarbonyl" can be construed in an analogous manner.

The rings present in the compounds of this invention may be monocyclic or multicyclic, particularly bicyclic. The multicyclic rings may be fused, bridged or spiro linked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

7-15 membered heterocycles include 7, 8, 9, 10, 11, 12, 13, 14 and 15 membered heterocycles.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, diazepanyl and N-oxides thereof. Further examples include spirobenzofuranpiperidinyl, tetrahydrotriazolopyrazinyl, diazaspirodecanyl, tetrahydropyrazolopyridinyl, diazaspirononanyl, and tetrahydrotriazolopyridinyl.

A preferred 4 membered saturated heterocycle is azetidinyl. Attachment of a heterocyclyl substituent can occur via a carbon atom or via a heteroatom.

Preferred 5, 6 or 7 membered saturated or partially saturated heterocycles are pyrrolidinyl, piperidinyl, piperazinyl, morpholinyl, tetrahydrofuran, thiomorpholinyl and diazepanyl. A further preferred ring is imidazolidinyl Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteroaromatic rings are pyridinyl, pyrimidinyl, pyridazinyl and pyrazinyl.

Preferred 7-10 membered partially saturated or unsaturated heterocyclic rings are tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl and indolizinyl. Further 7-15 membered unsaturated, partially saturated or saturated heterocyclic rings include spirobenzofuranpiperidinyl, tetrahydrotriazolopyrazinyl, diazaspirodecanyl, tetrahydropyrazolopyridinyl, diazaspirononanyl, and tetrahydrotriazolopyridinyl.

As used herein, the term "halogen" refers to fluorine, chlorine, bromine and iodine, of which fluorine and chlorine are preferred.

Particular compounds within the scope of the present invention are:

4-{5-[(5-Ethyl-6-oxo-1,6-dihydropyridazin-3-yl)methyl]-2-fluorobenzoyl}-1,4-diazepan-1-ium trifluoroacetate;
4-{5-[(4-Ethyl-6-oxo-1,6-dihydropyridazin-3-yl)methyl]-2-fluorobenzoyl}-1,4-diazepan-1-ium trifluoroacetate;
6-{3-[(4-Acetyl-1,4-diazepan-1-yl)carbonyl]-4-fluorobenzyl}-4-ethylpyridazin-3(2H)-one;
1-Acetyl-4-{5-[(6-chloro-4-ethylpyridazin-3-yl)methyl]-2-fluorobenzoyl}-1,4-diazepane;

and pharmaceutically acceptable salts, free bases and tautomers thereof.

Further particular compounds within the scope of the present invention are:

4-Ethyl-6-(4-fluoro-3-{[3-(trifluoromethyl)-5,6-dihydro[1,2,4]friazolo[4,3-a]pyrazin-7(8H)-yl]carbonyl}benzyl)pyridazin-3(2H)-one;
4-{5-[(5-Ethyl-4-methyl-6-oxo-1,6-dihydropyridazin-3-yl)methyl]-2-fluorobenzoyl}-1,4-diazepan-1-ium trifluoroacetate;
4-{5-[(4-ethyl-5-methyl-6-oxo-1,6-dihydropyridazin-3-yl)methyl]-2-fluorobenzoyl}-1,4-diazepan-1-ium trifluoroacetate;
4-{2-Fluoro-5-[(5-isopropyl-6-oxo-1,6-dihydropyridazin-3-yl)methyl]benzoyl}-1,4-diazepan-1-ium trifluoroacetate;
4-{5-[(4,5-Dimethyl-6-oxo-1,6-dihydropyridazin-3-yl)methyl]-2-fluorobenzoyl}-1,4-diazepan-1-ium trifluoroacetate;
1-(4-{5-[(4,5-Dimethyl-6-oxo-1,6-dihydropyridazin-3-yl)methyl]-2-fluorobenzoyl}piperazin-1-yl)-N,2-dimethyl-1-oxopropan-2-aminium trifluoroacetate;
8-{5-[(4,5-Dimethyl-6-oxo-1,6-dihydropyridazin-3-yl)methyl]-2-fluorobenzoyl}-8-aza-1-azoniaspiro[4.5]decane trifluoroacetate;
8-{5-[(4,5-Dimethyl-6-oxo-1,6-dihydropyridazin-2-ium-3-yl)methyl]-2-fluorobenzoyl}-1-methyl-8-aza-1-azoniaspiro[4.5]decane bis(trifluoroacetate);
4-[(4,5-Dimethyl-6-oxo-1,6-dihydropyridazin-3-yl)methyl]-N,N-dimethyl-2-{[3-(trifluoromethyl)-5,6-dihydro[1,2,4]friazolo[4,3-a]pyrazin-7(8H)-yl]carbonyl}benzenaminium trifluoroacetate;
6-(4-Isopropoxy-3-{[3-(trifluoromethyl)-5,6-dihydro[1,2,4]triazolo[4,3-a]pyrazin-7(8H)-yl]carbonyl}benzyl)-4,5-dimethyl-3-oxo-2,3-dihydropyridazin-1-ium trifluoroacetate;
6-(4-Fluoro-3-{[3-(trifluoromethyl)-5,6-dihydro[1,2,4]triazolo[4,3-a]pyrazin-7(8H)-yl]carbonyl}benzyl)-4,5-dimethylpyridazin-3(2H)-one;
6-(4-Fluoro-3-{[4-(2-methylprolyl)piperazin-1-yl]carbonyl}benzyl)-4,5-dimethylpyridazin-3(2H)-one;
6-[4-Fluoro-3-(4-methyl-2,5-dioxoimidazolidin-1-yl)benzyl]-4,5-dimethyl-3-oxo-2,3-dihydropyridazin-1-ium trifluoroacetate;
6-(3-{[3-[1-(Dimethylamino)-1-methylethyl]-5,6-dihydro[1,2,4]triazolo[4,3-a]pyrazin-7(8H)-yl]carbonyl}-4-fluorobenzyl)-4,5-dimethyl-3-oxo-2,3-dihydropyridazin-1-ium trifluoroacetate;
(2R)-2-[(4-{5-[(4,5-Dimethyl-6-oxo-1,6-dihydropyridazin-3-yl)methyl]-2-fluorobenzoyl}piperazin-1-yl)carbonyl]-2-methylazetidinium trifluoroacetate;
6-{4-fluoro-3-[(4-{[1-(isobutylamino)cyclopentyl]carbonyl}piperazin-1-yl)carbonyl]benzyl}-4,5-dimethylpyridazin-3(2H)-one trifluoroacetate;
2-(4-{5-[(5-Ethyl-6-oxo-1,6-dihydropyridazin-3-yl)methyl]-2-fluorobenzoyl}-1,4-diazepan-1-yl)pyrimidin-1-ium trifluoroacetate;
4-(1-{5-[(5-Ethyl-6-oxo-1,6-dihydropyridazin-3-yl)methyl]-2-fluorobenzoyl}piperidin-4-yl)pyridinium trifluoroacetate;
2-{[(1-{5-[(5-Ethyl-6-oxo-1,6-dihydropyridazin-3-yl)methyl]-2-fluorobenzoyl}piperidin-4-yl)oxy]methyl}pyridinium trifluoroacetate;
2-{[(1-{5-[(5-Ethyl-6-oxo-1,6-dihydropyridazin-3-yl)methyl]-2-fluorobenzoyl}piperidin-3-yl)oxy]methyl}pyridinium trifluoroacetate;
2-(4-{5-[(5-Ethyl-6-oxo-1,6-dihydropyridazin-3-yl)methyl]-2-fluorobenzoyl}piperazin-1-yl)-5-methoxypyridinium trifluoroacetate;
2-(4-{5-[(5-Ethyl-6-oxo-1,6-dihydropyridazin-3-yl)methyl]-2-fluorobenzoyl}piperazin-1-yl)-4-methoxypyridinium trifluoroacetate;
4-(1-{5-[(5-Ethyl-6-oxo-1,6-dihydropyridazin-3-yl)methyl]-2-fluorobenzoyl}pyrrolidin-3-yl)pyridinium trifluoroacetate;
1-{5-[(5-Ethyl-6-oxo-1,6-dihydropyridazin-3-yl)methyl]-2-fluorobenzoyl}piperidin-3-yl)-N,N-dimethylmethanaminium trifluoroacetate;
4-Ethyl-6-[4-fluoro-3-(1'-H-spiro[1-benzofuran-3,4'-piperidin]-1'-ylcarbonyl)benzyl]pyridazin-3(2H)-one; 1-[2-(1-{5-[(5-Ethyl-6-oxo-1,6-dihydropyridazin-3-yl)methyl]-2-fluorobenzoyl}piperidin-4-yl)ethyl]-1H-pyrazol-2-ium trifluoroacetate;
5-Chloro-2-(4-{5-[(5-ethyl-6-oxo-1,6-dihydropyridazin-3-yl)methyl]-2-fluorobenzoyl}piperazin-1-yl)pyridinium trifluoroacetate;
2-(4-{5-[(5-Ethyl-6-oxo-1,6-dihydropyridazin-3-yl)methyl]-2-fluorobenzoyl}piperazin-1-yl)-6-methoxypyridinium trifluoroacetate;
3-Benzyl-7-{5-[(5-ethyl-6-oxo-1,6-dihydropyridazin-3-yl)methyl]-2-fluorobenzoyl}-5,6,7,8-tetrahydroimidazo[1,2-a]pyrazin-1-ium trifluoroacetate;
2-(4-{5-[(5-Ethyl-6-oxo-1,6-dihydropyridazin-3-yl)methyl]-2-fluorobenzoyl}piperazin-1-yl)-3,6-dimethylpyrazin-1-ium trifluoroacetate;
4-Ethyl-6-{4-fluoro-3-[(3-phenyl-5,6-dihydroimidazo[1,2-a]pyrazin-7(8H)-yl)carbonyl]benzyl}-3-oxo-2,3-dihydropyridazin-1-ium trifluoroacetate;
4-{5-[(5-Ethyl-6-oxo-1,6-dihydropyridazin-3-yl)methyl]-2-fluorobenzoyl}-1-(3-methoxybenzyl)piperazin-1-ium trifluoroacetate;
2-(1-{5-[(5-Ethyl-6-oxo-1,6-dihydropyridazin-3-yl)methyl]-2-fluorobenzoyl}piperidin-4-yl)-1,2,3,4-tetrahydroisoquinolinium trifluoroacetate;
4-{5-[(5-Ethyl-6-oxo-1,6-dihydropyridazin-3-yl)methyl]-2-fluorobenzoyl}piperazin-1-ium trifluoroacetate;
4-{5-[(5-Ethyl-6-oxo-1,6-dihydropyridazin-3-yl)methyl]-2-fluorobenzoyl}-3-phenylpiperazin-1-ium trifluoroacetate;
3-Benzyl-4-{5-[(5-ethyl-6-oxo-1,6-dihydropyridazin-3-yl)methyl]-2-fluorobenzoyl}piperazin-1-ium trifluoroacetate;
4-{5-[(5-Ethyl-6-oxo-1,6-dihydropyridazin-3-yl)methyl]-2-fluorobenzoyl}-2-(pyridinium-3-ylmethyl)piperazin-1-ium bis(trifluoroacetate);
6-(3-{[4-(Cyclopentylcarbonyl)-1,4-diazepan-1-yl]carbonyl}-4-fluorobenzyl)-4,5-dimethylpyridazin-3(2H)-one;
6-(3-{[4-(Cyclopentylcarbonyl)-1,4-diazepan-1-yl]carbonyl}-4-fluorobenzyl)-4-ethylpyridazin-3(2H)-one;
4-{5-[(4,5-Diethyl-6-oxo-1,6-dihydropyridazin-3-yl)methyl]-2-fluorobenzoyl}-1,4-diazepan-1-ium trifluoroacetate;

4-{2-Fluoro-5-[(5-isopropyl-4-methyl-6-oxo-1,6-dihydropyridazin-3-yl)methyl]benzoyl}-1,4-diazepan-1-ium trifluoroacetate;

4-{5-[(4,5-Dimethyl-6-oxo-1,6-dihydropyridazin-3-yl)methyl]-2-fluorobenzoyl}piperazin-1-ium trifluoroacetate;

6-{4-Fluoro-3-[(4-propionylpiperazin-1-yl)carbonyl]benzyl}-4,5-dimethylpyridazin-3(2H)-one;

6-(3-{[4-(Difluoroacetyl)piperazin-1-yl]carbonyl}-4-fluorobenzyl)-4,5-dimethylpyridazin-3(2H)-one;

6-(4-Fluoro-3-{[4-(3,3,3-trifluoropropanoyl)piperazin-1-yl]carbonyl}benzyl)-4,5-dimethylpyridazin-3(2H)-one;

6-{4-Fluoro-3-[(4-isobutyrylpiperazin-1-yl)carbonyl]benzyl}-4,5-dimethyl-3-oxo-2,3-dihydropyridazin-1-ium trifluoroacetate;

2-[(4-{5-[(4,5-Dimethyl-6-oxo-1,6-dihydropyridazin-3-yl)methyl]-2-fluorobenzoyl}piperazin-1-yl)carbonyl]pyridinium trifluoroacetate;

6-(4-Fluoro-3-{[4-(tetrahydrofuran-2-ylcarbonyl)piperazin-1-yl]carbonyl}benzyl)-4,5-dimethylpyridazin-3(2H)-one;

1-(4-{5-[(4,5-Dimethyl-6-oxo-1,6-dihydropyridazin-3-yl)methyl]-2-fluorobenzoyl}piperazin-1-yl)-N,N,2-trimethyl-1-oxopropan-2-aminium trifluoroacetate;

6-(4-Fluoro-3-{[4-(2,2,3,3,3-pentafluoropropanoyl)piperazin-1-yl]carbonyl}benzyl)-4,5-dimethyl-3-oxo-2,3-dihydropyridazin-1-ium trifluoroacetate;

6-(4-Fluoro-3-{[4-(pyrrolidin-1-ylcarbonyl)piperazin-1-yl]carbonyl}benzyl)-4,5-dimethyl-3-oxo-2,3-dihydropyridazin-1-ium trifluoroacetate;

6-(4-Fluoro-3-{[4-(trifluoroacetyl)piperazin-1-yl]carbonyl}benzyl)-4,5-dimethyl-3-oxo-2,3-dihydropyridazin-1-ium trifluoroacetate;

1-(1-{5-[(4,5-Dimethyl-6-oxo-1,6-dihydropyridazin-3-yl)methyl]-2-fluorobenzoyl}piperidin-4-yl)piperidinium trifluoroacetate;

1-(1-{5-[(4,5-Dimethyl-6-oxo-1,6-dihydropyridazin-3-yl)methyl]-2-fluorobenzoyl}piperidin-4-yl)pyrrolidinium trifluoroacetate;

4-(4-{5-[(4,5-Dimethyl-6-oxo-1,6-dihydropyridazin-3-yl)methyl]-2-fluorobenzoyl}piperazin-1-yl)quinazolin-1-ium trifluoroacetate;

2-(4-{5-[(4,5-Dimethyl-6-oxo-1,6-dihydropyridazin-3-yl)methyl]-2-fluorobenzoyl}piperazin-1-yl)pyrimidin-1-ium trifluoroacetate;

7-{5-[(4,5-Dimethyl-6-oxo-1,6-dihydropyridazin-3-yl)methyl]-2-fluorobenzoyl}-3-(3-methylphenyl)-5,6,7,8-tetrahydro[1,2,4]triazolo[4,3-a]pyrazine-1,4-diium bis(trifluoroacetate);

7-{5-[(4,5-Dimethyl-6-oxo-1,6-dihydropyridazin-3-yl)methyl]-2-fluorobenzoyl}-3-[4-(trifluoromethyl)phenyl]-5,6,7,8-tetrahydro[1,2,4]triazolo[4,3-a]pyrazin-1-ium trifluoroacetate;

7-{5-[(4,5-Dimethyl-6-oxo-1,6-dihydropyridazin-3-yl)methyl]-2-fluorobenzoyl}-3-[(4-fluorophenoxy)methyl]-5,6,7,8-tetrahydro[1,2,4]triazolo[4,3-a]pyrazin-2-ium trifluoroacetate;

3-Cyano-2-(4-{5-[(4,5-dimethyl-6-oxo-1,6-dihydropyridazin-3-yl)methyl]-2-fluorobenzoyl}piperazin-1-yl)pyridinium trifluoroacetate;

3-(3,5-Difluorophenyl)-7-{5-[(4,5-dimethyl-6-oxo-1,6-dihydropyridazin-3-yl)methyl]-2-fluorobenzoyl}-5,6,7,8-tetrahydro[1,2,4]triazolo[4,3-a]pyrazin-1-ium trifluoroacetate;

3-[(Dimethylammonio)methyl]-7-{5-[(4,5-dimethyl-6-oxo-1,6-dihydropyridazin-3-yl)methyl]-2-fluorobenzoyl}-5,6,7,8-tetrahydro[1,2,4]triazolo[4,3-a]pyrazin-2-ium bis(trifluoroacetate);

(7-{5-[(4,5-Dimethyl-6-oxo-1,6-dihydropyridazin-3-yl)methyl]-2-fluorobenzoyl}-5,6,7,8-tetrahydro[1,2,4]triazolo[4,3-a]pyrazin-3-yl)-N,N-dimethylmethanaminium trifluoroacetate;

7-{5-[(4,5-Dimethyl-6-oxo-1,6-dihydropyridazin-3-yl)methyl]-2-fluorobenzoyl}-3-(2-furyl)-5,6,7,8-tetrahydro[1,2,4]triazolo[4,3-a]pyrazin-1-ium trifluoroacetate;

7-{5-[(4,5-Dimethyl-6-oxo-1,6-dihydropyridazin-3-yl)methyl]-2-fluorobenzoyl}-3-(pentafluoroethyl)-5,6,7,8-tetrahydro[1,2,4]triazolo[4,3-a]pyrazin-1-ium trifluoroacetate;

7-{5-[(4,5-Dimethyl-6-oxo-1,6-dihydropyridazin-3-yl)methyl]-2-fluorobenzoyl}-3-{[4-(trifluoromethyl)phenyl]amino}-5,6,7,8-tetrahydro[1,2,4]triazolo[4,3-a]pyrazin-1-ium trifluoroacetate;

2-[(4-{2-Fluoro-5-[(6-hydroxy-4,5-dimethylpyridazin-3-yl)methyl]benzoyl}piperazin-1-yl)carbonyl]-2-methylpyrrolidinium chloride;

7-{5-[(4,5-Dimethyl-6-oxo-1,6-dihydropyridazin-3-yl)methyl]-2-fluorobenzoyl}-3-phenyl-5,6,7,8-tetrahydro[1,2,4]triazolo[4,3-a]pyrazin-1-ium trifluoroacetate;

3-(1,3-Benzodioxol-5-yl)-7-{5-[(4,5-dimethyl-6-oxo-1,6-dihydropyridazin-3-yl)methyl]-2-fluorobenzoyl}-5,6,7,8-tetrahydro[1,2,4]triazolo[4,3-a]pyrazin-1-ium trifluoroacetate;

7-{5-[(4,5-Dimethyl-6-oxo-1,6-dihydropyridazin-3-yl)methyl]-2-fluorobenzoyl}-3-(2-thienyl)-5,6,7,8-tetrahydro[1,2,4]triazolo[4,3-a]pyrazin-1-ium trifluoroacetate;

3-Cyclopropyl-6-{5-[(4,5-dimethyl-6-oxo-1,6-dihydropyridazin-3-yl)methyl]-2-fluorobenzoyl}-4,5,6,7-tetrahydro-1H-pyrazolo[3,4-c]pyridin-2-ium trifluoroacetate;

6-{5-[(4,5-Dimethyl-6-oxo-1,6-dihydropyridazin-3-yl)methyl]-2-fluorobenzoyl}-3-(trifluoromethyl)-4,5,6,7-tetrahydro-1H-pyrazolo[3,4-c]pyridin-2-ium trifluoroacetate;

5-{5-[(4,5-Dimethyl-6-oxo-1,6-dihydropyridazin-3-yl)methyl]-2-fluorobenzoyl}-3-(trifluoromethyl)-4,5,6,7-tetrahydro-1H-pyrazolo[4,3-c]pyridin-2-ium trifluoroacetate;

7-{5-[(4,5-Dimethyl-6-oxo-1,6-dihydropyridazin-3-yl)methyl]-2-fluorobenzoyl}-3-pyridinium-3-yl-5,6,7,8-tetrahydro[1,2,4]triazolo[4,3-a]pyrazin-2-ium bis(trifluoroacetate);

7-{5-[(4,5-Dimethyl-6-oxo-1,6-dihydropyridazin-3-yl)methyl]-2-fluorobenzoyl}-7-aza-1-azoniaspiro[3.5]nonane trifluoroacetate;

1-[(1-{3-[(4,5-Dimethyl-6-oxo-1,6-dihydropyridazin-3-yl)methyl]-2-fluorobenzoyl}azetidin-3-yl)methyl]pyrrolidinium trifluoroacetate;

1-(1-{3-[(4,5-Dimethyl-6-oxo-1,6-dihydropyridazin-3-yl)methyl]-2-fluorobenzoyl}piperidin-4-yl)-3,3-difluoroazetidinium trifluoroacetate;

5-{5-[(4,5-Dimethyl-6-oxo-1,6-dihydropyridazin-3-yl)methyl]-2-fluorobenzoyl}-1-(2,2,2-trifluoroethyl)-4,5,6,7-tetrahydro-1H-[1,2,3]triazolo[4,5-c]pyridin-3-ium trifluoroacetate;

1-[(4-{5-[(4,5-Dimethyl-6-oxo-1,6-dihydropyridazin-3-yl)methyl]-2-fluorobenzoyl}piperazin-1-yl)carbonyl]-n-methylcyclopentanaminium trifluoroacetate;

7-{5-[(4,5-Dimethyl-6-oxo-1,6-dihydropyridazin-3-yl)methyl]-2-fluorobenzoyl}-1-methyl-7-aza-1-azoniaspiro[3.5]nonane trifluoroacetate;

6-(4-Methoxy-3-{[3-(trifluoromethyl)-5,6-dihydro[1,2,4]triazolo[4,3-a]pyrazin-7(8H)-yl]carbonyl}benzyl)-4,5-dimethyl-3-oxo-2,3-dihydropyridazin-1-ium trifluoroacetate;

8-{5-[(4,5-Dimethyl-6-oxo-1,6-dihydropyridazin-3-yl)methyl]-2-fluorobenzoyl}-8-aza-2-azoniaspiro[4.5]decane trifluoroacetate;

2-[(4-{5-[(4,5-Dimethyl-6-oxo-1,6-dihydropyridazin-3-yl)methyl]-2-fluorobenzoyl}piperazin-1-yl)carbonyl]-2-propylpyrrolidinium trifluoroacetate;

8-{5-[(4,5-Dimethyl-6-oxo-1,6-dihydropyridazin-3-yl)methyl]-2-fluorobenzoyl}-2-methyl-8-aza-2-azoniaspiro[4.5]decane trifluoroacetate;

3-[(4-{5-[(4,5-Dimethyl-6-oxo-1,6-dihydropyridazin-3-yl)methyl]-2-fluorobenzoyl}piperazin-1-yl)carbonyl]piperidinium trifluoroacetate;

3-[(4-{5-[(4,5-Dimethyl-6-oxo-1,6-dihydropyridazin-3-yl)methyl]-2-fluorobenzoyl}piperazin-1-yl)carbonyl]-1-methylpiperidinium trifluoroacetate;

1-[(4-{5-[(4,5-Dimethyl-6-oxo-1,6-dihydropyridazin-3-yl)methyl]-2-fluorobenzoyl}piperazin-1-yl)carbonyl]-N,N-dimethylcyclopropanaminium trifluoroacetate;

3-(4-{5-[(4,5-Dimethyl-6-oxo-1,6-dihydropyridazin-3-yl)methyl]-2-fluorobenzoyl}piperazin-1-yl)-N,N-dimethyl-3-oxopropan-1-aminium trifluoroacetate;

2-Benzyl-2-[(4-{5-[(4,5-dimethyl-6-oxo-1,6-dihydropyridazin-3-yl)methyl]-2-fluorobenzoyl}piperazin-1-yl)carbonyl]pyrrolidinium trifluoroacetate;

4,5-Dimethyl-6-(3-{[3-(trifluoromethyl)-5,6-dihydro[1,2,4]triazolo[4,3-a]pyrazin-7(8H)-yl]carbonyl}benzyl)pyridazin-3(2H)-one trifluoroacetate;

6-[3-(1,8-Diazaspiro[4.5]dec-8-ylcarbonyl)-4-fluorobenzyl]-4-ethyl-3-oxo-2,3-dihydropyridazin-1-ium trifluoroacetate;

3-[(4-{5-[(4,5-Dimethyl-6-oxo-1,6-dihydropyridazin-3-yl)methyl]-2-fluorobenzoyl}piperazin-1-yl)carbonyl]pyrrolidinium trifluoroacetate;

1-[(4-{5-[(4,5-Dimethyl-6-oxo-1,6-dihydropyridazin-3-yl)methyl]-2-fluorobenzoyl}piperazin-1-yl)carbonyl]-N-methylcyclopropanaminium trifluoroacetate;

3-[(4-{5-[(4,5-Dimethyl-6-oxo-1,6-dihydropyridazin-3-yl)methyl]-2-fluorobenzoyl}piperazin-1-yl)carbonyl]-1-methylpyrrolidinium trifluoroacetate;

3-(4-{5-[(4,5-Dimethyl-6-oxo-1,6-dihydropyridazin-3-yl)methyl]-2-fluorobenzoyl}piperazin-1-yl)-1,1,1-trifluoro-N,N-dimethyl-3-oxopropan-2-aminium trifluoroacetate;

2-[(4-{5-[(4,5-Dimethyl-6-oxo-1,6-dihydropyridazin-3-yl)methyl]-2-fluorobenzoyl}piperazin-1-yl)carbonyl]-2-methylpiperidinium trifluoroacetate;

Benzyl 2-[(4-{5-[(4,5-dimethyl-6-oxo-1,6-dihydropyridazin-3-yl)methyl]-2-fluorobenzoyl}piperazin-1-yl)carbonyl]-2-methylpiperidine-1-carboxylate;

4-Ethyl-6-(4-fluoro-3-{[1-(2,2,2-trifluoroethyl)-1,4,6,7-tetrahydro-5h-[1,2,3]triazolo[4,5-c]pyridin-5-yl]carbonyl}benzyl)pyridazin-3(2H)-one;

4-Ethyl-6-{4-fluoro-3-[(1-methyl-1,8-diazaspiro[4.5]dec-8-yl)carbonyl]benzyl}-3-oxo-2,3-dihydropyridazin-1-ium trifluoroacetate;

(2S)-2-[2-(4-{5-[(4,5-Dimethyl-6-oxo-1,6-dihydropyridazin-3-yl)methyl]-2-fluorobenzoyl}piperazin-1-yl)-2-oxoethyl]pyrrolidinium trifluoroacetate;

8-{5-[(4,5-Dimethyl-6-oxo-1,6-dihydropyridazin-3-yl)methyl]-2-fluorobenzoyl}-1-ethyl-8-aza-1-azoniaspiro[4.5]decane trifluoroacetate;

1-(Cyclopropylmethyl)-8-{5-[(4,5-dimethyl-6-oxo-1,6-dihydropyridazin-3-yl)methyl]-2-fluorobenzoyl}-8-aza-1-azoniaspiro[4.5]decane trifluoroacetate;

6-[3-({4-[(1-Anilinocyclopentyl)carbonyl]piperazin-1-yl}carbonyl)-4-fluorobenzyl]-4,5-dimethylpyridazin-3(2/f)-one;

6-[3-({4-[(1-Aminocyclopentyl)carbonyl]piperazin-1-yl}carbonyl)-4-fluorobenzyl]-4,5-dimethylpyridazin-3(2H)-one;

6-{3-[(4-{[1-(Benzylamino)cyclopentyl]carbonyl}piperazin-1-yl)carbonyl]-4-fluorobenzyl}-4,5-dimethylpyridazin-3(2#)-one trifluoroacetate;

6-(3-{[4-({1-[(Cyclopropylmethyl)amino]cyclopentyl}carbonyl)piperazin-1-yl]carbonyl}-4-fluorobenzyl)-4,5-dimethylpyridazin-3(2H)-one trifluoroacetate;

6-[4-Fluoro-3-({4-[2-(4-fluorobenzyl)prolyl]piperazin-1-yl}carbonyl)benzyl]-4,5-dimethylpyridazin-3 (2H)-one trifluoroacetate;

6-[4-Fluoro-3-({4-[2-(4-methylbenzyl)prolyl]piperazin-1-yl}carbonyl)benzyl]-4,5-dimethylpyridazin-3(2H)-one trifluoroacetate;

6-[4-Fluoro-3-({4-[2-(1-naphthylmethyl)prolyl]piperazin-1-yl}carbonyl)benzyl]-4,5-dimethylpyridazin-3(2H)-one trifluoroacetate;

6-(3-{[4-(2-Ethylprolyl)piperazin-1-yl]carbonyl}-4-fluorobenzyl)-4,5-dimethylpyridazin-3(2H)-one trifluoroacetate;

and pharmaceutically acceptable salts, free bases and tautomers thereof.

Included in the instant invention is the free base of compounds of Formula I, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric, hydrobromic, hydroiodic, sulfuric, sulfurous, sulfamic, phosphoric, phosphorous, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, palmitic, gluconic, ascorbic, phenylacetic, aspartic, cinnamic, pyruvic, ethanesulfonic, ethane, disulfonic, valeric, trifluoroacetic and the like. Examples of suitable polymeric salts include those derived from the polymeric acids such as tannic acid, carboxymethyl cellulose. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, lysine, betaine caffeine, choline, $N,N^1$-dibenzylethylenediamine, ethylamine, diethylamine, 2-diethylaminoethanol, 2-dimethylaminoethanol, ethanolamine, diethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine, dicyclohexylamine, butylamine, benzylamine, phenylbenzylamine, tromethamine and the like.

The preparation of the pharmaceutically acceptable salts described above and other typical pharmaceutically acceptable salts is more fully described by Berg et al (1977) *J. Pharm. Sci., 'Pharmaceutical Salts'*, 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The invention provides compounds for use in the treatment or prevention of conditions which can be ameliorated by the inhibition of poly(ADP-ribose)polymerase (PARP) (see, for example, *Nature Review Drug Discovery* (2005) 4:421-440).

Thus, the present invention provides a compound of formula I for use in the manufacture of a medicament for the treatment or prevention of conditions which can be ameliorated by the inhibition of poly(ADP-ribose)polymerase (PARP).

The present invention also provides a method for the treatment or prevention of conditions which can be ameliorated by the inhibition of poly(ADP-ribose)polymerase (PARP), which method comprises administration to a patient in need thereof of an effective amount of a compound of formula I or a composition comprising a compound of formula I.

The PARP inhibitors of the present invention are useful for the treatment of the diseases specified in WO 2005/082368.

The compounds of the invention are useful for the treatment of inflammatory diseases, including conditions resulting from organ transplant rejection, such as; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; diabetic complications, including, but not limited to, immune-complex vasculitis, systemic lupus erythematosus (SLE); inflammatory diseases of the heart such as cardiomyopathy, ischemic heart disease, hypercholesterolemia, and atherosclerosis; as well as various other diseases that can have significant inflammatory components, including preeclampsia, chronic liver failure, brain and spinal cord trauma and multiple organ dysfunction syndrome (MODS) (multiple organ failure (MOF)). The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g. by a chemotherapeutic agent that is administered as a treatment for cancer.

Thus, the present invention provides a compound of formula I for use in the manufacture of a medicament for treating or preventing inflammatory diseases.

The present invention also provides a method for the treatment or prevention of inflammatory diseases, which method comprises administration to a patient in need thereof of an effective amount of a compound of formula I or a composition comprising a compound of formula I.

The compounds of the instant invention may also be useful in the treatment or prevention of reperfusion injuries, resulting from naturally occurring episodes and during a surgical procedure, such as intestinal reperfusion injury; myocardial reperfusion injury; reperfusion injury resulting from cardiopulmonary bypass surgery, aortic aneurysm repair surgery, carotid endarterectomy surgery, or hemorrhagic shock; and deoxygenation injury resulting from transplantation of organs such as heart, lung, liver, kidney, pancreas, intestine, and cornea.

Thus, the present invention provides a compound of formula I for use in the manufacture of a medicament for the treatment or prevention of reperfusion injuries.

The present invention also provides a method for the treatment or prevention of reperfusion injuries, which method comprises administration to a patient in need thereof of an effective amount of a compound of formula I or a composition comprising a compound of formula I.

The compounds of the instant invention may also be useful in the treatment or prevention of ischemic conditions, including those resulting from organ transplantation, such as stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemia kidney disease, ischemic liver disease, ischemic retinal disorder, septic shock, and an ischemic disease of the central nervous system, such as stroke or cerebral ischemia.

Thus, the present invention provides a compound of formula I for use in the manufacture of a medicament for the treatment or prevention of ischemic conditions.

The present invention also provides a method for the treatment or prevention of ischemic conditions, which method comprises administration to a patient in need thereof of an effective amount of a compound of formula I or a composition comprising a compound of formula I.

The present invention provides a compound of formula I for use in the manufacture of a medicament for the treatment or prevention of stroke.

The present invention also provides a method for the treatment or prevention of stroke, which method comprises administration to a patient in need thereof of an effective amount of a compound of formula I or a composition comprising a compound of formula I.

The compounds of the instant invention may also be useful for the treatment or prevention of chronic or acute renal failure.

Thus, the present invention provides a compound of formula I for use in the manufacture of a medicament for the treatment or prevention of renal failure.

The present invention also provides a method for the treatment or prevention of renal failure, which method comprises administration to a patient in need thereof of an effective amount of a compound of formula I or a composition comprising a compound of formula I.

The compounds of the instant invention may also be useful for the treatment or prevention of vascular diseases other than cardiovascular diseases, such as peripheral arterial occlusion, thromboangitis obliterans, Reynaud's disease and phenomenon, acrocyanosis, erythromelalgia, venous thrombosis, varicose veins, arteriovenous fistula, lymphedema and lipedema.

Thus, the present invention provides a compound of formula I for use in the manufacture of a medicament for the treatment or prevention of vascular diseases other than cardiovascular diseases.

The present invention also provides a method for the treatment or prevention of vascular diseases other than cardiovascular diseases, which method comprises administration to a patient in need thereof of an effective amount of a compound of formula I or a composition comprising a compound of formula I.

The compounds of the instant invention may also be useful for the treatment or prevention of cardiovascular diseases such as chronic heart failure, atherosclerosis, congestive heart failure, circulatory shock, cardiomyopathy, cardiac transplant, myocardial infarction, and a cardiac arrhythmia, such as atrial fibrillation, supraventricular tachycardia, atrial flutter, and paroxysmal atrial tachycardia.

Thus, the present invention provides a compound of formula I for use in the manufacture of a medicament for the treatment or prevention of cardiovascular diseases.

The present invention also provides a method for the treatment or prevention of cardiovascular diseases, which method comprises administration to a patient in need thereof of an effective amount of a compound of formula I or a composition comprising a compound of formula I.

The compounds of this invention may also be useful for the treatment and prevention of diabetes mellitus, including Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by (3-cell toxins. The compounds of this invention may also be useful for the treatment or prevention of diabetic complications, such as diabetic cataract, glaucoma, retinopathy, nephropathy, (such asmicroaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathies, autonomic neuropathy, a foot ulcer, a joint problem, a fungal infection, a bacterial infection, and cardiomyopathy.

Thus, the present invention provides a compound of formula I for use in the manufacture of a medicament for the treatment or prevention of diabetes.

The present invention also provides a method for the treatment or prevention of diabetes, which method comprises administration to a patient in need thereof of an effective amount of a compound of formula I or a composition comprising a compound of formula I.

The compounds of this invention may also be useful for the treatment or prevention of cancer including solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, skin cancer, melanoma, neuroblastoma and retinoblastoma; blood-borne cancers such as acute lymphoblastic leukemia ("ALL"), acute lymphoblastic B-cell leukemia, acute lymphoblastic T-cell leukemia, acute myeloblastic leukemia ("AML"), acute promyelocyte leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, myelocytic leukemias; Lymphomas such as Hodgkin's disease, non-Hodgkin's Lymphoma, Multiple myeloma, Waldenstrom's macroglobulinemia, Heavy chain disease and Polycythemia vera; CNS and brain cancers such as glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor and medulloblastoma.

Thus, the present invention provides a compound of formula I for use in the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

The compounds of the present invention may also be used for the treatment of cancer which is deficient in Homologous Recombination (HR) dependent DNA DSB repair activity (see WO 2006/021801).

The HR dependent DNA DSB repair pathway repairs double-strand breaks (DSBs) in DNA via homologous mechanisms to reform a continuous DNA helix (*Nat. Genet.* (2001) 27(3):247-254). The components of the HR dependent DNA DSB repair pathway include, but are not limited to, ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D, DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9. Other proteins involved in the HR dependent DNA DSB repair pathway include regulatory factors such as EMSY (*Cell* (2003)115:523-535).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterized in the art (see for example, *Science* (2001)291: 1284-1289) and include the components listed above.

The present invention provides a compound of formula I for use in the manufacture of a medicament for the treatment or prevention of a cancer which is deficient in HR dependent DNA DSB repair activity.

The present invention also provides a method for the treatment or prevention of a cancer which is deficient in HR dependent DNA DSB repair activity, which method comprises administration to a patient in need thereof of an effective amount of a compound of formula I or a composition comprising a compound of formula I In an embodiment the cancer cells are deficient in the HR dependent DNA DSB repair activity of one or more phenotypes selected from ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D, DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9.

In another embodiment, the cancer cells have a BRCA1 and/or a BRCA2 deficient phenotype. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (*Cell* (2003) 115:523-535).

BRCA-1 and BRCA-2 are known tumor suppressors whose wild-type alleles are frequently lost in tumors of heterozygous carriers (*Oncogene*, (2002) 21(58):8981-93; *Trends Mol. Med.*, (2002) 8(12):571-6). The association of BRCA-1 and/or BRCA-2 mutations with breast cancer has been well-characterized (*Exp Clin Cancer Res.*, (2002) 21 (3 Suppl):9-2). Amplification of the EMSY gene, which encodes a BRCA-2 binding factor, is also known to be associated with breast and ovarian cancer. Carriers of mutations in BRCA-1 and/or BRCA-2 are also at elevated risk of cancer of the ovary, prostate and pancreas. The detection of variation in BRCA-1 and BRCA-2 is well-known in the art and is described, for example in EP 699 754, EP 705 903, *Genet. Test* (1992) 1:75-83; *Cancer Treat Res* (2002) 107:29-59; *Neoplasm* (2003) 50(4):246-50; *Ceska Gynekol* (2003) 68(1): 11-16). Determination of amplification of the BRCA-2 binding factor EMSY is described in *Cell* 115:523-535. PARP inhibitors have been demonstrated as being useful for the specific killing of BRCA-1 and BRCA-2 deficient tumors (*Nature* (2005) 434:913-916 and 917-920).

Thus, the present invention provides a compound of formula I for use in the manufacture of a medicament for the treatment or prevention of BRCA-1 or BRCA-2 deficient tumors.

The present invention also provides a method for the treatment or prevention of BRCA-1or BRCA-2 deficient tumors, which method comprises administration to a patient in need thereof of an effective amount of a compound of formula I or a composition comprising a compound of formula I.

In an embodiment, the PARP inhibitors of the present can be used in prophylactic therapy for elimination of BRCA2-deficient cells (see, *Cancer Res.* (2005) 65:10145).

The compounds of this invention may be useful for the treatment or prevention of neurodegenerative diseases, including, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS).

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the present invention may also be useful for the treatment or prevention of retroviral infection (U.S. Pat. No. 5,652,260), retinal damage (*Curr. Eye Res.* (2004), 29:403), skin senescence and UV-induced skin damage (US5589483 and *Biochem. Pharmacol* (2002) 63:921).

The compounds of the invention are useful for the treatment or prevention of premature aging and postponing the onset of age-related cellular dysfunction (*Pharmacological Research* (2005) 52:93-99).

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The instant compounds are also useful in combination with anti-cancer agents or chemotherapeutic agents.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a compound of formula I and an anti-cancer agent for simultaneous, separate or sequential administration.

The present invention also provides a compound of formula I for use in the manufacture of a medicament for use as an adjunct in cancer therapy or for potentiating tumor cells for treatment with ionizing radiation or chemotherapeutic agents.

The present invention also provides a method of chemotherapy or radiotherapy, which method comprises administration to a patient in need thereof of an effective amount of a compound of formula I or a composition comprising a compound of formula I in combination with ionizing radiation or chemotherapeutic agents.

In combination therapy, the compounds of this invention can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent to a subject in need thereof. In various embodiments the instant compounds and another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors, HIV protease inhibitors, reverse transcriptase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites, biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, cyclophosphamide, chlorambucil carmustine (BCNU), lomustine (CCNU), busulfan, treosulfan, sertenef, cachectin, ifosfamide, tasonermin, lonidamine, carboplatin, altretamine, prednimustine, dibromodulcitol, ranimustine, fotemustine, nedaplatin, aroplatin, oxaliplatin, temozolomide, methyl methanesulfonate, procarbazine, dacarbazine, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, doxorubicin, epirubicin, pirarubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulphonyl-daunorubicin (see WO 00/50032).

In an embodiment the compounds of this invention can be used in combination with alkylating agents.

Examples of alkylating agents include but are not limited to, nitrogen mustards: cyclophosphamide, ifosfamide, trofosfamide and chlorambucil; nitrosoureas: carmustine (BCNU) and lomustine (CCNU); alkylsulphonates: busulfan and treosulfan; triazenes: dacarbazine, procarbazine and temozolomide; platinum containing complexes: cisplatin, carboplatin, aroplatin and oxaliplatin.

In an embodiment, the alkylating agent is dacarbazine. Dacarbazine can be administered to a subject at dosages ranging from about 150 mg/m2 (of a subject's body surface area) to about 250 mg/m2. In another embodiment, dacarbazine is administered intravenously to a subject once per day for five consecutive days at a dose ranging from about 150 mg/m2 to about 250 mg/m2.

In an embodiment, the alkylating agent is procarbazine. Procarbazine can be administered to a subject at dosages ranging from about 50 mg/m2 (of a subject's body surface area) to about 100 mg/m2. In another embodiment, procarbazine is administered intravenously to a subject once per day for five consecutive days at a dose ranging from about 50 mg/m2 to about 100 mg/m2.

In an embodiment, the alkylating agent is temozoloamide. Temozolomide can be administered to a subject at dosages ranging from about 150 mg/m2 (of a subject's body surface area) to about 200 mg/m2. In another embodiment, temozolomide is administered orally to an animal once per day for five consecutive days at a dose ranging from about 150 mg/m2 to about 200 mg/m2.

Examples of anti-mitotic agents include: allocolchicine, halichondrin B, colchicine, colchicine derivative, dolstatin 10, maytansine, rhizoxin, thiocolchicine and trityl cysteine.

An example of a hypoxia activatable compound is tirapazamine.

Examples of proteasome inhibitors include but are not limited to lactacystin, bortezomib, epoxomicin and peptide aldehydes such as MG 132, MG 115 and PSI.

Examples of microtubule inhibitors/microtubule-stabilising agents include paclitaxel, vindesine sulfate, vincristine, vinblastine, vinorelbine, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, exatecan, gimetecan, diflomotecan, silyl-camptothecins, 9-aminocamptothecin, camptothecin, crisnatol, mitomycin C, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3,4':b,7]-indolizino[1,2b]quinoline-10,13(9H, 15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna; non-camptothecin topoisomerase-1 inhibitors such as indolocarbazoles; and dual topoisomerase-1 and II inhibitors such as benzophenazines, XR 20 115761MLN 576 and benzopyridoindoles.

In an embodiment, the topoisomerase inhibitor is irinotecan. Irinotecan can be administered to a subject at dosages ranging from about 50 mg/m2 (of a subject's body surface area) to about 150 mg/m2. In another embodiment, irinotecan is administered intravenously to a subject once per day for five consecutive days at a dose ranging from about 50 mg/m2 to about 150 mg/m2 on days 1-5, then again intravenously once per day for five consecutive days on days 28-32 at a dose ranging from about 50 mg/m2 to about 150 mg/m2, then again intravenously once per day for five consecutive days on days 55-59 at a dose ranging from about 50 mg/m2 to about 150 mg/m2.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R[1].

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(5)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* (1999), 35(9): 1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1-(VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS (1992) 89:7384; *JNCI* (1982) 69:475; *Arch. Opthalmol.* (1990) 108: 573; *Anat. Rec.* (1994) 238:68; *FEBS Letters* (1995) 372:83; *Clin, Orthop.* (99S) 313:76; *J. Mol. Endocrinol.* (1996) 16:107; *Jpn. J. Pharmacol.* (1997) 75:105; *Cancer Res.* (1997) 57:1625 (1997); *Cell* (1998) 93:705; *Intl. J. Mol. Med.* (1998) 2:715; *J. Biol. Chem.* (1999) 274:9116)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see *J. Lab. Clin. Med.* (1985) 105:141-145), and antibodies to VEGF (see *Nature Biotechnology* (1999) 17:963-968; Kim et al (1993) *Nature* 562:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* (2000) 38:679-692). Examples of such agents that modulate or inhibit the coagulation and fibrinolysis pathways include, but are not limited to, heparin (see *Thromb. Haemost.* (1998) 80:10-23), low molecular weight heparins and carboxypeptidase U inhibitors (also known as inhibitors of active thrombin activatable fibrinolysis inhibitor [TAFIa]) (see *Thrombosis Res.* (2001) 101:329-354). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, staurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

In an embodiment, the compounds of the present invention are useful for the treatment or prevention of the appearance of necrosis induced by selective N3-adenine methylating agents such as MeOSO$_2$(CH$_2$)-lexitropsin (Me-Lex).

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* (1998) 31:909-913; *J. Biol. Chem.* (1999) 274: 9116-9121; *Invest. Opthalmol. Vis. Sci.* (2000) 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853, verapamil and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABA$_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159 93/01165, 93/01169, 93/01170, 93/06099, 93/09116, 93/10073, 93/14084, 93/14113, 93/18023 93/19064, 93/21155, 93/21181, 93/23380, 93/24465, 94/00440, 94/01402, 94/02461, 94/02595 94/03429, 94/03445, 94/04494, 94/04496, 94/05625, 94/07843, 94/08997, 94/10165, 94/10167 94/10168, 94/10170, 94/11368, 94/13639, 94/13663, 94/14767, 94/15903, 94/19320, 94/19323 94/20500, 94/26735, 94/26740, 94/29309, 95/02595, 95/04040, 95/04042, 95/06645, 95/07886 95/07908, 95/08549, 95/11880, 95/14017, 95/15311, 95/16679, 95/17382, 95/18124, 95/18129 95/19344, 95/20575, 95/21819, 95/22525, 95/23798, 95/26338, 95/28418, 95/30674, 95/30687 95/33744, 96/05181, 96/05193, 96/05203, 96/06094, 96/07649, 96/10562, 96/16939, 96/18643 96/20197, 96/21661, 96/29304, 96/29317, 96/29326, 96/29328, 96/31214, 96/32385, 96/37489 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with ionizing radiation and/or in combination with a second compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immuno logic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treatment" refers to the treatment of a mammal afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "adjunct" refers to the use of compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfere with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

Abbreviations Used in the Description of the Chemistry and in the Examples that Follow are:
AcOH (acetic acid); DCM (dichloromethane); DIPEA (N,N'-Diisopropylethylamine); DMA (N,N-dimethylacetamide); DMAP (4-dimethyaminooyridine); DMF (dimethylformamide); DMSO (dimethyl sulfoxide); eq. (equivalent); EtOAc (ethyl acetate); HBTU (O-Benzotriazole-N,N,N',N'-tetramethyl-uronium-hexafluoro-phosphate); NaH (sodium hydride); NMR (nuclear magnetic resonance); PyBOP (1H-benzotriazol-1-yl-oxytripyrrolidinophosphonium); RP-HPLC (reverse phase high performance liquid chromatography); RT (room temperature); sat. aq. (saturated aqueous); TBTU (O-(1H-benzotriazol-1-yl)-N,N,N',N'-tetramethyluronium tetrafluoroborate); TEA (triethylamine); TFA (trifluoroacetic acid); and THF (tetrahydrofuran).

Compounds of formula I wherein c is 0 and d is 1 can be prepared by condensation of a compound of formula IA with a compound of formula IB:

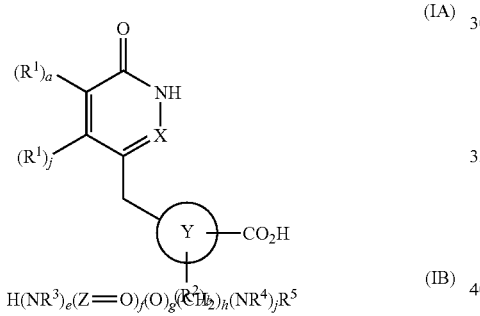

(IA)

(IB)

wherein a, b, e, f, g, h, i, j, X, Y, Z, $R^1$, $R^2$, $R^3$, $R^4$ and $R^5$ are as defined above. The reaction can generally be carried out in the presence of coupling agents such as HBTU and DIPEA, in a solvent such as DMA at about room temperature. A coupling agent such as TBTU and a solvent such as DMF may also be used. Analogous coupling conditions can be used in any step in the synthesis of compounds of formula I using appropriate combinations of starting materials.

Compounds of formula IA can be prepared by concurrent hydrolysis and decarboxylation of a compound of formula IC:

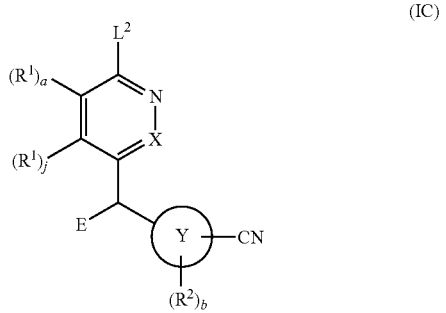

(IC)

wherein a, b, j, $R^1$, $R^2$, X and Y are as defined above, E is an electron withdrawing group, such as cyano and $L^2$ is a leaving group such as halogen, for example fluorine or chlorine. The reaction is generally carried out under acidic or basic conditions. For example a base such as NaOH may be used at a temperature of about 90° C. The reaction may be carried out in solvents such as AcOH and HCl at reflux.

Compounds of formula IC can be prepared by reacting a compound of formula ID with a compound of formula IE:

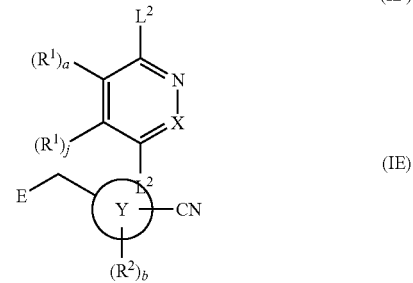

(ID)

(IE)

wherein a, b, j, $R^1$, $R^2$, X, Y, E and each L2 is independently as defined above. The reaction is generally carried out in the presence of a base such as NaH, in a solvent such as DMF at about 0° C. to room temperature.

Alternatively compounds of formula I can be prepared by concurrent hydrolysis and decarboxylation of a compound of formula IF:

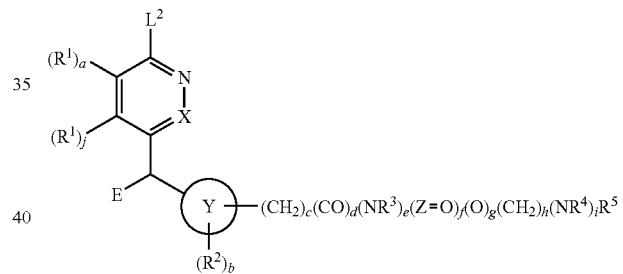

(IF)

wherein a, b, c, d, e, f, g, h, i, j, X, Y, Z, $R^1$, $R^2$, $R^3$, $R^4$, $R^5$, $L^2$ and E are as defined above. The reaction is generally carried out under acidic or basic conditions.

Compounds of formula IF can be prepared by reacting a compound of formula ID with a compound of formula IG:

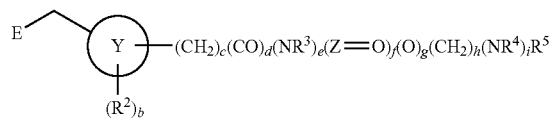

(IG)

wherein b, c, d, e, f, g, h, i, Y, Z, $R^2$, $R^3$, $R^4$, $R^5$ and E are as defined above. The reaction is generally carried out in the presence of a base such as NaH, in a solvent such as DMF at about 0° C. to room temperature.

Where the synthesis of intermediates and starting materials is not described, these compounds are commercially available or can be made from commercially available compounds by standard methods or by extension of the Examples herein.

Compounds of formula I may be converted to other compounds of formula I by known methods or by methods described in the Examples.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc protecting group is present, it may be removed by the addition of TFA in solvents such as DCM and/or MeCN at about room temperature. EtOAc in the presence of HCl and 1,4-dioxane may alternatively be used, at about room temperature. The benzylcarbonyl protecting group can be removed by hydrogenation using standard methods, such as treating with a catalyst such as Pd/C, in a solvent such as methanol under a hydrogen atmosphere.

The compounds of this invention were prepared according to the following schemes. All variables within the formulae are as defined above.

Scheme 1

Compounds described in this invention can be prepared using the methods described below. For instance, 3,6-dichloro-4-alkylpyridazine and 3,6-dichloro-4,5-dialkylpyridazines can be obtained by followed by radical addition to the dichloropyridazine, the appropriate radicals are generated by decarboxylation of the appropriate alkanoic acid with ammonium peroxodisulfate in presence of Ag(I), as described in *Org. Prep.+Proc. Int.* 1988, 20, 117. The reaction of the substituted 3,6-dichloropyridazine derivatives with a (hetero) aromatic group bearing an activated methylene group, activated by an electron withdrawing group such as an ester or nitrile, in the presence of base allows displacement of the chlorine groups to give a mixture of the two regioisomeric 3-((hetero)arylmethyl)pyridazines. Hydrolysis of this isomeric mixture, with concurrent decarboxylation and hydrolysis of the imino chloride group, results in the formation of the desired scaffold. At this stage the mixture of isomers may be separated (Scheme 1).

Scheme 1

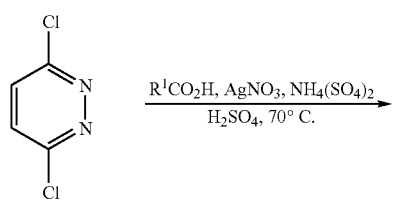

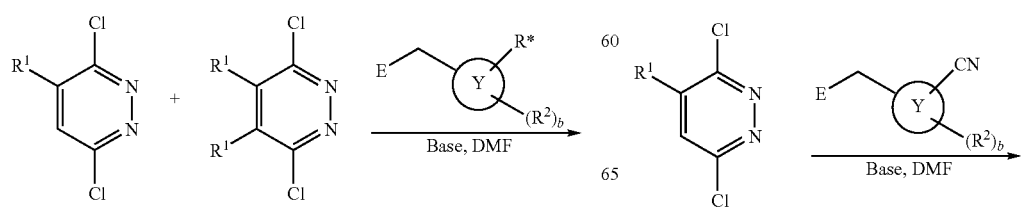

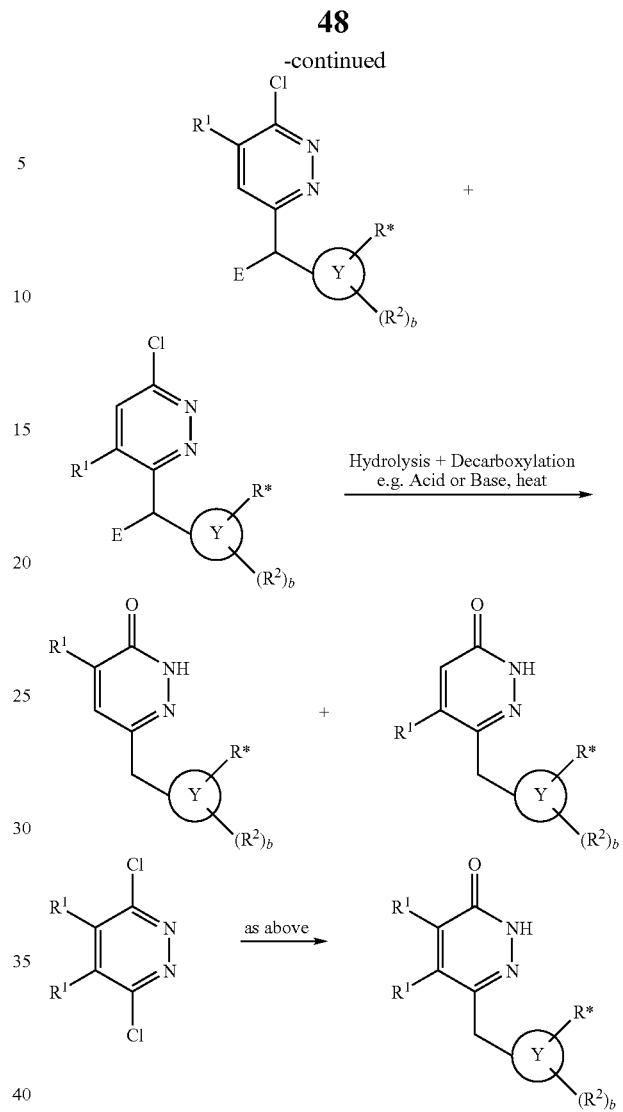

wherein:
E is an electron withdrawing group e.g. —CO$_2$Alkyl, —CN;
R* is (CH$_2$)$_c$(CO)$_d$(NR$^3$)$_e$(Z═O)$_f$(O)$_g$(CH$_2$)$_h$(NR$^4$)$_i$R$^5$;
R$^1$ is C$_{1-6}$alkyl; and all variables are as defined above

Scheme 2

Under certain circumstances the (hetero)aromatic group can bear a functional handle that can be further manipulated to yield other derivatives. For instance, a (hetero)aromatic nitrile can be carried through the synthetic sequence. This functional group can be hydrolysed during the decarboxylation reaction to yield the corresponding carboxylic acid. In turn, this can be coupled with various amines to yield the desired PARP inhibitors (Scheme 2).

Scheme 2

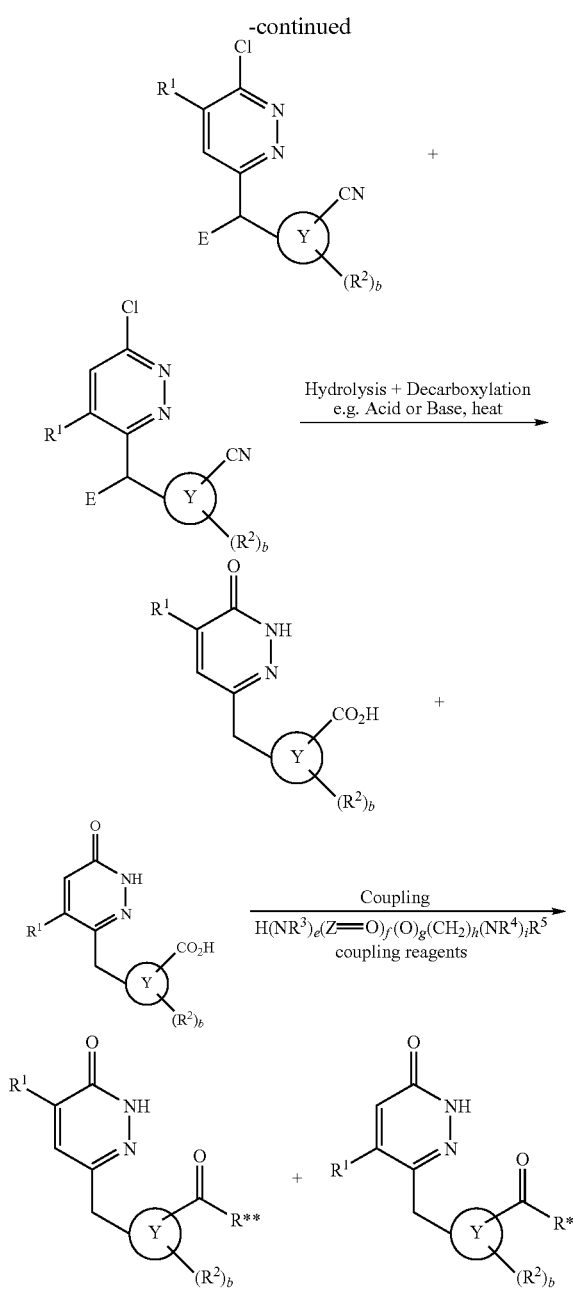

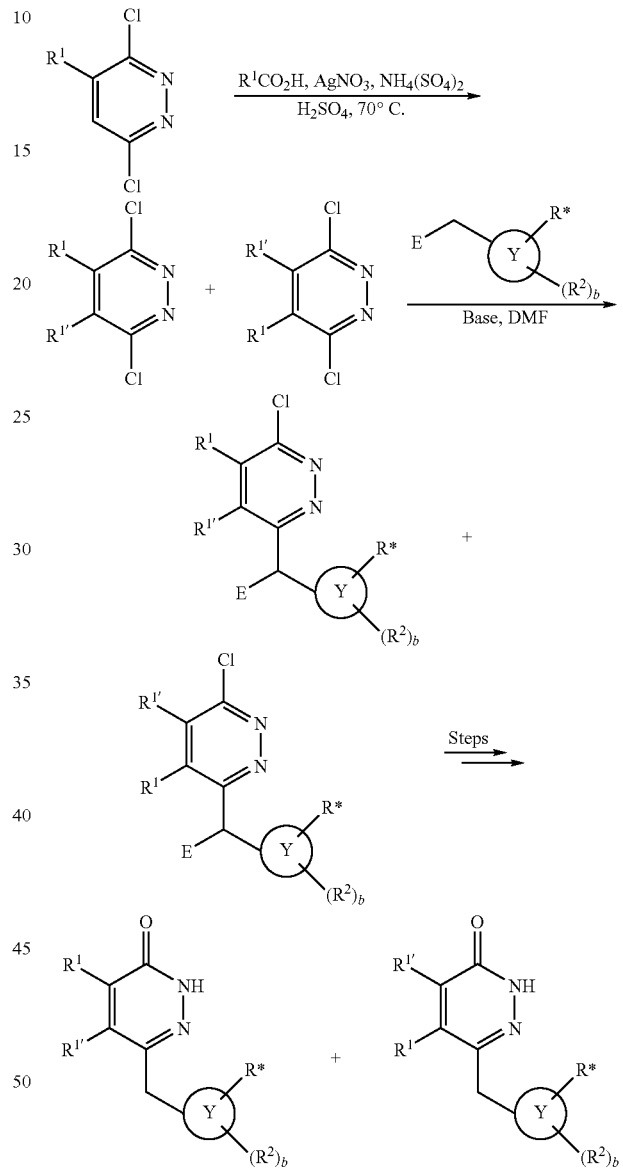

described previously. Asymmetric 3,6-dichloro-4-alkyl-5-alkyl*-pyridazines, can then be formed by reacting with a second alkyl radical by decarboxylation of the appropriate alkanoic acid with ammonium peroxodisulfate in presence of Ag(I), as described in *Org. Prep.+Proc. Int.* 1988, 20, 117. The reaction sequences as described above allow the elaboration of the desired PARP inhibitors (Scheme 3).

The inhibitors of the present invention can be transformed into other related derivatives by standard transformations known to those skilled in the art. For instance: coupling reactions of amino groups with: carboxylic acids using coupling reagents like HBTU, HATU, TBTU and PyBoP, or with activated acyl groups; sulfonylations reactions using sulfonyl chlorides; or reductive animations using a carbonyl derivative and an amino group, using a reducing agent like sodium cyanoborohydride.

Scheme 3

3,6-dichloro-4-alkylpyridazine can be prepared by addition of the alkyl radical to the dichloropyridazine, as Scheme 4

An alternative method to convert these PARP inhibitors into related compounds is using a Curtius reaction. A compound containing a carboxylic acid can be treated with diphenylphosphoryl azide in an alcoholic solvent at reflux and undergo a Curtius rearrangement reaction to the corresponding carbamate. This carbamate can then be hydrolyzed under acidic conditions to the corresponding (hetero)aniline derivative which thereafter can be elaborated into the desired PARP inhibitors by coupling reaction under standard conditions (Scheme 8). In a related manner, the (hetero)aniline derivative can be coupled with either a acyl anhydride and then further cyclised to the corresponding imide by addition of a coupling reagent such as TBTU. Alternatively, the (hetero)anilide can be coupled with an carboxylic acid containing a carbamate moiety, subsequent microwave irradiation in the presence of DMAP allows cyclisation to the corresponding cyclic urea.

Scheme 4

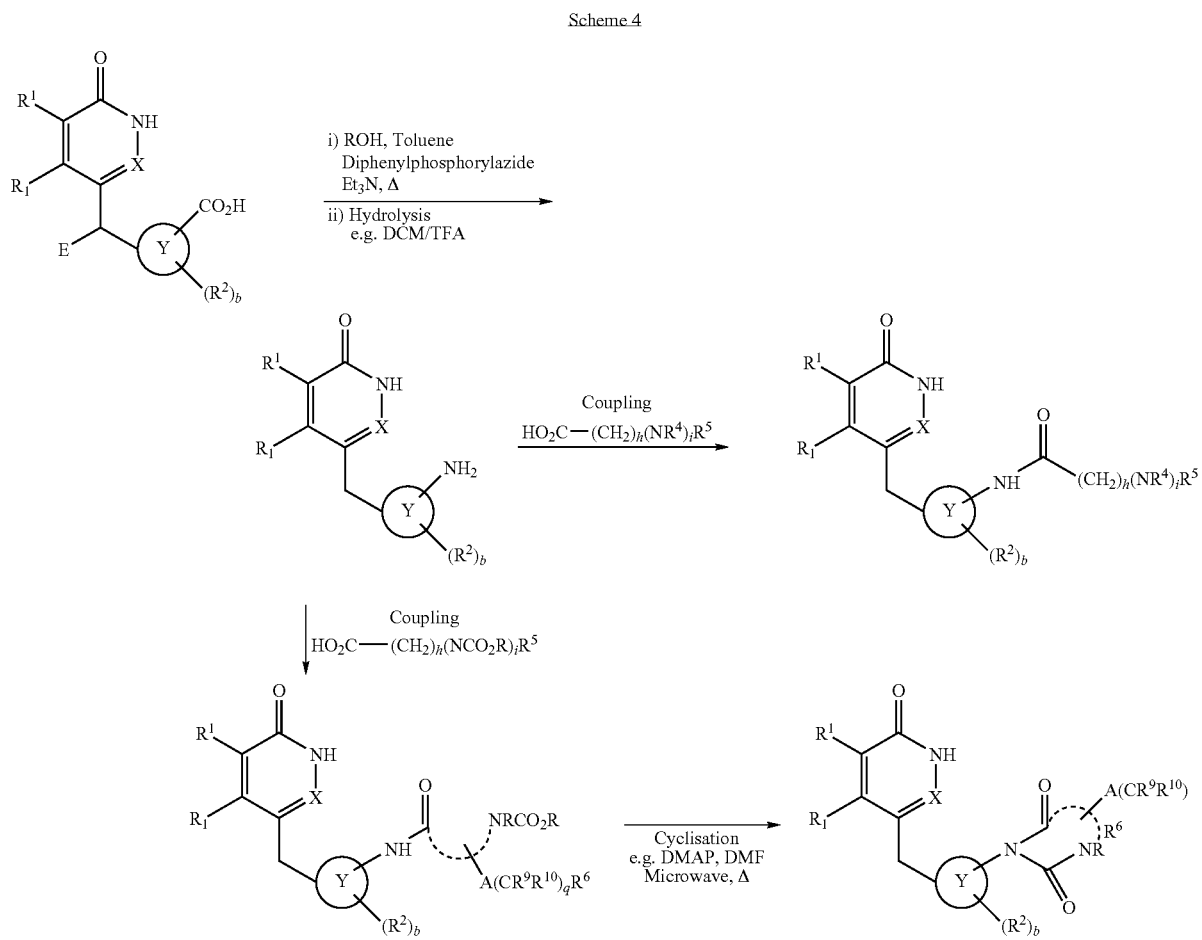

Scheme 5

A further method to convert one type of inhibitor into another is to carry out a nucleophilic aromatic substitution reaction on the Y ring. For example, a halogen group, for instance a fluoride, on the (hetero)aromatic ring can be displaced with an alkoxide ion or an amino group. Treatment with a sodium alkoxide in a refluxing alcohol solvent allows an alkoxy group to be introduced on the Y ring. Alternatively, vigorous heating of the substrate in a solution of the amine in a polar solvent like DMF, in a sealed reaction vessel, allows the formation of alkylamino and dialkylamino groups on the Y ring. Subsequent functional group manipulations such as the hydrolysis of nitrile groups in strong basic media at reflux and coupling, gives the desired PARP inhibitors (Scheme 5).

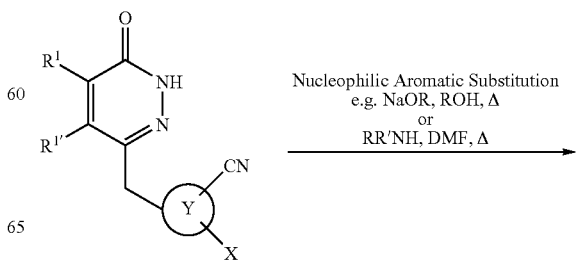

-continued

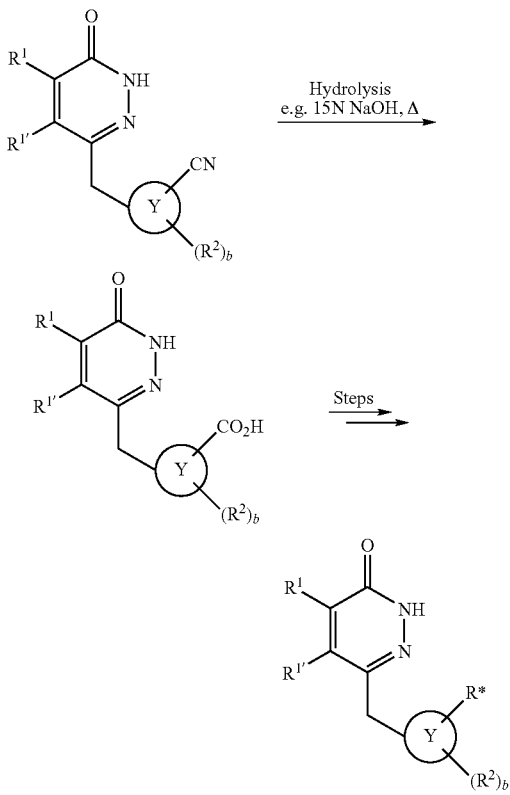

wherein:
X = Halogen, e.g. fluorine
R* is $(CH_2)_e(CO)_d(NR^3)_e(Z=O)_f(O)_g(CH_2)_h(NR^4)_iR^5$;
R, R', $R^1$ and $R^{1'}$ are $C_{1-6}$alkyl; and all variables are as defined above The exemplified compounds described herein were tested by the assays described below and were found to have an $IC_{50}$ value of less than 5 μM.

PARP-1 SPA Assay

Working Reagents

Assay buffer: 100 mM Tris pH 8, 4 mM $MgCl_2$, 4 mM Spermine, 200 mM KCl, 0.04% Nonidet P-40.

Enzyme Mix: Assay buffer (12.5 ul), 100 mM DTT (0.5 ul), PARP-1 (5 nM, Trevigen 4668-500-01), $H_2O$ (to 35 ul).

Nicotinamide-adenine dinucleotide (NAD)/DNA Mix: [$^3$H-NAD] (250 uCi/ml, 0.4 ul, Perkin-Elmer NET-443H), NAD (1.5 mM, 0.05 ul, SIGMA N-1511), Biotinylated-NAD (250 uM, 0.03 ul, Trevigen 4670-500-01), Activated calf thymus (1 mg/ml, 0.05 ul, Amersham Biosciences 27-4575), $H_2O$ (to 10 ul).

Developing Mix: Streptavidin SPA beads (5 mg/ml, Amersham Biosciences RPNQ 0007) dissolved in 500 mM EDTA.

EXPERIMENTAL DESIGN

The reaction is performed in 96-well microplate with a final volume of 50 uL/well. Add 5 ul 5% DMSO/compound solution, add enzyme mix (35 ul), start the reaction by adding NAD/DNA mix (10 uL) and incubate for 2 hrs at RT. Stop the reaction by adding developing mix (25 ul) and incubate 15 min at RT. Measure using a Packard TOP COUNT instrument.

Example 1

4-{5-[(5-Ethyl-6-oxo-1,6-dihydropyridazin-3-yl)methyl]-2-fluorobenzoyl}-1,4-diazepan-1-ium Trifluoroacetate (A4)

Step 1: 5-[(6-chloro-5-ethylpyridazin-3-yl)(cyano)methyl]-2-fluorobenzonitrile (A1) and 5-[(6-chloro-4-ethylpyridazin-3-yl)(cyano)methyl]-2-fluorobenzonitrile (A2)

To an ice-cold solution of 5-(cyanomethyl)-2-fluorobenzonitrile (1 eq) and 3,6-dichloro-4-ethylpyridazine (1.9 eq) (Reference: Org. Prep.+Proc. Int. 1988, 20, 117 and U.S. Pat. No. 4,628,088, 1986) in DMF was added portionwise NaH (2.1 eq). The reaction was stirred at 0° C. for 15 min and then warmed to RT and stirred for 2 hrs. The reaction was quenched with a sat. aq. $NaHCO_3$ and extracted with EtOAc. The combined organic fractions were washed with brine, dried ($Na_2SO_4$) and concentrated under reduced pressure. An isomeric mixture of 4- and 5-ethylpyridazine was separated by silica gel chromatography, eluting with 9:1 Hexanes:EtOAc to afford first the 5-substituted isomer (A1) and subsequently the 4-substituted isomer (A2).

5-[(6-chloro-5-ethylpyridazin-3-yl)(cyano)methyl]-2-fluorobenzonitrile (A1): $^1$H NMR (300 MHz, $CDCl_3$) δ: 7.80-7.78 (2H, m), 7.48 (1H, s), 7.31-7.29 (1H, m), 5.63 (1H, s), 2.81 (2H, qd, J=7.6 and 3.1 Hz), 1.31 (3H, t, J=7.6 Hz). MS (ES) $C_{15}H_{10}ClFN_4$ requires: 300/302. found: 301/303 (M+H)$^+$.

5-[(6-chloro-4-ethylpyridazin-3-yl)(cyano)methyl]-2-fluorobenzonitrile (A2): $^1$H NMR (400 MHz, $CDCl_3$) δ: 7.75-7.67 (2H, m), 7.45 (1H, s), 7.30 (1H, t, J=8.6 Hz), 5.74 (1H, s), 2.80-2.70 (1H, m), 2.60-2.50 (1H, m), 1.26 (3H, t, J=7.3 Hz). MS (ES) $C_{15}H_{10}ClFN4$ required: 300/302. found: 301/303 (M+H)+.

Step 2: 5-[(5-ethyl-6-oxo-1,6-dihydropyridazin-3-yl)methyl]-2-fluorobenzoic Acid (A3)

A mixture of A1 (1 eq) in AcOH, conc. HCl and $H_2O$ (1:2:1, 0.065 M) was heated at reflux overnight, then cooled to RT and diluted with $H_2O$ and EtOAc and separated. The aqueous phase was washed with EtOAc and the combined extracts were washed with brine, dried ($Na_2SO_4$), and concentrated under reduced pressure. The crude was dissolved in AcOH and NaOAc (2 eq) was added. The resulting solution was heated at reflux for 1 hr. The reaction mixture was cooled and the mixture was extracted with EtOAc. The organic phase was washed twice with brine, dried ($Na_2SO_4$) and the solvent removed under reduced pressure. The residue was taken up in $H_2O$ and to the resulting suspension was added an aqueous solution of 23 M NaOH (8 eq) and heated to 90° C. for 30 min. The reaction solution was cooled then acidified to pH 4 with 2 M HCl. The mixture stirred for 10 min and filtered. The resulting solid was washed sequentially with $H_2O$, hexanes, $Et_2O$, EtOAc and dried under high vacuum to give the title compound as a pale orange powder.

$^1$H NMR (300 MHz, DMSO-d6) δ: 13.30 (0.5H, br. s), 12.74 (1H, s), 7.78-7.75 (1H, m), 7.53 (1H, m), 7.31-7.25 (1H, m), 7.72 (1H, s), 3.94 (2H, s), 2.45 (2H, J=7.5 Hz), 1.11 (3H, t, J=7.5 Hz). MS (ES) $C_{14}H_{13}FN_2O_3$ required: 276. found: 277 (M+H)$^+$.

Step 3: 4-{5-[(5-Ethyl-6-oxo-1,6-dihydropyridazin-3-yl)methyl]-2-fluorobenzoyl}-1,4-diazepan-1-ium Trifluoroacetate (A4)

To a solution of A3 (1 eq) in DMA was added HBTU (2 eq), tert-butyl 1-homo-piperazinecarboxylate (1.9 eq), and DIPEA (3.4 eq). The mixture was stirred overnight at RT and then the reaction mixture was concentrated, the crude was dissolved in DCM, and washed twice with H$_2$O, dried (Na$_2$SO$_4$) and concentrated under reduced pressure. The resulting orange oil was dissolved in a mixture of 6 M HCl/ EtOH (2:1) and the mixture stirred at RT for 1 h. The solution was concentrated, basified with conc. NH$_3$ aq. solution to pH 9, and then the organics were extracted with DCM. The combined organic fractions were washed with H$_2$O, brine, dried (Na$_2$SO$_4$) and the solvent removed under reduced pressure. The residue was purified by preparative RP-HPLC, using H$_2$O (0.1% TFA) and MeCN (0.1% TFA) as eluents (column: Water X-Terra C18) and the pooled product fractions were lyophilized to give the title compound as a colourless powder. $^1$H NMR (300 MHz, DMSO-d6) δ: 12.76 (1H, s), 8.79 (2H, br. s), 7.45-7.27 (3H, m), 7.19 (1H, s), 3.93 (2H, s), 3.85-3.74 (2H, m), 3.56 (1H, m), 3.39-3.20 (5H, m), 2.45 (2H, J=7.5 Hz), 2.08-1.91 (2H, m), 1.11 (3H, t, J=7.5 Hz). MS (ES) C$_{19}$H$_{23}$FN$_4$O$_2$ required: 358. found: 359 (M+H)$^+$.

Example 2

4-{5-[(4-Ethyl-6-oxo-1,6-dihydropyridazin-3-yl) methyl]-2-fluorobenzoyl}-1,4-diazepan-1-ium Trifluoroacetate (B3)

Step 1: 5-[(6-chloro-4-ethylpyridazin-3-yl)methyl]-2-fluorobenzoic Acid (B1)

A solution of Example 1, A2 (1 eq) in AcOH:conc.HCl: H$_2$O (1:10:1, 0.065 M) was heated at reflux overnight. The reaction mixture was then cooled down to RT and diluted with water/EtOAc. The organic phase was washed with brine, dried (Na$_2$SO$_4$), and concentrated under reduced pressure. MS (ES) C$_{14}$H$_{12}$ClFN$_2$O$_2$ required: 294/296. found: 295/297 (M+H)$^+$.

Step 2: 4-{5-[(6-chloro-4-ethylpyridazin-3-yl)methyl]-2-fluorobenzoyl}-1,4-diazepan-1-ium Trifluoroacetate (B2)

To a solution of B1 (1 eq) in DMA was added HBTU (2 eq), tert-butyl 1-homopiperazinecarboxylate (2 eq) and DIPEA (3.1 eq) and the mixture stirred overnight at RT. The reaction mixture was concentrated under reduced pressure and the crude was dissolved in DCM, washed with H$_2$O (2×), dried (Na$_2$SO$_4$), and the solvent removed under reduced pressure. The resulting crude was dissolved in a solution of 6M HCl: EtOH (3:1) and the mixture stirred at RT for 2 h. The reaction solution was concentrated, basified with aqueous ammonia to pH 9 and the mixture was extracted with DCM. The combined organic fractions were washed with water, brine, dried (Na$_2$SO$_4$) and concentrated under reduced pressure. The residue was purified by preparative RP-HPLC, using H$_2$O (0.1% TFA) and MeCN (0.1% TFA) as eluents (column: Water X-Terra C18). The pooled product fractions were lyophilized to give the title compound as yellow oil. MS (ES) C$_{19}$H$_{22}$ClFN$_4$O required: 376/378. found: 377/379 (M+H)$^+$.

Step 3: 4-{5-[(4-ethyl-6-oxo-1,6-dihydropyridazin-3-yl)methyl]-2-fluorobenzoyl}-1,4-diazepan-1-ium Trifluoroacetate (B3)

A mixture of B2, NaOAc (2 eq) and AcOH (0.16 M) was heated at reflux for 4 h. The reaction mixture was cooled down to RT and concentrated under reduced pressure. The crude was purified by preparative RP-HPLC, using H$_2$O (0.1% TFA) and MeCN (0.1% TFA) as eluents (column: Water X-Terra C18). The pooled product fractions were lyophilized to give the title compound. $^1$H NMR (600 MHz, DMSO-d6) δ: 12.80 (1H, m), 8.84 (2H, s), 7.38-7.28 (3H, m), 6.66 (1H, s), 4.01 (2H, s), 3.85-3.7 (2H, m), 3.55 (1H, m), 3.36-3.32 (2H, m), 3.27 (1H, m), 3.20 (1H, m), 3.16 (1H, m), 2.45-2.42 (2H, m), 2.06 (1H, m), 1.90 (1H, m), 1.11-1.07 (3H, m). MS (ES) C$_{19}$H$_{23}$FN$_4$O$_2$ required: 358. found: 359 (M+H)$^+$.

Example 3

6-{3-[(4-Acetyl-1,4-diazepan-1-yl)carbonyl]-4-fluorobenzyl}-4-ethylpyridazin-3(2H)-one (C1)

To a solution Example 1, A4 (1 eq) in DCM:DMF (2:1, 0.5 M), it was added DIPEA (3 eq), followed by AcCl (1.2 eq). After stirring 30 min at RT, the solvent was removed under reduced pressure and the crude redissolved in EtOAc, washed with 1M HCl, dried (Na$_2$SO$_4$), and concentrated under reduced pressure. The resulting crude was dissolved in THF: H$_2$O (1:1) and LiOH (2 eq) was added, after stirring for 40 min at RT the reaction mixture was extracted with EtOAc. The combined organic fractions were washed with brine, dried (Na$_2$SO$_4$) and concentrated under reduced pressure, to afford the title compound as yellow powder. $^1$H NMR (400 MHz, DMSO-d6) δ: 12.6 (1H, s), 7.38 (1H, m), 7.28-7.17 (3H, m), 3.92 (2H, m), 3.82-3.66 (3H, m), 3.60-3.48 (3H, m), 3.43-3.30 (2H, m), 2.46 (2H, q, J=7.3 Hz), 2.05 (1.5H, s), 1.89 (1.5H, s), 1.88-1.49 (2H, m), 1.12 (3H, t, J=7.3 Hz). MS (ES) C$_{21}$H$_{25}$FN$_4$O$_3$ required: 400. found: 401 (M+H)$^+$.

Example 4

1-Acetyl-4-{5-[(6-chloro-4-ethylpyridazin-3-yl)methyl]-2-fluorobenzoyl}-1,4-diazepane (D1)

The title compound was prepared as described in Example 3 from Example 2, B3. It was obtained as white powder. $^1$H NMR (400 MHz, DMSO-d6) δ: 12.78 (1H, s), 7.32-7.14 (3H, m), 6.65 (1H, s), 4.01-3.99 (2H, m), 3.79-3.63 (3H, m), 3.53-3.48 (3H, m), 3.40-3.27 (2H, m), 2.48-2.41 (2H, m), 2.04-2.02 (3H, m), 1.86-1.78 (1H, m), 1.55-1.46 (1H, m), 1.11-1.06 (3H, m). MS (ES) C$_{21}$H$_{25}$FN$_4$O$_3$ required: 400. found: 401 (M+H)$^+$.

Example 5

4-Ethyl-6-(4-fluoro-3-{[3-(trifluoromethyl-5,6-dihydro[1,2,4]triazolo[4,3-a]pyrazin-7(8H)-yl] carbonyl}benzyl)pyridazin-3(2H)-one (E1)

To a solution of Example 1, A3 (1 eq) in DMF (0.2 mL, 0.28 M) was added HBTU (1.2 eq) and DIPEA (1 eq). The resulting solution stirred 10 min at RT. Then, it was added a solution of 3-(trifluoromethyl)-5,6,7,8-tetrahydro[1,2,4]triazolo[4,3-a]pyrazin-7-ium chloride (PTC Int. Appl., WO 2005020929) (1.1 eq) and DIPEA (1.2 eq) in DMF (0.2 mL, 0.28 M). The reaction mixture stirred overnight at RT. The crude was purified by preparative RP-HPLC, using H$_2$O (0.1% TFA) and MeCN (0.1% TFA) as eluents. The product fractions were lyophilized to give the title compound as a white powder. $^1$H NMR (300 MHz, DMSO-d$_6$) δ: 12.74 (1H, s), 7.47-7.31 (3H, m), 7.20 (1H, s), 5.11-5.09 (1.4H, m), 4.77-4.75 (0.7H, m), 4.27-4.18 (2.6H, m), 3.94 (2H, s), 3.80-3.78 (1.3H, m), 2.44

(2H, q, j=7.3 Hz), 1.11 (3H, t, j=7.3 Hz). MS (ES) $C_{20}H_{18}F_4N_6O_2$ required: 450. found: 451 (M+H)$^+$.

Example 6

4-{5-[(5-Ethyl-4-methyl-6-oxo-1,6-dihydropyridazin-3-yl)methyl]-2-fluorobenzoyl}-1,4-diazepan-1-ium trifluoroacetate (F8) and 4-{5-[(4-ethyl-5-methyl-6-oxo-1,6-dihydropyridazin-3-yl)methyl]-2-fluorobenzoyl}-1,4-diazepan-1-ium Trifluoroacetate (F9)

Step 1: 3,6-Dichloro-4-ethyl-5-methylpyridazine (F1)

To a suspension of 3,6-dichloro-4-ethylpyridazine (1 eq), AgNO$_3$ (0.7 eq) and AcOH (2.8 eq) in H$_2$O (9.4 mL, 0.6M) was added a solution of conc, sulfuric acid (6.6 eq) in H$_2$O (9.4 mL, 0.6 M) at 50° C., followed by addition of a solution ammonium peroxodisulfate (5.4 eq) in H$_2$O (9.4 mL, 0.6 M) at 60° C. for 20 min. The reaction mixture was heated at 70-75° C. for 30 min. After cooling, the reaction mixture was adjusted to pH 7 with a 25% ammonium hydroxide solution, and extracted with Et$_2$O. The extracts were washed with H$_2$O and dried (Na$_2$SO$_4$) and solvent was removed under high vacuum. The residue was purified by silica gel chromatography, eluting with 9:1 petroleum ether:EtOAc, to afford the desired product as colourless crystals. $^1$H NMR (400 MHz, CDCl$_3$) δ: 2.85 (2H, q, J=7.6 Hz), 2.45 (3H, s), 1.21 (3H, t, J=7.6 Hz).

Step 2: 5-[(6-Chloro-5-ethyl-4-methylpyridazin-3-yl)(cyano)methyl]-2-fluorobenzonitrile (F2) and 5-[(6-chloro-4-ethyl-5-methylpyridazin-3-yl)(cyano)methyl]-2-fluorobenzonitrile (F3)

The title compounds were prepared as described in Example 1, A1 and A2. It was obtained an isomeric mixture (ratio 1:1), whose isomers were not able to be separated by silica gel chromatography (eluents petroleum ether:EtOAc, 7:3). $^1$H NMR (300 MHz, CDCl$_3$) δ: 7.77-7.67 (4H, m), 7.32-7.27 (2H, s), 5.76-5.72 (2H, m), 2.84 (2H, q, J=7.5 Hz), 2.71-2.69 (2H, m), 2.44 (3H, s), 2.31 (3H, s), 1.21 (3H, t, J=7.5 Hz), 1.06 (3H, t, J=7.5 Hz). MS (ES) $C_{16}H_{12}ClFN_4$ requires: 314/316. found: 315/317 (M+H)$^+$.

Step 3: 5-[(5-Ethyl-4-methyl-6-oxo-1,6-dihydropyridazin-3-yl)methyl]-2-fluorobenzoic Acid (F4) 5-[(4-ethyl-5-methyl-6-oxo-1,6-dihydropyridazin-3-yl)methyl]-2-fluorobenzoic Acid (F5)

The title compounds were prepared as described in Example 1, A3 from mixture F2 and F3 and the desired products obtained a mixture of isomers F4 and F5. MS (ES) $C_{15}H_{15}FN_2O_3$ required: 290. found: 291 (M+H)$^+$.

Step 4: tert-Butyl 4-{5-[(5-ethyl-4-methyl-6-oxo-1,6-dihydropyridazin-3-yl)methyl]-2-fluorobenzoyl}-1,4-diazepane-1-carboxylate (F6) and tert-butyl 4-{5-[(4-ethyl-5-methyl-6-oxo-1,6-dihydropyridazin-3-yl)methyl]-2-fluorobenzoyl}-1,4-diazepane-1-carboxylate (F7)

To a solution of F4 and F5 (1 eq) in DMA was added HBTU (1.2 eq), tert-butyl 1-homo-piperazinecarboxylate (1.4 eq), and DIPEA (3 eq). The reaction mixture stirred 1 hr at RT. The crude was purified by preparative RP-HPLC, using H$_2$O (0.1% TFA) and MeCN (0.1% TFA) as eluents and the pooled product fractions were lyophilized to give the title compounds as an isomeric mixture 1.6:1. MS (ES) $C_{25}H_{33}FN_4O_4$ required: 472. found: 473 (M+H)$^+$.

Step 4: 4-{5-[(5-ethyl-4-methyl-6-oxo-1,6-dihydropyridazin-3-yl)methyl]-2-fluorobenzoyl}-1,4-diazepan-1-ium trifluoroacetate (F8) and 4-{5-[(4-ethyl-5-methyl-6-oxo-L6-dihydropyridazin-3-yl)methyl]-2-fluorobenzoyl}-1,4-diazepan-1-ium Trifluoroacetate (F9)

The mixture F6 and F7 was dissolved in a solution of TFA:CH$_2$Cl$_2$ (1:2, 2.1 mL) and the resulting solution stirred 1 hr at RT. The solvent was concentrated and the residue was dissolved in MeCN:H$_2$O, frozen and then lyophilized. The title compounds were obtained as a mixture of (F8:F9 ratio: 0.42/0.58). $^1$H NMR (400 MHz, DMSO-d$_6$) δ: 12.70-12.67 (1H, m), 8.86 (2H, s), 7.36-7.21 (3H, m), 3.95 (2H, s), 3.90-3.55 (2H, m), 3.54-3.04 (6H, m), 2.45-2.40 (2H, m), 2.02 (3H, s), 1.99 (2H, s), 1.02-0.92 (1.7H, m, major product), 0.91-081 (1.3H, m, minor product), MS (ES) $C_{20}H_{26}FN_4O_2$ required: 372. found: 373 (M+H)$^+$.

Example 7

4-{2-Fluoro-5[(5-isopropyl-6-oxo-1,6-dihydropyridazin-3-yl)methyl]benzoyl}-1,4-diazepan-1-ium Trifluoroacetate (G3)

Step 1: 5-[(6-Chloro-5-isopropylpyridazin-3-yl)(cyano)methyl]-2-fluorobenzonitrile (G1)

To an ice-cold solution of 5-(cyanomethyl)-2-fluorobenzonitrile (1 eq) and 3,6-dichloro-4-isopropylpyridazine (1.3 eq) (Reference: Org. Prep.+Proc. Int. 1988, 20, 117 and U.S. Pat. No. 4,628,088, 1986) in THF (38 mL, 0.1 M) was added portionwise NaH (1 eq). The reaction was stirred at 0° C. for 15 min and then warmed to RT and stirred for 2 hrs. The reaction was quenched with a sat. aq. NaHCO$_3$ and extracted with EtOAc. The combined organic fractions were washed with brine, dried (Na$_2$SO$_4$) and concentrated under reduced pressure. The crude was purified by silica gel chromatography, eluting with petroleum ether:EtOAc (8:2) to afford the title compound. $^1$H NMR (400 MHz, CDCl$_3$) δ: 7.80-7.79 (2H, m), 7.49 (1H, s), 7.31-7.29 (1H, m), 5.63 (1H, s), 3.34-3.28 (1H, m), 1.36-1.29 (6H, m). MS (ES) $C_{16}H_{12}ClFN_4$ required: 314/316. found: 315/317 (M+H)$^+$.

Step 2: 2-Fluoro-5-[(5-isopropyl-6-oxo-1,6-dihydropyridazin-3-yl)methyl]benzoic Acid (G2)

The title compound was prepared as described in Example 1, A3. MS (ES) $C_{15}H_{15}FN_2O_3$ required: 290. found: 291 (M+H)$^+$.

Step 3: 4-{2-Fluoro-5-[(5-isopropyl-6-oxo-1,6-dihydropyridazin-3-yl)methyl]benzoyl}-1,4-diazepan-1-ium Trifluoroacetate (G3)

The title compound was prepared as described Example 6 steps 4+5. The title compound was obtained as yellow powder. $^1$H NMR (400 MHz, DMSO-d$_6$) δ: 12.76 (1H, s), 8.74 (2H, br. s), 7.45-7.28 (3H, m), 7.19-7.17 (1H, m), 3.94 (2H, s), 3.86-3.73 (2H, m), 3.55-3.18 (6H, m), 3.02-3.00 (1H, m), 2.07-1.90 (2H, m), 1.15-1.12 (6H, m). MS (ES) $C_{20}H_{25}FN_4O_2$ required: 372. found: 373 $(M+H)^+$.

Example 8

4-{5-[(4,5-Dimethyl-6-oxo-1,6-dihydropyridazin-3-yl)methyl]-2-fluorobenzoyl}-1,4-diazepan-1-ium Trifluoroacetate (H2)

Step 1: tert-Butyl4-{5-[(4,5-dimethyl-6-oxo-1,6-dihydropyridazin-3-yl)methyl]-2-fluorobenzoyl}-1,4-diazepane-1-carboxylate (H1)

To a solution of Example 14, N4 (1 eq) in DMA (3.7 mL, 0.4M) was added HBTU (1.2 eq), tert-butyl 1-homo-piperazinecarboxylate (1.4 eq), and DIPEA (3 eq). The reaction mixture stirred 1 hr at RT. The reaction was quenched with a sat. aq. NaHCO$_3$ and extracted with CH$_2$Cl$_2$. The combined organic fractions were washed with brine, dried (Na$_2$SO$_4$) and concentrated under reduced pressure. The crude was purified by preparative RP-HPLC, using H$_2$O (0.1% TFA) and MeCN (0.1% TFA) as eluents, and the pooled product fractions were lyophilized to give the title compound. $^1$H NMR (300 MHz, DMSO-d$_6$) δ: 12.69 (1H, s), 7.31-7.07 (3H, m), 4.00-3.98 (2H, m), 3.72-3.54 (3H, m), 3.39-3.35 (4H, m), 3.29-3.27 (1H, m), 2.03 (6H, br. s), 1.79-1.77 (1H, m), 1.50-1.48 (1H, m), 1.42 (7.7H, s), 1.31 (2.3H, s). MS (ES) $C_{24}H_{31}FN_4O_4$ required: 458. found: 459 $(M+H)^+$.

Step 2: 4-{5-[(4,5-Dimethyl-6-oxo-1,6-dihydropyridazin-3-yl)methyl]-2-fluorobenzoyl}-1,4-diazepan-1-ium Trifluoroacetate (H2)

The title compound was prepared as described in Example 6 step 5 and obtained as a yellow powder. $^1$H NMR (400 MHz, DMSO-d$_6$) δ: 12.73 (1H, s), 8.11 (2H, br. s), 7.36-7.26 (3H, m), 4.00 (2H, s), 3.85-3.54 (2H, m), 3.37-3.20 (6H, m), 2.05-2.03 (7H, m), 1.90-1.88 (1H, m). MS (ES) $C_{19}H_{23}FN_4O_2$ required: 358. found: 359 $(M+H)^+$.

Example 9

1-(4-{5-[4,5-Dimethyl-6-oxo-1,6-dihydropyridazin-3-yl)methyl]-2-fluorobenzoyl}piperazin-1-yl)-N,2-dimethyl-1-oxopropan-2-aminium Trifluoroacetate (I2)

Step 1: 4-{5-[(4,5-Dimethyl-6-oxo-L6-dihydropyridazin-3-methyl]-2-fluorobenzoyl}piperazin-1-ium Trifluoroacetate (I1)

To a solution of intermediate Example 14, N4 (1 eq) in DMF (0.97 mL, 0.4 M) was added HBTU (1.2 eq) and DIPEA (5 eq). After 10 min at RT, it was added the tert-butyl 1-piperazinecarboxylate (1.2 eq) and the reaction solution stirred overnight at RT. The reaction was quenched with a sat. aq. NaHCO$_3$ and extracted with CH$_2$Cl$_2$. The organic phase was washed once with 1 N HCl and brine. The combined organic fractions were washed with brine, dried (Na$_2$SO$_4$) and concentrated under reduced pressure. The crude was dissolved in a solution of TFA:CH$_2$Cl$_2$ (1:2, 3.4 mL) and the resulting solution stirred 1 hr at RT. The solvent was removed to dryness and the crude was purified by preparative RP-HPLC, using H$_2$O (0.1% TFA) and MeCN (0.1% TFA) as eluents (column: Water X-Terra C18). The product fractions were lyophilized to give the title compound as yellow crystals. $^1$H NMR (400 MHz, DMSO-d$_6$) δ: 12.71 (1H, s), 8.92 (2H, br. s), 7.32-7.30 (3H, m), 4.00 (2H, s), 3.86-3.84 (2H, m), 3.46-3.44 (2H, m), 3.25-3.23 (2H, m), 3.11-3.09 (2H, m), 2.05 (3H, s), 2.04 (3H, s). MS (ES) $C_{18}H_{21}FN_4O_2$ required: 344. found: 345 $(M+H)^+$.

Step 2: 1-(4-{5-[(4,5-Dimethyl-6-oxo-1,6-dihydropyridazin-3-yl)methyl]-2-fluorobenzoyl}piperazin-1-yl)-M2-dimethyl-1-oxopropan-2-aminium Trifluoroacetate (I2)

The N—BOC—N,2-dimethylalanine (3 eq), HATU (3 eq) and DIPEA (3 eq) were dissolved in DMF (40 μL, 0.1 M). After 10 min at RT, it was added a solution of I1 and DIPEA (1.2 eq) in DMF (0.1 mL, 0.3 M). The reaction solution stirred overnight at RT. The crude was purified by preparative RP-HPLC, using H$_2$O (0.1% TFA) and MeCN (0.1% TFA) as eluents (column: Water X-Terra C18). The product fractions were lyophilized to give the title compounds as white powder. $^1$H NMR (400 MHz, DMSO-d$_6$) δ: 12.72 (1H, s), 8.84-8.82 (2H, m), 7.38-7.25 (3H, m), 4.00 (2H, s), 3.71 (4H, s), 3.59 (2H, br. s), 3.31 (2H, br. s), 2.06 (3H, s), 2.04 (3H, s), 1.58 (6H, s). MS (ES) $C_{23}H_{30}FN_5O_4$ required: 443. found: 444 $(M+H)^+$.

Example 10

8-{5-[4,5-Dimethyl-6-oxo-1,6-dihydropyridazin-3-yl)methyl]-2-fluorobenzoyl}-8-aza-1-azoniaspiro[4.5]decane Trifluoroacetate (J1)

The title compound was prepared as described in Example 9. Example 14, N4 was coupled with tert-butyl 1,8-diazaspiro[4.5]decane-1-carboxylate oxalate salt. The title compound was obtained as yellow powder. $^1$H NMR (400 MHz, DMSO-d$_6$) δ: 12.71 (1H, s), 8.73 (2H, br. s), 7.36-7.22 (3H, m), 4.15-4.11 (1H, m), 4.00 (2H, s), 3.38-3.25 (5H, m), 2.05-1.76 (14H, m). MS (ES) $C_{22}H_{27}FN_4O_2$ required: 398. found: 399 $(M+H)^+$.

Example 11

8-{5[(4,5-Dimethyl-6-oxo-1,6-dihydropyridazin-2-ium-3-yl)methyl]-2-fluorobenzoyl}-1-methyl-8-aza-1-azoniaspiro[4.5]decane bis(trifluoroacetate) (K1)

To a solution of Example 11, J1 (1 eq) in MeOH (0.5 mL, 0.1 M) was added TEA (2.2 eq) until pH 6-7. Then it was added the formaldehyde (10 eq, 37% in H$_2$O), NaBH$_3$(CN) (8 eq) and NaOAc (2.8 eq). The reaction solution stirred overnight at RT. The solvent was removed and the crude was purified by preparative RP-HPLC, using H$_2$O (0.1% TFA) and MeCN (0.1% TFA) as eluents. The pooled product fractions were lyophilized to give the title compound. The major rotamer showed $^1$H NMR (400 MHz, DMSO-d$_6$) δ: 12.72 (1H, br. s), 9.63 (1H, br. s), 7.36-7.24 (3H, m), 4.63-4.60 (1H, m), 4.00 (2H, s), 3.61 (1H, br. s), 3.49-3.42 (1H, m), 3.23-3.17 (2H, m), 2.98-2.84 (1H, m), 2.75-2.73 (2H, m) 2.58 (3H, s), 2.40-2.31 (1H, m), 2.04 (6H, s), 1.97-1.79 (4H, m), 1.63-1.60 (1H, m). MS (ES) $C_{23}H_{29}FN_4O_2$ required: 412. found: 413 $(M+H)^+$.

Example 12

4-[(4,5-Dimethyl-6-oxo-1,6-dihydropyridazin-3-yl) methyl]-N,N-dimethyl-2-{[3-(trifluoromethyl)-5,6-dihydro[1,2,4]triazolo[4,3-a]pyrazin-7(8H)-yl] carbonyl}benzenaminium Trifluoroacetate (L3)

Step 1: 2-(Dimethylamino)-5-[(4,5-dimethyl-6-oxo-1,6-dihydropyridazin-3-yl)methyl]benzonitrile (L1)

A solution of Example 14, N3 (1 eq) and dimethylamine (4 eq, 2 M in MeOH) in dry DMF (2.7 mL, 0.1 M) was sealed in a microwave vial. The reaction solution was heated to 180° C. and stirred for 1.5 hrs. Then, the solution was cooled to RT and the solvent evaporated under high vacuum. The crude was purified by SCX cartridge. The title compound was washed off with a solution of 2 M $NH_3$ in methanol and concentrated under reduced pressure. $^1H$ NMR (300 MHz, DMSO-$d_6$) δ: 12.67 (1H, br. s), 7.45 (1H, s), 7.33 (1H, d, J=8.4 Hz), 7.03 (1H, d, J=8.4 Hz), 3.90 (2H, s), 2.97 (6H, s), 2.05 (3H, s), 2.03 (3H, s). MS (ES) $C_{16}H_{18}N_4O$ required: 282. found: 283 (M+H)$^+$.

Step 2: 2-(Dimethylamino)-5-[(4,5-dimethyl-6-oxo-1,6-dihydropyridazin-3-methyl]benzoic Acid (L2)

L1 (1 eq) was taken up in $H_2O$ (0.4 mL, 0.7 M) and to the resulting suspension was added an aqueous solution of 15 M NaOH (8 eq) and heated to reflux temperature for 72 hrs. The reaction solution was cooled to RT and acidified to pH 4 with 2 M HCl. The crude was purified by SCX cartridge. The title product was washed off with a solution of 2 M ammonia in methanol and concentrated under reduced pressure. MS (ES) $C_{16}H_{19}N_3O_3$ required: 301. found: 302 (M+H)$^+$.

Step 3: 4-[(4,5-Dimethyl-6-oxo-1,6-dihydropyridazin-3-yl)methyl]-N,N-dimethyl-2-{[3-(trifluoromethyl) 5,6-dihydro[1,2,4]triazolo[4,3-a]pyrazin-7 (8H)-yl]-carbonyl}benzenaminium Trifluoroacetate (L3)

The L2 (1 eq), TBTU (1.1 eq) and DIPEA (1 eq) was dissolved in DMF (0.6 mL, 0.2 M) and the solution stirred 10 min at RT. Then, it was added a solution of 3-(trifluoromethyl)-5,6,7,8-tetrahydro[1,2,4]triazolo[4,3-a]pyrazin-7-ium chloride (PTC Int. Appl., WO 2005020929) (1.1 eq) and DIPEA (1.2 eq) in DMF (0.3 mL, 0.2 M). The reaction mixture stirred overnight at RT. The crude was purified by preparative RP-HPLC, using $H_2O$ (0.1% TFA) and MeCN (0.1% TFA) as eluents (column: Water X-Terra C18). The pooled product fractions were lyophilized to afford the title compound as yellow powder. $^1H$ NMR (400 MHz, DMSO-$d_6$) δ: 12.67 (1H, br. s), 7.24-7.07 (3H, m), 5.07-5.05 (1H, m), 4.58 (1H, br. s), 4.26-4.13 (3H, m), 3.92 (2H, s), 2.75 (3H, s), 2.5 (3H, solvent peak), 2.03 (6H, s). MS (ES) $C_{22}H_{24}F_3N_7O_5$ required: 475. found: 476 (M+H)$^+$.

Example 13

6-(4-Isopropoxy-3-{[3-(trifluoromethyl)-5,6-dihydro[1,2,4]triazolo[4,3-a]pyrazin-7(8H)-yl] carbonyl}benzyl)-4,5-dimethyl-3-oxo-2,3-dihydropyridazin-1-ium Trifluoroacetate) (M3)

Step 1: 5-[(4,5-Dimethyl-6-oxo-1,6-dihydropyridazin-3-yl)methyl]-2-isopropoxybenzonitrile (M1)

A solution of sodium isoproxide was prepared by reacting sodium (2.5 eq) with dry 2-propanol (3 mL, 0.03 M), to this was added a solution of Example 14, N3 (1 eq) in dry 2-propanol (2.4 mL, 0.02 M). The resulting solution was heated to reflux temperature and it stirred for 5 hrs. The reaction solution was cooled to RT and the solvent evaporated under high vacuum. The crude was dissolved in EtOAc. The organic phase was washed twice with water, dried (Na$_2$SO$_4$) and solvent evaporated to dryness. MS (ES) $C_{17}H_{19}N_3O_2$ required: 297. found: 298 (M+H)$^+$.

Step 2: 5-[(4,5-Dimethyl-6-oxo-1,6-dihydropyridazin-3-yl)methyl]-2-isopropoxybenzoic Acid (M2)

M1 (1 eq) was taken up in $H_2O$ (0.3 mL, 0.7 M) and to the resulting suspension was added an aqueous solution of 15 M NaOH (8 eq) and heated to reflux temperature for 48 hrs. The reaction solution was cooled to RT and acidified to pH 4 with 2 M HCl. The crude was purified by SAX cartridge. The title product was washed off with a solution of 2 M HCl in methanol and the solvent concentrated under reduced pressure. MS (ES) $C_{17}H_{20}N_2O_4$ required: 316. found: 317 (M+H)$^+$.

Step 3: 6-(4-Isopropoxy-3-{[3-(trifluoromethyl) 5,6-dihydro[1,2,4]triazolo[4,3-a]pyrazin-7(8H)-yl] carbonyl}benzyl)-4,5-dimethyl-3-oxo-2,3-dihydropyridazin-1-ium Trifluoroacetate) (M3)

The title compound was prepared as described in Example 12 step 3 and obtained as a white powder. $^1H$ NMR (400 MHz, DMSO-$d_6$) δ: 12.70 (1H, s), 7.26-7.24 (1H, m), 7.13-7-05 (2H, m), 5.23-5.19 (0.4H, m), 4.93-4.88 (0.4H, m), 4.65-4.63 (1.6H, m), 4.54-4.25 (1.6H, m), 4.16-4.10 (2H, m), 3.93-3.87 (3H, m), 2.05-2.03 (6H, m), 1.26-1.21 (3H, m), 1.00-0.92 (3H, m). MS (ES) $C_{23}H_{25}F_3N_6O_3$ required: 490. found: 491 (M+H)$^+$.

Example 14

6-(4-Fluoro-3-{[3-(trifluoromethyl)-5,6-dihydro[1,2,4]triazolo[4,3-a]pyrazin-7(8H)-yl]carbonyl}benzyl)-4,5-dimethylpyridazin-3(2H)-one

Step 1: 5-[(6-Chloro-4,5-dimethylpyridazin-3-yl) (cyano)methyl]-2-fluorobenzonitrile (N1)

The procedure followed the one described in Example 1 step 1, starting from 3,6-dichloro-4,5-dimethylpyridazinone (prepared according *J. Org. Chem.* 1955, 20, 707-13). $^1H$ NMR (300 MHz, DMSO-$d_6$) δ: 8.05-7.96 (1H, m), 7.95-7.82 (1H, m), 7.70-7.61 (1H, m), 6.48 (1H, s), 2.41 (3H, s), 2.29 (3H, s). MS (ES) $C_{15}H_{10}ClFN_4$ required: 300. found: 301 (M+H)$^+$.

Step 2: 5-[(6-Chloro-4,5-dimethylpyridazin-3-yl)methyl]-2-fluorobenzonitrile (N2)

Intermediate N1 was suspended in a mixture of acetic acid, conc. aq. HCl and water (1:1:2, 0.07M). The suspension was stirred and heated at reflux for 75 min. The reaction mixture was cooled to RT and the solvents were removed under reduced pressure. To the residue was added saturated aq. NaHCO$_3$ and the mixture was extracted with EtOAc. The organic phase was dried (Na$_2$SO$_4$), filtered and concentrated to dryness. The residue was purified by column chromatography on silica gel, eluting with PE-EtOAc (10-80% EtOAc)

to afford the title compound as a yellow solid. MS (ES) $C_{14}H_{11}ClFN_3$ required: 275. found: 276 (M+H)$^+$.

Step 3: 5-[(4,5-Dimethyl-6-oxo-1,6-dihydropyridazin-3-yl)methyl]-2-fluorobenzonitrile (N3)

To a solution of intermediate N2 in acetic acid (0.16 M) was added NaOAc (2 eq.) and the mixture was stirred and heated to reflux for 1 h. The solution was cooled to RT and the solvent was removed under reduced pressure. The residue was suspended in water and triturated until a fine suspension was obtained. The solid material was filtered off, washed with water, dried by air stream and then under high vacuum. MS (ES) $C_{14}H_{12}FN_3O$ required: 257. found: 258 (M+H)$^+$.

Step 4: 5-[(4,5-Dimethyl-6-oxo-1,6-dihydropyridazin-3-yl)methyl]-2-fluorobenzoic Acid (N4)

To a suspension of intermediate N3 in water (0.35 M) was added NaOH (8 eq.) and the resulting mixture was stirred and heated to 100° C. for 60 min. The mixture was cooled with an ice bath and slowly acidified to pH 2-3 with 6N HCl. The formed light yellow precipitate was filtered off, dried under air stream and then under high vacuum. MS (ES) $C_{14}H_{13}FN_2O_3$ required: 276. found: 277 (M+H)$^+$.

Step 5: 6-(4-Fluoro-3-{[3-(trifluoromethyl)-5,6-dihydro[1,2,4]triazolo[4,3-a]pyrazin-7(8H)-yl]carbonyl}benzyl)-4,5-dimethylpyridazin-3(2H)-one (N5)

Intermediate N4 (1 eq), TBTU (2 eq) and DIPEA (1.1 eq) was dissolved in DMF (1.1 mL, 0.2M) and the solution stirred 10 min at RT. Then a solution of 3-(trifluoromethyl)-5,6,7,8-tetrahydro[1,2,4]triazolo[4,3-a]pyrazin-7-ium chloride (PTC Int. Appl., WO 2005020929) (2.2 eq) and DIPEA (1.2 eq) in DMF (1.4 mL, 0.2 M) was added. The reaction mixture stirred 5 hrs at RT. The reaction mixture was diluted with EtOAc and washed twice with brine. The organic phase was dried (Na$_2$SO$_4$) and concentrated under reduced pressure. The crude was purified by preparative RP-HPLC, using H$_2$O (0.1% TFA) and MeCN (0.1% TFA) as eluents. The product fractions were lyophilized and the resulting trifluoroacetic salt was partitioned between EtOAc and a sat. aq. sol. of NaHCO$_3$. The organic phase was dried (Na$_2$SO$_4$) and the solvent evaporated to dryness. The title compound was obtained as white powder. $^1$H NMR (400 MHz, DMSO-d$_6$) δ: 12.70 (1H, s), 7.42-7.31 (3H, m), 5.09 (1H, br. s), 4.75 (1H, br. s), 4.28 (1H, br. s), 4.16 (2H, br. s), 4.01 (2H, s), 3.78-3.76 (1H, m), 2.05-2.03 (6H, m). MS (ES) $C_{20}H_{18}F_4N_6O_2$ required: 450. found: 451 (M+H)$^+$.

Example 15

6-(4-Fluoro-3-{[4-(2-methylprolyl)piperazin-1-yl]carbonyl}benzyl)-4,5-dimethylpyridazin-3(2H)-one A mixture of 1-(tert-butoxycarbonyl)-2-methylproline (1 eq), TEA (2 eq), PyBOP (1 eq) and 6-[4-fluoro-3-(piperazin-1-ylcarbonyl)benzyl]-4,5-dimethylpyridazin-3(2H)-one (II) in dry DMF (0.1 M) was heated at 60° C. with microwaves irradiation for 2 hours. The product was isolated by preparative-HPLC. After lyophilization of the pooled product fractions the residue was dissolved in 10% TFA/DCM and the solution was warmed to 45° C. for 1 h. The residue obtained after solvent evaporation was further purified by SCX cartridge. Lyophilization from water/MeCN afforded the title compound as a white powder. $^1$H NMR (400 MHz, DMSO-d6) δ: 12.67 (1H, s), 7.38-7.13 (3H, m), 3.96 (2H, s), 3.8-3.5 (5H, m), 3.3 (1H under water signal), 3.26-3.13 (2H, m), 2.92-2.78 (1H, m), 2.76-2.58 (1H, m), 2.34-2.15 (1H, m), 2.02 (3H, s), 2.00 (3H, s), 1.75-1.46 (3H, m), 1.26 (3H, s). MS (ES) $C_{24}H_{30}FN_5O_3$ requires: 455. found: 456 (M+H)$^+$.

Example 16

6-[4-Fluoro-3-(4-methyl-2,5-dioxoimidazolidin-1-yl)benzyl]-4,5-dimethyl-3-oxo-2,3-dihydropyridazin-1-ium Trifluoroacetate Step 1: tert-Butyl{5-[(4,5-dimethyl-6-oxo-1,6-dihydropyridazin-3-yl)methyl]-2-fluorophenyl}carbamate (O1)

To a mixture of Example 14, N4 in tert-BuOH:toluene (1:1, 0.171 M) was added diphenyl phosphoryl azide (2.2 eq) and Et$_3$N (2.2 eq). The reaction was heated at reflux until consumption of the starting material and then volatiles were removed under reduced pressure. The resulting residue was partitioned between DCM and sat. aq. NaHCO$_3$; the organic phase was separated, dried (Na$_2$SO$_4$) and filtered. Evaporation of the solvent provided yellow oil (O1) which was used as such in the next step without purification. MS (ES) $C_{18}H_{22}FN_3O_3$ required: 347. found: 348 (M+H)$^+$.

Step 2: 6-(3-{[N-(Ethoxycarbonyl)alanyl]amino}-4-fluorobenzyl)-4,5-dimethyl-3-oxo-2,3-dihydropyridazin-1-ium Trifluoroacetate (O2)

O1 was dissolved in DCM:TFA (1:1, 0.17 M) and the mixture was stirred at RT for 1 h and then volatiles were removed under high vacuum. The resulting oil and DIPEA (2.35 eq) were added to a stirred solution of N-(ethoxycarbonyl)alanine, (1.35 eq), TBTU (1.35 eq) and DIPEA (1.35 eq) in dry DMF (0.3 M). The mixture was stirred at room temperature for 2 days and then diluted with DCM and washed with water. The organic phase was washed with brine, dried (Na$_2$SO$_4$) and concentrated under reduced pressure. The product was isolated by preparative HPLC, using MeCN/water (0.1% TFA) as eluents. The pooled product fractions were lyophilized to afford the title compound (O2) as a white fluffy powder. MS (ES) $C_{19}H_{23}FN_4O_4$ requires: 390. found: 391 (M+H)$^+$. $^1$H NMR (300 MHz, DMSO-d$_6$) δ: 12.65 (1H, s), 9.61 (1H, s), 7.76-7.65 (1H, m), 7.45-7.30 (2H, m), 7.23-7.10 (1H, m), 7.01-6.90 (1H, m), 4.27 (1H, m), 3.98 (2H, q, J=6.9 Hz), 3.90 (2H, s), 2.03-1.96 (6H, m), 1.30-1.23 (3H, m), 1.16 (3H, t, J=6.6 Hz).

Step 3: 6-[4-fluoro-3-(4-methyl-2,5-dioxoimidazolidin-1-yl)benzyl]-4,5-dimethyl-3-oxo-2,3-dihydropyridazin-1-ium Trifluoroacetate (O3)

To a solution of O$_2$ in DMF (0.1 M) was added DMAP (3 eq) and the mixture was heated in a microwave oven at 180° C. for 2 h. The product was isolated by purification at prep RP-HPLC using H$_2$O (+0.1% TFA) and MeCN (+0.1% TFA) as eluents. The desired fractions were lyophilized to afford the desired compound. $^1$H NMR (300 MHz, DMSO-d$_6$) δ: 12.67 (1H, s), 8.52 (1H, s), 7.35-7.28 (2H, m), 7.25-7.18 (1H, m), 4.36-4.26 (1H, m), 3.97 (2H, s), 2.06-1.97 (6H, m), 1.38-1.31 (3H, m). MS (ES) $C_{17}H_{18}FN_4O_3$ requires: 344. found: 345 (M+H)$^+$.

Example 17

6-(3-{[3-[1-(Dimethylamino)-1-methylethyl]-5,6-dihydro[1,2,4]triazolo[4,3-a]pyrazin-7(8H)-yl]carbonyl}-4-fluorobenzyl)-4,5-dimethyl-3-oxo-2,3-dihydropyridazin-1-ium Trifluoroacetate

Step 1: Methyl N-(tert-butoxycarbonyl)-2-methylalaninate (P1)

To a solution of Boc-α-methylalanine in DMF (0.4 M) was added $K_2CO_3$ (1 eq) and MeI (1.2 eq). The mixture was stirred at RT for 6 h and then diluted with EtOAc, washed with water and sat. aq. $NaHCO_3$. The organic phase was dried over $Na_2SO_4$, filtered and concentrated under vacuum to provide the title compound as a yellow solid. $^1$H NMR (300 MHz, DMSO-$d_6$) δ: 7.20 (1H, br. s), 3.58 (3H, s), 1.40-1.27 (15H, m). MS (ES) $C_{10}H_{19}NO_4$ requires: 217. found: 240 (M+Na)$^+$.

Step 2: tert-Butyl (2-hydrazino-1,1-dimethyl-2-oxoethyl)carbamate (P2)

To a solution of P1 in 2-Propanol (0.56 M) was added hydrazine monohydrate (10 eq) and the mixture was stirred overnight at 90° C. Volatiles were removed under high vacuum and the obtained crude was used as such in the next step. MS (ES) $C_9H_{19}N_3O_3$ requires: 217. found: 240 (M+Na)$^+$.

Step 3: Benzyl 5-(2-{2-[(tert-butoxycarbonyl)amino]-2-methylpropanoyl}hydrazino)-3,6-dihydropyrazine-1(2H)-carboxylate (P3)

Meanwhile, $Me_3O^+BF_4^-$ (1 eq) was added to a solution of benzyl 3-oxopiperazine-1-carboxylate (1 eq) in DCM (0.85 M) and the reaction was stirred for 48 hs. P2 suspended in DCM was then added and stirring was continued for further 3 days. The mixture was diluted with DCM and washed with 1N NaOH solution. The organic layer was dried over $Na_2SO_4$, filtered and concentrated under vacuum to provide the title compound as transparent oil which was used as such in the next step. MS (ES) $C_{21}H_{31}N_5O_5$ requires: 433. found: 434 (M+H)$^+$.

Step 4: 7-[(Benzyloxy)carbonyl]-3-{1-[(tert-butoxycarbonyl)amino]-1-methylethyl}-5,6,7,8-tetrahydro[1,2,4]triazolo[4,3-a]pyrazin-1-ium Trifluoroacetate (P4)

A solution of P3 in w-BuOH was refluxed for 15 min. The solvent was removed under reduced pressure and the resulting crude was purified by Biotage system eluting with a gradient of 0-15% MeOH/DCM and then again purified by RP-prep HPLC using $H_2O$ (0.1% TFA) and MeCN (0.1% TFA) as eluents. The pooled product fractions were lyophilized to give the title compound as transparent oil. $^1$H NMR (300 MHz, DMSO-d6) δ: 7.55 (1H, br. s), 7.44-7.29 (5H, m), 5.14 (2H, br. s), 4.81 (2H, br. s), 4.08-3.97 (2H, m), 3.90-3.77 (2H, m), 1.55 (6H, br. s), 1.30 (9H, m). MS (ES) $C_{21}H_{29}N_5O_4$ required: 415. found: 416 (M+H)$^+$.

Step 5: Benzyl 3-[1-(dimethylamino)-1-methylethyl]-5,6-dihydro[1,2,4]triazolo[4,3-a]pyrazine-7(8H)-carboxylate (P5)

P4 was dissolved in DCM:TFA (1:1, 0.105 M) and the mixture was stirred at RT for 2 h. Volatiles were removed under high vacuum, the residue was dissolved in MeOH (0.1 M) and then TEA (3 eq) was added until pH=7. Formaldehyde (37% aq. sol., 10 eq), $NaBH_3(CN)$ (3 eq) and AcOH (4 eq) were added to the mixture and it was stirred at RT for 2 h. Volatiles were evaporated and the resulting crude was purified on SCX cartridge, eluting the desired product with $NH_3$/MeOH solution. After evaporation of the solvent the transparent oil was used as such in the next step. MS (ES) $C_{18}H_{25}N_5O_2$ required: 343. found: 344 (M+H)$^+$.

Step 6: N,N-Dimethyl-2-(5,6,7,8-tetrahydro[1,2,4]triazolo[4,3-a]pyrazin-3-yl)propan-2-amine (P6)

A mixture of P5 (0.12 mmol) and Pd/C (10%, 22 mg) in MeOH (0.2 M) was stirred under H2 atmosphere overnight. The catalyst was filtered off and the solvent removed under reduced pressure to provide a crude oil used as such in the next step. MS (ES) $C_{10}H_{19}N_5$ required: 209. found: 210 (M+H)$^+$.

Step 7: 6-(3-{[3-[1-(Dimethylamino-1-methylethyl]-5,6-dihydro[1,2,4]triazolo[4,3-a]pyrazin-7(8H)-yl]carbonyl}-4-fluorobenzyl)-4,5-dimethyl-3-oxo-2,3-dihydropyridazin-1-ium Trifluoroacetate (P7)

To a solution of Example 14, N4 and DIPEA (1.3 eq) in DMF (0.3 M) was added TBTU (1.3 eq). The resulting mixture was stirred at RT for 40 minutes and then P6 (1 eq) was added. Stirring was continued for 1 hour and the product was isolated by purification by preparative RP-HPLC using $H_2O$ (0.1% TFA) and MeCN (0.1% TFA) as eluents. The pooled product fractions were lyophilized to give the title compound as a white powder. $^1$H NMR (400 MHz, DMSO-d6) δ: 12.67 (1H, s), 10.12 (1H, br. s), 7.43-7.36 (1H, m), 7.35-7.23 (2H, m), 4.99 (1H, br. s), 4.66 (1H, br. s), 4.29 (1H, br. s), 3.98 (2H, s), 4.20-3.63 (3H, partially under water signal), 2.80-2.69 (6H, m), 2.04-1.97 (6H, m), 1.78-1.66 (6H, m). MS (ES) $C_{24}H_{31}FN_7O_2$ required: 467. found: 468 (M+H)$^+$.

Example 18

(2R)-2-[(4-{5-[(4,5-Dimethyl-6-oxo-1,6-dihydropyridazin-3-yl)methyl]-2-fluorobenzoyl}piperazin-1-yl)carbonyl]-2-methylazetidinium Trifluoroacetate (Q2)

Step 1: tert-Butyl (2R)-2-[(4-{5-[(4,5-dimethyl-6-oxo-1,6-dihydropyridazin-3-yl)methyl]-2-fluorobenzoyl}piperazin-1-yl)carbonyl]-2-methylazetidine-1-carboxylate (Q1)

A solution of (2R)-1-(tert-butoxycarbonyl)-2-methylazetidine-2-carboxylic acid (1.5 eq) and HATU (1.5 eq) in dry DMF (0.1M) was stirred at RT for 30 min. Then Example 14, N4 (1.0 eq) and DIPEA (1.5 eq) were added. Reaction mixture was stirred at 40° C. for 48 hrs, then diluted with EtOAc, washed sequentially with sat. aq. $NaHCO_3$ sol, 1N HCl sol and brine. The resulting solution was dried ($Na_2SO_4$), filtered and concentrated to afford the title compound which was used in the next step without further purification. MS (ES) $C_{28}H_{36}FN_5O_5$ requires: 541. found: 542 (M+H)$^+$.

Step 2

(2R)-2-[(4-{5-[(4,5-Dimethyl-6-oxo-1,6-dihydropyridazin-3-yl)methyl]-2-fluorobenzoyl}piperazin-1-yl)carbonyl]-2-methylazetidinium Trifluoroacetate (Q2)

(Q1) was dissolved in DCM/TFA solution (9/1, 0.06M) and stirred for 18 h at RT. Solvent was evaporated under reduced pressure and the crude product purified by preparative RP-HPLC using H$_2$O (0.1% TFA) and MeCN (0.1% TFA) as eluents. The desired fractions were lyophilized to afford the titled compound (Q2) as a white solid. $^1$H-NMR (400 MHz, DMSO-de, 300K) δ: 12.67 (1H, s), 9.16 (1H, br. s), 8.91 (1H, br. s), 7.35-7.17 (3H, m), 4.07-3.91 (3H, m), 3.8-3.15 (9H, m), 2.92-2.73 (1H, m), 2.60-2.25 (1H, m overlapped to the DMSO signal), 2.00 (3H, s), 1.99 (3H, s), 1.77 (1.5H, s), 1.72 (1.5H, s). MS (ES) C$_{25}$H$_{29}$F$_3$N$_5$O$_5$ requires: 441. found: 442 (M+H)$^+$.

Example 19

6-{4-fluoro-3-[(4-{[1-(isobutylamino)cyclopentyl]carbonyl}piperazin-1-yl)carbonyl]benzyl}-4,5-dimethylpyridazin-3(2H)-one Trifluoroacetate (R2)

Step 1: 6-[3-({4-[(1-aminocyclopentyl)carbonyl]piperazin-1-yl}carbonyl)-4-fluorobenzyl]-4,5-dimethylpyridazin-3(2H)-one (R1)

The desired compound was prepared following the general procedure reported in Example 18 step 1 and 2, using 1-[(tert-butoxycarbonyl)amino]cyclopentanecarboxylic acid and Example 14, N4 as starting materials. Additionally HOBT (1.3 equiv.) was added in the step 1. The product was obtained as a yellow solid after purification with a SCX cartridge. MS (ES$^+$) C$_{24}$H$_{30}$FN$_5$O$_3$ requires: 455. found: 456 (M+H)$^+$.

Step 2: 6-{4-fluoro-3-[(4-{[1-(isobutylamino)cyclopentyl]carbonyl}piperazin-1-yl)carbonyl]benzyl}-4,5-dimethylpyridazin-3(2H)-one Trifluoroacetate (R2)

R1 (1.0 eq.) and 2-methylpropanal (1.0 eq) in dry methanol (0.04M) were stirred at RT for 2 h, NaBH$_3$(CN) (1.0 eq) was added and stirred at RT for 1 h. Than water was added and the aqueous phase was extracted with EtOAc. The organic phase was dried (MgSO$_4$), filtered and solvents were removed under reduced pressure. The crude product was purified by preparative RP-HPLC using H$_2$O (0.1% TFA) and MeCN (0.1% TFA) as eluents. The desired fractions were lyophilized to afford the titled compound (CSF2) as a white solid. $^1$H-NMR (400 MHz, DMSO-d$_6$, 300K) δ: 12.66 (1H, s), 8.40 (2H, bs), 7.35-7.16 (3H, m), 3.95 (2H, s), 3.72-3.40 (6H, m), 3.28 (2H, m), 2.68 (2H, m), 2.52 (1H, m), 2.13 (4H, m), 2.08 (3H, s), 1.98 (3H, s), 1.88 (4H, m), 0.96 (6H, d, J=6.4 Hz). MS (ES) C$_{28}$H$_{38}$FN$_5$O$_3$ requires: 511. found: 512 (M+H)$^+$.

The following Examples were prepared according to the procedures described in the above Examples.

| Example | Name | MWt | [M + H]+ | Procedure Of Example |
|---|---|---|---|---|
| 20 | 2-(4-{5-[(5-Ethyl-6-oxo-1,6-dihydropyridazin-3-yl)methyl]-2-fluorobenzoyl}-1,4-diazepan-1-yl)pyrimidin-1-ium trifluoroacetate | 436 | 437 | 5 |
| 21 | 4-(1-{5-[(5-Ethyl-6-oxo-1,6-dihydropyridazin-3-yl)methyl]-2-fluorobenzoyl}piperidin-4-yl)pyridinium trifluoroacetate | 420 | 421 | 5 |
| 22 | 2-{[(1-{5-[(5-Ethyl-6-oxo-1,6-dihydropyridazin-3-yl)methyl]-2-fluorobenzoyl}piperidin-4-yl)oxy]methyl}pyridinium trifluoroacetate | 450 | 451 | 5 |
| 23 | 2-{[(1-{5-[(5-Ethyl-6-oxo-1,6-dihydropyridazin-3-yl)methyl]-2-fluorobenzoyl}piperidin-3-yl)oxy]methyl}pyridinium trifluoroacetate | 450 | 451 | 5 |
| 24 | 2-(4-{5-[(5-Ethyl-6-oxo-1,6-dihydropyridazin-3-yl)methyl]-2-fluorobenzoyl}piperazin-1-yl)-5-methoxypyridinium trifluoroacetate | 451 | 452 | 5 |
| 25 | 2-(4-{5-[(5-Ethyl-6-oxo-1,6-dihydropyridazin-3-yl)methyl]-2-fluorobenzoyl}piperazin-1-yl)-4-methoxypyridinium trifluoroacetate | 451 | 452 | 5 |
| 26 | 4-(1-{5-[(5-Ethyl-6-oxo-1,6-dihydropyridazin-3-yl)methyl]-2-fluorobenzoyl}pyrrolidin-3-yl)pyridinium trifluoroacetate | 406 | 407 | 5 |
| 27 | 1-{5-[(5-Ethyl-6-oxo-1,6-dihydropyridazin-3-yl)methyl]-2-fluorobenzoyl}piperidin-3-yl)-N,N-dimethylmethanaminium trifluoroacetate | 400 | 401 | 5 |
| 28 | 4-Ethyl-6-[4-fluoro-3-(1'H-spiro[1-benzofuran-3,4'-piperidin]-1'-ylcarbonyl)benzyl]pyridazin-3(2H)-one | 447 | 448 | 5 |
| 29 | 1-[2-(1-{5-[(5-Ethyl-6-oxo-1,6-dihydropyridazin-3-yl)methyl]-2-fluorobenzoyl}piperidin-4-yl)ethyl]-1H-pyrazol-2-ium trifluoroacetate | 437 | 438 | 5 |
| 30 | 5-Chloro-2-(4-{5-[(5-ethyl-6-oxo-1,6-dihydropyridazin-3-yl)methyl]-2-fluorobenzoyl}piperazin-1-yl)pyridinium trifluoroacetate | 455/ 457 | 456/ 458 | 5 |
| 31 | 2-(4-{5-[(5-Ethyl-6-oxo-1,6-dihydropyridazin-3-yl)methyl]-2-fluorobenzoyl}piperazin-1-yl)-6-methoxypyridinium trifluoroacetate | 451 | 452 | 5 |
| 32 | 3-Benzyl-7-{5-[(5-ethyl-6-oxo-1,6-dihydropyridazin-3-yl)methyl]-2-fluorobenzoyl}-5,6,7,8-tetrahydroimidazo[1,2-a]pyrazin-1-ium trifluoroacetate | 471 | 472 | 5 |

-continued

| Example | Name | MWt | [M + H]+ | Procedure Of Example |
|---|---|---|---|---|
| 33 | 2-(4-{5-[(5-Ethyl-6-oxo-1,6-dihydropyridazin-3-yl)methyl]-2-fluorobenzoyl}piperazin-1-yl)-3,6-dimethylpyrazin-1-ium trifluoroacetate | 450 | 451 | 5 |
| 34 | 4-Ethyl-6-{4-fluoro-3-[(3-phenyl-5,6-dihydroimidazo[1,2-a]pyrazin-7(8H)-yl)carbonyl]benzyl}-3-oxo-2,3-dihydropyridazin-1-ium trifluoroacetate | 457 | 458 | 5 |
| 35 | 4-{5-[(5-Ethyl-6-oxo-1,6-dihydropyridazin-3-yl)methyl]-2-fluorobenzoyl}-1-(3-methoxybenzyl)piperazin-1-ium trifluoroacetate | 464 | 465 | 5 |
| 36 | 2-(1-{5-[(5-Ethyl-6-oxo-1,6-dihydropyridazin-3-yl)methyl]-2-fluorobenzoyl}piperidin-4-yl)-1,2,3,4-tetrahydroisoquinolinium trifluoroacetate | 474 | 475 | 5 |
| 37 | 4-{5-[(5-Ethyl-6-oxo-1,6-dihydropyridazin-3-yl)methyl]-2-fluorobenzoyl}piperazin-1-ium trifluoroacetate | 344 | 345 | 6 |
| 38 | 4-{5-[(5-Ethyl-6-oxo-1,6-dihydropyridazin-3-yl)methyl]-2-fluorobenzoyl}-3-phenylpiperazin-1-ium trifluoroacetate | 420 | 421 | 6 |
| 39 | 3-Benzyl-4-{5-[(5-ethyl-6-oxo-1,6-dihydropyridazin-3-yl)methyl]-2-fluorobenzoyl}piperazin-1-ium trifluoroacetate | 434 | 435 | 6 |
| 40 | 4-{5-[(5-Ethyl-6-oxo-1,6-dihydropyridazin-3-yl)methyl]-2-fluorobenzoyl}-2-(pyridinium-3-ylmethyl)piperazin-1-ium bis(trifluoroacetate) | 435 | 436 | 6 |
| 41 | 6-(3-{[4-(Cyclopentylcarbonyl)-1,4-diazepan-1-yl]carbonyl}-4-fluorobenzyl)-4,5-dimethylpyridazin-3(2H)-one | 454 | 455 | 5 |
| 42 | 6-(3-{[4-(Cyclopentylcarbonyl)-1,4-diazepan-1-yl]carbonyl}-4-fluorobenzyl)-4-ethylpyridazin-3(2H)-one | 454 | 455 | 5 |
| 43 | 4-{5-[(4,5-Diethyl-6-oxo-1,6-dihydropyridazin-3-yl)methyl]-2-fluorobenzoyl}-1,4-diazepan-1-ium trifluoroacetate | 386 | 387 | 8 |
| 44 | 4-{2-Fluoro-5-[(5-isopropyl-4-methyl-6-oxo-1,6-dihydropyridazin-3-yl)methyl]benzoyl}-1,4-diazepan-1-ium trifluoroacetate | 386 | 387 | 6 |
| 45 | 4-{5-[(4,5-Dimethyl-6-oxo-1,6-dihydropyridazin-3-yl)methyl]-2-fluorobenzoyl}piperazin-1-ium trifluoroacetate | 344 | 345 | 9 |
| 46 | 6-{4-Fluoro-3-[(4-propionylpiperazin-1-yl)carbonyl]benzyl}-4,5-dimethylpyridazin-3(2H)-one | 400 | 401 | 9 |
| 47 | 6-(3-{[4-(Difluoroacetyl)piperazin-1-yl]carbonyl}-4-fluorobenzyl)-4,5-dimethylpyridazin-3(2H)-one | 422 | 423 | 9 |
| 48 | 6-(4-Fluoro-3-{[4-(3,3,3-trifluoropropanoyl)piperazin-1-yl]carbonyl}benzyl)-4,5-dimethylpyridazin-3(2H)-one | 454 | 455 | 9 |
| 49 | 6-{4-Fluoro-3-[(4-isobutyrylpiperazin-1-yl)carbonyl]benzyl}-4,5-dimethyl-3-oxo-2,3-dihydropyridazin-1-ium trifluoroacetate | 414 | 415 | 9 |
| 50 | 2-[(4-{5-[(4,5-Dimethyl-6-oxo-1,6-dihydropyridazin-3-yl)methyl]-2-fluorobenzoyl}piperazin-1-yl)carbonyl]pyridinium trifluoroacetate | 449 | 450 | 9 |
| 51 | 6-(4-Fluoro-3-{[4-(tetrahydrofuran-2-ylcarbonyl)piperazin-1-yl]carbonyl}benzyl)-4,5-dimethylpyridazin-3(2H)-one | 442 | 443 | 9 |
| 52 | 1-(4-{5-[(4,5-Dimethyl-6-oxo-1,6-dihydropyridazin-3-yl)methyl]-2-fluorobenzoyl}piperazin-1-yl)-N,N,2-trimethyl-1-oxopropan-2-aminium trifluoroacetate | 457 | 458 | 9 |
| 53 | 6-(4-Fluoro-3-{[4-(2,2,3,3,3-pentafluoropropanoyl)piperazin-1-yl]carbonyl}benzyl)-4,5-dimethyl-3-oxo-2,3-dihydropyridazin-1-ium trifluoroacetate | 490 | 491 | 3 |
| 54 | 6-(4-Fluoro-3-{[4-(pyrrolidin-1-ylcarbonyl)piperazin-1-yl]carbonyl}benzyl)-4,5-dimethyl-3-oxo-2,3-dihydropyridazin-1-ium trifluoroacetate | 441 | 442 | 3 |
| 55 | 6-(4-Fluoro-3-{[4-(trifluoroacetyl)piperazin-1-yl]carbonyl}benzyl)-4,5-dimethyl-3-oxo-2,3-dihydropyridazin-1-ium trifluoroacetate | 440 | 441 | 3 |

| Example | Name | MWt | [M + H]+ | Procedure Of Example |
|---|---|---|---|---|
| 56 | 1-(1-{5-[(4,5-Dimethyl-6-oxo-1,6-dihydropyridazin-3-yl)methyl]-2-fluorobenzoyl}piperidin-4-yl)piperidinium trifluoroacetate | 426 | 427 | 5 |
| 57 | 1-(1-{5-[(4,5-Dimethyl-6-oxo-1,6-dihydropyridazin-3-yl)methyl]-2-fluorobenzoyl}piperidin-4-yl)pyrrolidinium trifluoroacetate | 412 | 413 | 5 |
| 58 | 4-(4-{5-[(4,5-Dimethyl-6-oxo-1,6-dihydropyridazin-3-yl)methyl]-2-fluorobenzoyl}piperazin-1-yl)quinazolin-1-ium trifluoroacetate | 472 | 473 | 5 |
| 59 | 2-(4-{5-[(4,5-Dimethyl-6-oxo-1,6-dihydropyridazin-3-yl)methyl]-2-fluorobenzoyl}piperazin-1-yl)pyrimidin-1-ium trifluoroacetate | 422 | 423 | 5 |
| 60 | 7-{5-[(4,5-Dimethyl-6-oxo-1,6-dihydropyridazin-3-yl)methyl]-2-fluorobenzoyl}-3-(3-methylphenyl)-5,6,7,8-tetrahydro[1,2,4]triazolo[4,3-a]pyrazine-1,4-diium bis(trifluoroacetate) | 472 | 473 | 5 |
| 61 | 7-{5-[(4,5-Dimethyl-6-oxo-1,6-dihydropyridazin-3-yl)methyl]-2-fluorobenzoyl}-3-[4-(trifluoromethyl)phenyl]-5,6,7,8-tetrahydro[1,2,4]triazolo[4,3-a]pyrazin-1-ium trifluoroacetate | 526 | 527 | 5 |
| 62 | 7-{5-[(4,5-Dimethyl-6-oxo-1,6-dihydropyridazin-3-yl)methyl]-2-fluorobenzoyl}-3-[(4-fluorophenoxy)methyl]-5,6,7,8-tetrahydro[1,2,4]triazolo[4,3-a]pyrazin-2-ium trifluoroacetate | 506 | 507 | 5 |
| 63 | 3-Cyano-2-(4-{5-[(4,5-dimethyl-6-oxo-1,6-dihydropyridazin-3-yl)methyl]-2-fluorobenzoyl}piperazin-1-yl)pyridinium trifluoroacetate | 446 | 447 | 5 |
| 64 | 3-(3,5-Difluorophenyl)-7-{5-[(4,5-dimethyl-6-oxo-1,6-dihydropyridazin-3-yl)methyl]-2-fluorobenzoyl}-5,6,7,8-tetrahydro[1,2,4]triazolo[4,3-a]pyrazin-1-ium trifluoroacetate | 494 | 495 | 5 |
| 65 | 3-[(Dimethylammonio)methyl]-7-{5-[(4,5-dimethyl-6-oxo-1,6-dihydropyridazin-3-yl)methyl]-2-fluorobenzoyl}-5,6,7,8-tetrahydro[1,2,4]triazolo[4,3-a]pyrazin-2-ium bis(trifluoroacetate) | 439 | 440 | 5 |
| 66 | (7-{5-[(4,5-Dimethyl-6-oxo-1,6-dihydropyridazin-3-yl)methyl]-2-fluorobenzoyl}-5,6,7,8-tetrahydro[1,2,4]triazolo[4,3-a]pyrazin-3-yl)-N,N-dimethylmethanaminium trifluoroacetate | 439 | 440 | 14 |
| 67 | 7-{5-[(4,5-Dimethyl-6-oxo-1,6-dihydropyridazin-3-yl)methyl]-2-fluorobenzoyl}-3-(2-furyl)-5,6,7,8-tetrahydro[1,2,4]triazolo[4,3-a]pyrazin-1-ium trifluoroacetate | 448 | 449 | 14 |
| 68 | 7-{5-[(4,5-Dimethyl-6-oxo-1,6-dihydropyridazin-3-yl)methyl]-2-fluorobenzoyl}-3-(pentafluoroethyl)-5,6,7,8-tetrahydro[1,2,4]triazolo[4,3-a]pyrazin-1-ium trifluoroacetate | 500 | 501 | 14 |
| 69 | 7-{5-[(4,5-Dimethyl-6-oxo-1,6-dihydropyridazin-3-yl)methyl]-2-fluorobenzoyl}-3-{[4-(trifluoromethyl)phenyl]amino}-5,6,7,8-tetrahydro[1,2,4]triazolo[4,3-a]pyrazin-1-ium trifluoroacetate | 541 | 542 | 14 |
| 70 | 2-[(4-{2-Fluoro-5-[(6-hydroxy-4,5-dimethylpyridazin-3-yl)methyl]benzoyl}piperazin-1-yl)carbonyl]-2-methylpyrrolidinium chloride | 456 | 457 | 15 |
| 71 | 7-{5-[(4,5-Dimethyl-6-oxo-1,6-dihydropyridazin-3-yl)methyl]-2-fluorobenzoyl}-3-phenyl-5,6,7,8-tetrahydro[1,2,4]triazolo[4,3-a]pyrazin-1-ium trifluoroacetate | 458 | 459 | 14 |

-continued

| Example | Name | MWt | [M + H]+ | Procedure Of Example |
|---|---|---|---|---|
| 72 | 3-(1,3-Benzodioxol-5-yl)-7-{5-[(4,5-dimethyl-6-oxo-1,6-dihydropyridazin-3-yl)methyl]-2-fluorobenzoyl}-5,6,7,8-tetrahydro[1,2,4]triazolo[4,3-a]pyrazin-1-ium trifluoroacetate | 502 | 503 | 14 |
| 73 | 7-{5-[(4,5-Dimethyl-6-oxo-1,6-dihydropyridazin-3-yl)methyl]-2-fluorobenzoyl}-3-(2-thienyl)-5,6,7,8-tetrahydro[1,2,4]triazolo[4,3-a]pyrazin-1-ium trifluoroacetate | 464 | 465 | 14 |
| 74 | 3-Cyclopropyl-6-{5-[(4,5-dimethyl-6-oxo-1,6-dihydropyridazin-3-yl)methyl]-2-fluorobenzoyl}-4,5,6,7-tetrahydro-1H-pyrazolo[3,4-c]pyridin-2-ium trifluoroacetate | 421 | 422 | 14 |
| 75 | 6-{5-[(4,5-Dimethyl-6-oxo-1,6-dihydropyridazin-3-yl)methyl]-2-fluorobenzoyl}-3-(trifluoromethyl)-4,5,6,7-tetrahydro-1H-pyrazolo[3,4-c]pyridin-2-ium trifluoroacetate | 449 | 450 | 14 |
| 76 | 5-{5-[(4,5-Dimethyl-6-oxo-1,6-dihydropyridazin-3-yl)methyl]-2-fluorobenzoyl}-3-(trifluoromethyl)-4,5,6,7-tetrahydro-1H-pyrazolo[4,3-c]pyridin-2-ium trifluoroacetate | 449 | 450 | 14 |
| 77 | 7-{5-[(4,5-Dimethyl-6-oxo-1,6-dihydropyridazin-3-yl)methyl]-2-fluorobenzoyl}-3-pyridinium-3-yl-5,6,7,8-tetrahydro[1,2,4]triazolo[4,3-a]pyrazin-2-ium bis(trifluoroacetate) | 459 | 460 | 14 |
| 78 | 7-{5-[(4,5-Dimethyl-6-oxo-1,6-dihydropyridazin-3-yl)methyl]-2-fluorobenzoyl}-7-aza-1-azoniaspiro[3.5]nonane trifluoroacetate | 384 | 385 | 10 |
| 79 | 1-[(1-{3-[(4,5-Dimethyl-6-oxo-1,6-dihydropyridazin-3-yl)methyl]-2-fluorobenzoyl}azetidin-3-yl)methyl]pyrrolidinium trifluoroacetate | 398 | 399 | 14 |
| 80 | 1-(1-{3-[(4,5-Dimethyl-6-oxo-1,6-dihydropyridazin-3-yl)methyl]-2-fluorobenzoyl}piperidin-4-yl)-3,3-difluoroazetidinium trifluoroacetate | 434 | 435 | 14 |
| 81 | 5-{5-[(4,5-Dimethyl-6-oxo-1,6-dihydropyridazin-3-yl)methyl]-2-fluorobenzoyl}-1-(2,2,2-trifluoroethyl)-4,5,6,7-tetrahydro-1H-[1,2,3]triazolo[4,5-c]pyridin-3-ium trifluoroacetate | 464 | 465 | 14 |
| 82 | 1-[(4-{5-[(4,5-Dimethyl-6-oxo-1,6-dihydropyridazin-3-yl)methyl]-2-fluorobenzoyl}piperazin-1-yl)carbonyl]-n-methylcyclopentanaminium trifluoroacetate | 469 | 470 | 18 |
| 83 | 7-{5-[(4,5-Dimethyl-6-oxo-1,6-dihydropyridazin-3-yl)methyl]-2-fluorobenzoyl}-1-methyl-7-aza-1-azoniaspiro[3.5]nonane trifluoroacetate | 398 | 399 | 11 |
| 84 | 6-(4-Methoxy-3-{[3-(trifluoromethyl)-5,6-dihydro[1,2,4]triazolo[4,3-a]pyrazin-7(8H)-yl]carbonyl}benzyl)-4,5-dimethyl-3-oxo-2,3-dihydropyridazin-1-ium trifluoroacetate | 462 | 463 | 13 |
| 85 | 8-{5-[(4,5-Dimethyl-6-oxo-1,6-dihydropyridazin-3-yl)methyl]-2-fluorobenzoyl}-8-aza-2-azoniaspiro[4.5]decane trifluoroacetate | 398 | 399 | 10 |
| 86 | 2-[(4-{5-[(4,5-Dimethyl-6-oxo-1,6-dihydropyridazin-3-yl)methyl]-2-fluorobenzoyl}piperazin-1-yl)carbonyl]-2-propylpyrrolidinium trifluoroacetate | 483 | 484 | 18 |
| 87 | 8-{5-[(4,5-Dimethyl-6-oxo-1,6-dihydropyridazin-3-yl)methyl]-2-fluorobenzoyl}-2-methyl-8-aza-2-azoniaspiro[4.5]decane trifluoroacetate | 412 | 413 | 11 |
| 88 | 3-[(4-{5-[(4,5-Dimethyl-6-oxo-1,6-dihydropyridazin-3-yl)methyl]-2-fluorobenzoyl}piperazin-1-yl)carbonyl]piperidinium trifluoroacetate | 455 | 456 | 18 |
| 89 | 3-[(4-{5-[(4,5-Dimethyl-6-oxo-1,6-dihydropyridazin-3-yl)methyl]-2- | 469 | 470 | 18 |

| Example | Name | MWt | [M + H]+ | Procedure Of Example |
|---|---|---|---|---|
| | fluorobenzoyl}piperazin-1-yl)carbonyl]-1-methylpiperidinium trifluoroacetate | | | |
| 90 | 1-[(4-{5-[(4,5-Dimethyl-6-oxo-1,6-dihydropyridazin-3-yl)methyl]-2-fluorobenzoyl}piperazin-1-yl)carbonyl]-N,N-dimethylcyclopropanaminium trifluoroacetate | 455 | 456 | 18 |
| 91 | 3-(4-{5-[(4,5-Dimethyl-6-oxo-1,6-dihydropyridazin-3-yl)methyl]-2-fluorobenzoyl}piperazin-1-yl)-N,N-dimethyl-3-oxopropan-1-aminium trifluoroacetate | 443 | 444 | 18 |
| 92 | 2-Benzyl-2-[(4-{5-[(4,5-dimethyl-6-oxo-1,6-dihydropyridazin-3-yl)methyl]-2-fluorobenzoyl}piperazin-1-yl)carbonyl]pyrrolidinium trifluoroacetate | 531 | 532 | 18 |
| 93 | 4,5-Dimethyl-6-(3-{[3-(trifluoromethyl)-5,6-dihydro[1,2,4]triazolo[4,3-a]pyrazin-7(8H)-yl]carbonyl}benzyl)pyridazin-3(2H)-one trifluoroacetate | 432 | 433 | 14 |
| 94 | 6-[3-(1,8-Diazaspiro[4.5]dec-8-ylcarbonyl)-4-fluorobenzyl]-4-ethyl-3-oxo-2,3-dihydropyridazin-1-ium trifluoroacetate | 398 | 399 | 10 |
| 95 | 3-[(4-{5-[(4,5-Dimethyl-6-oxo-1,6-dihydropyridazin-3-yl)methyl]-2-fluorobenzoyl}piperazin-1-yl)carbonyl]pyrrolidinium trifluoroacetate | 441 | 442 | 18 |
| 96 | 1-[(4-{5-[(4,5-Dimethyl-6-oxo-1,6-dihydropyridazin-3-yl)methyl]-2-fluorobenzoyl}piperazin-1-yl)carbonyl]-N-methylcyclopropanaminium trifluoroacetate | 441 | 442 | 18 |
| 97 | 3-[(4-{5-[(4,5-Dimethyl-6-oxo-1,6-dihydropyridazin-3-yl)methyl]-2-fluorobenzoyl}piperazin-1-yl)carbonyl]-1-methylpyrrolidinium trifluoroacetate | 455 | 456 | 18 |
| 98 | 3-(4-{5-[(4,5-Dimethyl-6-oxo-1,6-dihydropyridazin-3-yl)methyl]-2-fluorobenzoyl}piperazin-1-yl)-1,1,1-trifluoro-N,N-dimethyl-3-oxopropan-2-aminium trifluoroacetate | 497 | 498 | 18 |
| 99 | 2-[(4-{5-[(4,5-Dimethyl-6-oxo-1,6-dihydropyridazin-3-yl)methyl]-2-fluorobenzoyl}piperazin-1-yl)carbonyl]-2-methylpiperidinium trifluoroacetate | 469 | 470 | 18 |
| 100 | Benzyl 2-[(4-{5-[(4,5-dimethyl-6-oxo-1,6-dihydropyridazin-3-yl)methyl]-2-fluorobenzoyl}piperazin-1-yl)carbonyl]-2-methylpiperidine-1-carboxylate | 603 | 604 | 18 |
| 101 | 4-Ethyl-6-(4-fluoro-3-{[1-(2,2,2-trifluoroethyl)-1,4,6,7-tetrahydro-5h-[1,2,3]triazolo[4,5-c]pyridin-5-yl]carbonyl}benzyl)pyridazin-3(2H)-one | 464 | 465 | 14 |
| 102 | 4-Ethyl-6-{4-fluoro-3-[(1-methyl-1,8-diazaspiro[4.5]dec-8-yl)carbonyl]benzyl}-3-oxo-2,3-dihydropyridazin-1-ium trifluoroacetate | 412 | 413 | 11 |
| 103 | (2S)-2-[2-(4-{5-[(4,5-Dimethyl-6-oxo-1,6-dihydropyridazin-3-yl)methyl]-2-fluorobenzoyl}piperazin-1-yl)-2-oxoethyl]pyrrolidinium trifluoroacetate | 455 | 456 | 18 |
| 104 | 8-{5-[(4,5-Dimethyl-6-oxo-1,6-dihydropyridazin-3-yl)methyl]-2-fluorobenzoyl}-1-ethyl-8-aza-1-azoniaspiro[4.5]decane trifluoroacetate | 426 | 427 | 11 |
| 105 | 1-(Cyclopropylmethyl)-8-{5-[(4,5-dimethyl-6-oxo-1,6-dihydropyridazin-3-yl)methyl]-2-fluorobenzoyl}-8-aza-1-azoniaspiro[4.5]decane trifluoroacetate | 452 | 453 | 11 |
| 106 | 6-[3-({4-[(1-Anilinocyclopentyl)carbonyl]piperazin-1-yl}carbonyl)-4-fluorobenzyl]-4,5-dimethylpyridazin-3(2H)-one | 531 | 532 | 5 |
| 107 | 6-[3-({4-[(1-Aminocyclopentyl)carbonyl]piperazin-1-yl}carbonyl)-4-fluorobenzyl]-4,5-dimethylpyridazin-3(2H)-one | 455 | 456 | 19 |
| 108 | 6-{3-[(4-{1-(Benzylamino)cyclopentyl]carbonyl}piperazin- | 545 | 456 | 19 |

| Example | Name | MWt | [M + H]+ | Procedure Of Example |
|---|---|---|---|---|
| | 1-yl)carbonyl]-4-fluorobenzyl}-4,5-dimethylpyridazin-3(2H)-one trifluoroacetate | | | |
| 109 | 6-(3-{[4-({1-[(Cyclopropylmethyl)amino]cyclopentyl}carbonyl)piperazin-1-yl]carbonyl}-4-fluorobenzyl)-4,5-dimethylpyridazin-3(2H)-one trifluoroacetate | 509 | 510 | 19 |
| 110 | 6-[4-Fluoro-3-({4-[2-(4-fluorobenzyl)prolyl]piperazin-1-yl}carbonyl)benzyl]-4,5-dimethylpyridazin-3(2H)-one trifluoroacetate | 549 | 550 | 18 |
| 111 | 6-[4-Fluoro-3-({4-[2-(4-methylbenzyl)prolyl]piperazin-1-yl}carbonyl)benzyl]-4,5-dimethylpyridazin-3(2H)-one trifluoroacetate | 545 | 546 | 18 |
| 112 | 6-[4-Fluoro-3-({4-[2-(1-naphthylmethyl)prolyl]piperazin-1-yl}carbonyl)benzyl]-4,5-dimethylpyridazin-3(2H)-one trifluoroacetate | 581 | 582 | 18 |
| 113 | 6-(3-{[4-(2-Ethylprolyl)piperazin-1-yl]carbonyl}-4-fluorobenzyl)-4,5-dimethylpyridazin-3(2H)-one trifluoroacetate | 469 | 470 | 18 |

The invention claimed is:

1. A compound of formula II:

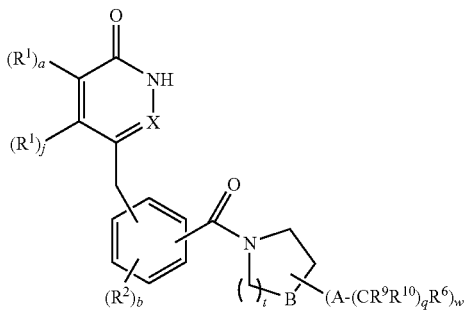

(II)

wherein:
the sum of a and j is 1 or 2;
b is 0, 1, 2 or 3;
t is 0, 1, 2 or 3;
when t is 0 then B is $CH_2$;
when t is 1, 2 or 3 then B is $CH_2$, NH or O;
w is 0, 1, 2 or 3;
X is N;
each $R^1$ is independently $C_{1-6}$alkyl, halo$C_{1-6}$alkyl, halogen or cyano;
each $R^2$ is independently hydroxy, halogen, cyano, nitro, $C_{1-6}$alkyl, halo$C_{1-6}$alkyl, $C_{1-6}$alkoxy, halo$C_{1-6}$alkoxy or $NR^aR^b$;
each A is independently a direct bond, O, C=O, (C=O)$NR^7$, $NR^7$(C=O), (C=O)O, O(C=O), (C=S)$NR^7$, $NR^7$ or S(O)$_r$;
each q is independently 0, 1, 2, 3, or 4;
r is 0, 1 or 2;
each $R^6$ is independently hydroxy, cyano, halogen, nitro, $C_{1-6}$alkyl, $C_{2-10}$alkenyl, halo$C_{1-6}$alkyl, $NR^aR^b$ or a ring which is: $C_{3-10}$cycloalkyl; $C_{6-10}$aryl; $C_{6-10}$aryloxy; 4 membered saturated heterocyclic ring containing one N atom; a 5, 6 or 7 membered saturated or partially saturated heterocyclic ring containing one, two or three atoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one or more groups independently selected from $R^8$;

$R^7$ is hydrogen or $R^6$;

each $R^8$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, —O(C=O)$C_{1-6}$alkyl, —(C=O)O$C_{1-6}$alkyl, $NR^aR^b$ or a ring which is: $C_{3-10}$cycloalkyl, $C_{6-10}$aryl$C_{1-6}$alkyl, $C_{6-10}$aryl$C_{1-6}$alkoxycarbonyl, $C_{6-10}$aryl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one or more groups independently selected from halogen, $C_{1-6}$alkyl or halo$C_{1-6}$alkyl;

each of $R^9$ and $R^{10}$ is independently hydrogen, halogen, $C_{1-6}$alkyl or halo$C_{1-6}$alkyl;

each of $R^a$ and $R^b$ is independently selected from hydrogen, $C_{1-6}$alkyl, $C_{3-10}$cycloalkyl, $C_{3-10}$cycloalkyl, $C_{3-10}$cycloalkyl$C_{1-6}$alkyl, $C_{1-6}$aryl or $C_{6-10}$aryl$C_{1-6}$alkyl;

or a pharmaceutically acceptable salt or tautomer thereof.

2. A compound of formula VII:

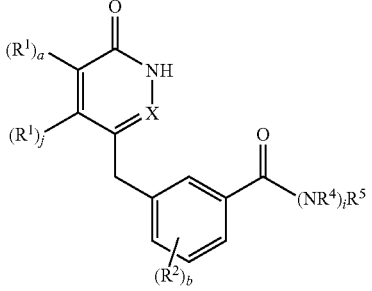

(VII)

wherein:
the sum of a and j is 1 or 2;
b is 0, 1, 2 or 3;
i is 0 or 1;
X is N;
each $R^1$ is independently $C_{1-6}$alkyl, halo$C_{1-6}$alkyl, halogen or cyano;
each $R^2$ is independently hydroxy, halogen, cyano, nitro, $C_{1-6}$alkyl, halo$C_{1-6}$alkyl, $C_{1-6}$alkoxy, halo$C_{1-6}$alkoxy or $NR^aR^b$;
$R^4$ is hydrogen or $C_{1-6}$alkyl;
$R^5$ is a 4 membered saturated heterocyclic ring containing one N atom, a 5 or 6 membered saturated or partially saturated heterocyclic ring containing one, two or three N atoms and zero or one O atom or a 7-15 membered partially saturated or saturated heterocyclic ring containing 1, 2, 3 or 4 heteroatoms independently selected from N, O and S; any of which rings being optionally substituted by one or more groups independently selected from $A\text{-}(CR^9R^{10})_qR^6$;
each A is independently a direct bond, O, C=O, (C=O)$NR^7$, $NR^7$(C=O), (C=O)O, O(C=O), (C=S)$NR^7$, $NR^7$ or $S(O)_r$;
each q is independently 0, 1, 2, 3, or 4;
r is 0, 1 or 2;
each $R^6$ is independently hydroxy, cyano, halogen, nitro, $C_{1-6}$alkyl, $C_{2-10}$alkenyl, halo$C_{1-6}$alkyl, $NR^aR^b$ or a ring which is: $C_{3-10}$cycloalkyl; $C_{6-10}$aryl; $C_{6-10}$aryloxy; 4 membered saturated heterocyclic ring containing one N atom; a 5, 6 or 7 membered saturated or partially saturated heterocyclic ring containing one, two or three atoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered unsaturated or partially saturated heterocyclic ring containing 1, 2, 3 or 4 heteroatoms independently selected from N, O and S; any of which rings being optionally substituted by one or more groups independently selected from $R^8$;
$R^7$ is hydrogen or $R^6$;
each $R^8$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, —O(C=O)$C_{1-6}$alkyl, —(C=O)O$C_{1-6}$alkyl, $NR^aR^b$ or a ring which is: $C_{3-10}$cycloalkyl, $C_{6-10}$aryl$C_{1-6}$alkyl, $C_{6-10}$aryl$C_{1-6}$alkoxycarbonyl, $C_{6-10}$aryl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one or more groups independently selected from halogen, $C_{1-6}$alkyl or halo$C_{1-6}$alkyl;
each of $R^9$ and $R^{10}$ is independently hydrogen, halogen, $C_{1-6}$alkyl or halo$C_{1-6}$alkyl;
each of $R^a$ and $R^b$ is independently selected from hydrogen, $C_{1-6}$alkyl, $C_{3-10}$cycloalkyl, $C_{3-10}$cycloalkyl, $C_{3-10}$cycloalkyl$C_{1-6}$alkyl, $C_{1-6}$aryl or $C_{6-10}$aryl$C_{1-6}$alkyl;
or a pharmaceutically acceptable salt or tautomer thereof.

* * * * *